US008506947B2

(12) United States Patent
McCart et al.

(10) Patent No.: US 8,506,947 B2
(45) Date of Patent: Aug. 13, 2013

(54) VACCINIA VIRUS EXPRESSION VECTOR FOR SELECTIVE REPLICATION IN A TUMOR CELL AND INTRODUCTION OF EXOGENOUS NUCLEOTIDE SEQUENCE INTO A TUMOR CELL

(75) Inventors: J. Andrea McCart, Toronto (CA); David L. Bartlett, Pittsburgh, PA (US); Bernard Moss, Bethesda, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 696 days.

(21) Appl. No.: 11/707,453

(22) Filed: Feb. 16, 2007

(65) Prior Publication Data

US 2007/0154458 A1 Jul. 5, 2007

Related U.S. Application Data

(60) Division of application No. 09/991,721, filed on Nov. 13, 2001, now Pat. No. 7,208,313, which is a continuation of application No. PCT/US00/14679, filed on May 26, 2000.

(60) Provisional application No. 60/137,126, filed on May 28, 1999.

(51) Int. Cl.
*A61K 33/00* (2006.01)
*C12N 15/00* (2006.01)

(52) U.S. Cl.
USPC ................. 424/93.1; 514/44 R; 435/320.1

(58) Field of Classification Search
None
See application file for complete search history.

(56) References Cited

U.S. PATENT DOCUMENTS

| | | | |
|---|---|---|---|
| 5,236,838 A | | 8/1993 | Rasmussen et al. |
| 5,310,671 A | * | 5/1994 | Binns et al. ............... 435/235.1 |
| 5,622,835 A | | 4/1997 | Herlyn et al. |
| 5,739,027 A | | 4/1998 | Kamb |
| 5,744,133 A | | 4/1998 | Lathe |
| 5,851,991 A | | 12/1998 | Lee et al. |
| 5,942,235 A | * | 8/1999 | Paoletti ..................... 424/232.1 |
| 5,962,260 A | | 10/1999 | Sawamura et al. |
| 5,981,714 A | | 11/1999 | Cheng et al. |
| 6,093,700 A | | 7/2000 | Mastrangelo et al. |
| 6,103,244 A | | 8/2000 | Dorner et al. |

FOREIGN PATENT DOCUMENTS

| | | |
|---|---|---|
| DE | 3411472 A1 | 10/1984 |
| EP | 0206920 | 12/1986 |
| EP | 0284791 | 10/1988 |
| EP | 0 443 335 | 8/1991 |
| EP | 0585960 A2 | 9/1994 |
| JP | 55026477 A | 2/1980 |
| JP | 402065779 A | 3/1990 |
| WO | WO8802022 | 3/1988 |
| WO | WO8903879 | 5/1989 |
| WO | WO 89/08716 | 9/1989 |
| WO | WO 92/15672 | 9/1992 |
| WO | WO 94/16716 | 8/1994 |
| WO | WO 94/10575 | 11/1994 |
| WO | WO 95/31105 | 11/1995 |
| WO | WO 98/08394 | 5/1998 |
| WO | WO 99/18799 | * 4/1999 |

OTHER PUBLICATIONS

Ossina et al., 1997, The Journal of Biological Chemistry, 272: 16351-16357.*
Abdel-Wahab et al., 1997, Cancer, 80: 401-412.*
Martin et al., 1998, The Journal of Biological Chemistry, 273: 4345-4349.*
Robbins et al., 1991, Cancer Research 51: 3657-3662.*
Mullen et al., 1994, Cancer Research, 54: 1503-1506,.*
Advani, S. J., et al. (1999) Replication-competent, Nonneuroinvasive Genetically Engineered Herpes Virus is Highly Effective in the Treatment of Therapy-resistant Experimental Human Tumors. Cancer Res. 59:2055-2058.
Beer, S. J., et al. (1998) Poly (lactic-glycolic) acid copolymer encapsulation of recombinant adenovirus reduces immunogenicity in vivo. Gene Ther. 5:740-746.
Buller, R. M. L., et al. (1988) Deletion of the Vaccinia Virus Growth Factor Gene Reduces Virus Virulence. J. Virol. 62(3):866-874.
Buller, R. M. L., et al. (1988) Cell Proliferative Response to Vaccinia Virus is Mediated by VGF. Virology 164:182-192.
Buller, R. M., et al. (1985) Decreased virulence of recombinant vaccinia virus expression vectors is associated with a thymidine kinase-negative phenotype. Nature 317:813-815.
Carroll, M. W. and Moss, B. (1997) Poxviruses as expression vectors. Curr. Opin. Biotechnol. 8:573-577.
Chakrabarti, S., et al. (1997) Compact, Synthetic, Vaccinia Virus Early/Late Promoter for Protein Expression. BioTechniques 23:1094-1097.
Chase, M., et al. (1998) an oncolytic viral mutant that delivers the *CYP2B1* transgene and augments cyclophosphamide chemotherapy. Nat. Biotech. 16:444-448.
Chillon, M., et al. (1998) Adenovirus complexed with polyethylene glycol and cationic lipid is shielded from neutralizing antibodies in vitro. Gene Ther. 5:995-1002.
Davison, A. J. and Moss, B. (1989) Structure of Vaccinia Virus Early Promoters. J. Mol. Biol. 210:749-769.
Dmitriev, I., et al. (1998) An Adenovirus Vector with Genetically Modified Fibers Demonstrates Expanded Tropism via Utilization of a Coxsackievirus and Adenovirus Receptor-Independent Cell Entry Mechanism. J. Virol. 72(12):9706-9713, 1998.

(Continued)

*Primary Examiner* — Deborah Crouch
(74) *Attorney, Agent, or Firm* — Klarquist Sparkman, LLP

(57) ABSTRACT

A composition of matter comprising a vaccinia virus expression vector with a negative thymidine kinase phenotype and a negative vaccinia virus growth factor phenotype.

20 Claims, 6 Drawing Sheets

(56) References Cited

OTHER PUBLICATIONS

Davison, A. J. and Moss, B. (1989) Structure of Vaccinia Virus Late Promoters. J. Mol. Biol. 210:771-784.
Flexner, C., et al. (1990) Attenuation and immunogenicity in primates of vaccinia virus recombinants expressing human interleukin-2. Vaccine 8:17-21.
Galmiche, M. C., et al. (1997) Expression of a functional single chain antibody on the surface of extracellular enveloped vaccinia virus as a step towards selective tumour cell targeting. J. Gen. Virol. 78:3019-3027.
Gnant, M. F. X., et al. (1999) Systemic Administration of a Recombinant Vaccinia Virus Expressing the Cytosine Deaminase Gene and Subsequent Treatment with 5-Fluorocytosine Leads to Tumor-specific Gen Expression and Prolongation of Survival in Mice. Cancer Res. 59:3396-3403.
Gnant, M. F. X., et al. (1999) Regional Versus Systemic Delivery of Recombinant Vaccinia Virus as Suicide Gene Therapy for Murine Liver Metastases. Ann. Surg. 230(3):352-361.
Goede, V., et al. (1998) Analysis of Blood Vessel Maturation Processes during Cyclic Ovarian Anglogenesis. Lab. Investig. 78(11):1385-4394.
Gurvich, E. B. and Vilesova, I. S. (1983) Vaccinia Virus in Postvaccinal Encephalitis. Acta. Virol. 27:154-159.
Heise, C., et al. (1997) ONYX-015, an E1B gene-attenuated adenovirus, causes tumor-specific cytoilysis and antitumoral efficacy that can be augmented by standard chemotherapeutic agents. Nat. Med. 3(6):639-645.
Hodge, J. W., et al. (1994) Induction of Antitumor Immunity by Recombinant Vaccinia Viruses Expressing B7-1 or B7-2 Costimulatory Molecules. Cancer Res. 54:5552-5555.
Kantor, J., et al. (1992) Immunogenicity and Safety of a Recombinant Vaccinia Virus Vaccine Expressing the Carcinoembryonic Antigen Gene in a Nonhuman Primate. Cancer Res. 52:6917-6925.
Kaplan, E. L. and Meier, P. (1958) Nonparametric Estimation From Incomplete Observations. Am. Stat. Assoc. J. 53:457-481.
Karupiah, G., et al. (1990) Vaccinia virus-mediated damage of murine ovaries and protection by virus-expressed Interleukin-2. Immunol. Cell Biol. 68:325-333.
Keane, J. T., et al. (1983) Progressive Vaccinia Associated With Combined Variable Immunodeficiency. Arch. Dermatol. 119:404-408.
Kim, C. J., et al. (1998) Use of Recombinant Proxviruses to Stimulate Anti-Melanoma T Cell Reactivity. Ann. Surg. Oncol. 5(1):64-76.
Kim, D. H., and McCormick, F. (1996) Replicating viruses as selective cancer therapeutics. Mol. Med. Today 2:519-527.
Kohn, S. et al. (1992) Pathways of Macromolecular Tracer Transport Across Venules and Small Veins. Lab. Investig. 67(5):596-607.
Lane, J. M. and Millar, J. D. (1971) Risks of Smallpox Vaccination Complications in the United States. Am. J. Epidemiol. 93(4):238-240.
Mantel, N. (1966) Evaluation of Survival Data and Two New Rank Order Statistics Arising in its Consideration. Cancer Chemother. Reps. 50(3):163-170.
Martuza, R. L., et al. (1991) Experimental Therapy of Human Glioma by Means of a Genetically Engineered Virus Mutant. Science 252:854-856, 1991.
Mastrangelo, M. J., et al. (2000) Intralesional Vaccinia/GM-CSF Recombinant Virus in the Treatment of Metastatic Melanoma. Adv. Exp. Med. Biol. 465:391-400.
Mastrangelo, M. J., et al. (1998) Intratumoral recombinant GM-CSF-encoding virus as gene therapy in patients with cutaneous melanoma. Cancer Gene Ther. 6(5):409-422.
McAneny, D., et al. (1996) Results of a Phase I Trial of a Recombinant Vaccinia Virus That Expresses Carcinoembryonic Antigen in Patients with Advanced Colorectal Cancer. Ann. Sum. Oncol. 3(5):495-500.
McCart, J. A., et al. (2001) Systemic Cancer therapy with a Tumor-selective Vaccinia Virus Mutant Lacking Thymidine Kinase and Vaccinia Growth Factor Genes. Cancer Res. 61:8751-8757.
McCart, J. A., et al. (2000) Complex interactions between the replicating oncolytic effect and the enzyme/prodrug effect of vaccinia-mediated tumor regression. Gene Ther. 7:1217-1223.
Meko, J. B., et al. (1995) High Cytokine Production and Effective Antitumor Activity of a Recombinant Vaccinia Virus Encoding Murine Interleukin 12, Cancer Res. 55:4765-4770.
Moss, B. (1996) Genetically engineered poxviruses for recombinant gene expression, vaccination, and safety. PNAS USA 93:11341-11348.
Mukherjee, S., et al. (2000) Replication-restricted vaccinia as a cytokine gene therapy vector in cancer: Persistent transgene expression despite antibody generation. Cancer Gene Ther. 7(5):663-670.
O'Reilly, M. S., et al. (1997) Endostatin: an Endogenous Inhibitor of Angiogenesis and Tumor Growth. Cell 88:277-285.
Overwijk, W., et al. (1999)Vaccination with a recombinant vaccinia virus encoding a "self" antigen induces autoimmune vitiligo and tumor cell destruction in mice: Requirement for CD4+ T lymphocytes. PNAS USA 96:2982-2987.
Palumbo, G. J., et al. (1998) A Replication Competent Recombinant Vaccinia Vector Expressing HSV-TK for the Treatment of Tumorsin Vivo. Am. Soc. Gene Ther. 1:169a.
Park, B. J., et al. (1999) Augmentation of Melanoma-Specific Gene Expression Using a Tandem Melanocyte-Specific Enhancer Results in Increased Cytotoxidty of the Purine Nucleoside Phosphorylase Gene in Melanoma. Hum. Gene Ther. 10:889-898.
Parr, M. J., et al. (1997) Tumor-selective transgene expression in vivo mediated by an E2F-responsive adenoviral vector. Nat. Med. 3(10):1145-1149.
Peplinski, G. R., et al. (1998) Vaccinia Virus for Human Gene Therapy. Surg. Onool. Clin. N. Am. 7(3):575-588.
Peplinski, G. R., et al. (1995) In vivo gene therapy of a murine pancreas tumor with recombinant vaccinia virus encoding human interleukin-1 beta. Surgery 118(2):185-191.
Puhlmann, M., et al. (2000) Vaccinia as a vector for tumor-directed gene therapy: Biodistribution of a thymidine kinase-deleted mutant. Cancer Gene Ther. 7(1):66-73.
Puhlmann, M., et al. (1999) Thymidine Kinase-Deleted Vaccinia Virus Expressing Purine Nucleoside Phosphorylase as a Vector for Tumor-Directed Gene Therapy. Hum. Gene Ther. 10:649-857.
Qin, H. and Chatterjee, S. K. (1996) Cancer Gene Therapy Using Tumor Cells Infected with Recombinant Vaccinia Virus Expressing GM-CSF. Hum. Gene Ther. 7:1853-1860.
Ramshaw, I. A., et al. (1987) Recovery of Immunodeficient mice from a vaccinia virus/IL-2 recombinant infection. Nature 329:545-546.
Reynolds, L. P., et al. (2000) Angiogenesis in the Corpus Luteum. Endocrine. 12(1):1-9.
Robinson, M. J., et al. (1977) A Fatal Case of Progressive Vaccinia—Clinical and Pathological Studies. Aust. Paedial. J. 13:125-130.
Roper, R. L. and Moss, B. (1999) Envelope Formation Is Blocked by Mutation of a Sequence Related to the HKD Phospholipid Metabolism Motif in the Vaccinia Virus F13L Protein. J. Viral. 73(2):1108-1117.
Rosenberg, S. A., et al. (1999) Human Gene Marker/Therapy Clinical Protocols. Hum. Gene Ther. 10:3067-3123.
Siders, W. M., et al. (1996) Transcriptional Targeting of Recombinant Adenoviruses to Human and Murine Melanoma Cells. Cancer Research 56:5638-5646.
Smith, G. L. and Moss, B. (1983) Infectious poxvirus vectors have capacity for at least 25000 base pairs of foreign DNA. Gene 25:21-28.
Turkel, S. B. and Overturf, G. D. (1977) Vaccinia Necrosum Complicating Immunoblastic Sarcoma. Cancer 40:226-233.
Walker, J. R., et al. (1999) Local and Systemic Therapy of Human Prostate Adenocarcinoma with the Conditionally Replicating Herpes Simplex Virus Vector G207. Hum. Gene Ther. 10:2237-2243.
Wildner, O., et al. (1999) Therapy of Colon Cancer with Oncolytic Adenovirus is Enhanced by the Addition of Herpes Simplex Virus—*thymidine kinase*. Cancer Res. 59:410-413.
International Search Report from Application No. PCT/US00/14679 dated Sep. 11, 2000.
Child et al,. Insertional inactivation of the large subunit of ribonucleotide reductase encoded by vaccinia virus is associated with reduced virulence in vitro' *Virology*, 174:625-629, 1990.
Kaplan, "Vaccinia virus: a suitable vehicle for recombinant vaccines?" *Arch Virol.*, 106(1-2): 127-39, 1989.
Tartaglia et al., "NYVAC: a highly attenuated strain of vaccinia virus," *Virology*, 188:217-232, 1992.

Zhang et al., "An enhanced green fluorescent protein allows sensitive detection of gene transfer in mammalian cells." *Biochem Biophys Res. Commun.*, Oct. 23, 1996 227(3): 701-11.

D.B. Boyle et al.: "Multiple-cloning-site plasmids for the rapid construction of recombinant poxviruses" *Gene*, vol. 35, Issues 1-2 169-177, 1985.

Chang et al., "Attenuated Deletion Mutant of Vaccinia Virus IHD-W Recovered Virulence by Reinsertion of a Terminal Restriction Fragment," *Microb. Pathog. 13*:49-59, 1992.

Meisinger-Henschel et al., "Introduction of the Six Major Genomic Deletions of Modified Vaccinia Virus Ankara (MVA) into the Parental Vaccinia Virus is Not Sufficient to Reproduce an MVA-Like Phenotype in Cell Culture and in Mice," *J. Virol. 84*:9907-9919, 2010.

Yang et al., "A New Recombinant Vaccinia with Targeted Deletion of Three Viral Genes: Its Safety and Efficacy as an Oncolytic Virus," *Gene Ther. 14*:638-647, 2007.

* cited by examiner

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: TK sense primer

<400> SEQUENCE: 1
gatcttctat ctcggtttcc tcac                                           24

<210> SEQ ID NO 2
<211> LENGTH: 24
<212> TYPE: DNA
<213> ORGANISM: Artificial Sequence
<220> FEATURE:
<223> OTHER INFORMATION: TK antisense primer

<400> SEQUENCE: 2
gatcgataat agatacggaa cggg                                           24

<210> SEQ ID NO 3
<211> LENGTH: 20
<212> TYPE: DNA
<213> ORGANISM: Artificial Sequence
<220> FEATURE:
<223> OTHER INFORMATION: VGF sense primer

<400> SEQUENCE: 3
ctgatgttgt tgttcgtcgc                                                20

<210> SEQ ID NO 4
<211> LENGTH: 25
<212> TYPE: DNA
<213> ORGANISM: Artificial Sequence
<220> FEATURE:
<223> OTHER INFORMATION: VGF antisense primer

<400> SEQUENCE: 4
ggtagtttag ttcgtcgagt gaacc                                          25

<210> SEQ ID NO 5
<211> LENGTH: 45
<212> TYPE: DNA
<213> ORGANISM: Artificial Sequence
<220> FEATURE:
<223> OTHER INFORMATION: primer

<400> SEQUENCE: 5
atcggagctc tttttatctg cgcggttaac cgccttttta tccat                    45
```

```
<210> SEQ ID NO 6
<211> LENGTH: 45
<212> TYPE: DNA
<213> ORGANISM: Artificial Sequence
<220> FEATURE:
<223> OTHER INFORMATION: primer

<400> SEQUENCE: 6
atcgtctaga ctccacaata aaaacagatc acctgatgga taaaa                45
```

US 8,506,947 B2

VACCINIA VIRUS EXPRESSION VECTOR FOR SELECTIVE REPLICATION IN A TUMOR CELL AND INTRODUCTION OF EXOGENOUS NUCLEOTIDE SEQUENCE INTO A TUMOR CELL

CROSS REFERENCE TO RELATED APPLICATIONS

The present application is a divisional of U.S. application Ser. No. 09/991,721, filed Nov. 13, 2001 which claims the benefit of priority from PCT/US00/14679, filed May 26, 2000, which claims the benefit of U.S. Provisional Patent Application No. 60/137,126, filed May 28, 1999, each of which is hereby incorporated by reference in their entirety.

BACKGROUND OF THE INVENTION

1. Field of the Invention

The present invention relates to mutant vaccinia virus expression vectors. The mutant expression vectors of the present invention show substantially no virus replication in non-dividing cells and as such are superior to previous vaccinia virus expression vectors. More specifically, the vaccinia virus expression vectors of the present invention are associated with negative thymidine kinase and vaccinia virus growth factor phenotypes. The vaccinia virus vectors of the present invention are suitable for use as vaccines, cancer therapies, as well as for gene delivery vectors.

2. Description of the Related Art

Vaccinia virus has a long history of service as an expression vehicle. Vaccinia virus has been used most notably as a vaccination against smallpox, however, active immunization against smallpox is far less common since the eradication of the disease in 1977. Today, as a result of various advances in molecular biology, the vaccinia virus show promise as a vaccine against diseases other than smallpox.

The vaccinia virus genome can be manipulated using general molecular biology techniques well known in the art, to perform as an expression vector for exogenous, non-vaccinia virus genes. In one study, a region of the wild-type (WT) strain of vaccinia virus was shown to be suitable for the insertion and expression of foreign DNA. Mackett, et al., *Proc Natl Acad Sci USA*, 79(23):7415-9 (1982). The ability to express foreign DNA by exploiting a vaccinia virus vector created the possibility that vaccinia virus engineered to express exogenous, non-vaccinia virus genes could be used as gene expression vectors.

Recombinant vaccinia virus carrying exogenous nucleic acid encoding a pathogenic antigen protects an animal infected with the recombinant vaccinia virus and subsequently challenged with the pathogen from which the antigen was derived. For example, when live vaccinia virus recombinants expressing the hepatitis B virus surface antigen (HBsAg), the influenza A virus haemagglutinin, the herpes simplex virus (HSV) type 1 D glycoprotein, the rabies virus G glycoprotein, and the vesicular stomatitis virus G glycoprotein were used for immunization, animals were protected upon challenge with the pathogenic agent. However, post-immunization complications are documented concerning the use of vaccinia virus as a vaccine. One such concern involves the propensity of vaccinia virus to induce hyperplastic responses and even tumors in the skin of infected subjects.

The vaccinia virus growth factor (VGF) is thought to play a role in these complications. The VGF is a homologue of epidermal growth factor (EGF) and of transforming growth factor α. Blomquist, et al., *Proc. Natl. Acad. Sci. USA*, 81:7363-7367 (1984). Vaccinia virus growth factor that has been post-translationally modified is capable of binding to the EGF receptor, stimulating autophosphorylation and inducing anchorage-independent cell growth.

To investigate the role of this gene product on infectivity and viral yields, both copies of the VGF gene were deleted from a recombinant vaccinia virus. In tissue culture cells there was little or no difference in infectivity or yield between the wild-type and mutant viruses. Buller, et al., *J. Virol.* 62:866-874 (1988). In vivo experiments revealed, however, that infection with wild-type virus resulted in a rapid proliferation of extodermal and entodermal cells of the chicken embryo chorioallantoic membrane, whereas this did not occur to the same extent with the VGF double mutant. Buller, et al., *Virology,* 164:182-192 (1988). However, there was double mutant viral reproduction in these experiments.

Another line of research examined the role of the thymidine kinase (TK) gene in vaccinia virus reproduction. It is known that the TK gene enhances herpesvirus replication in non-dividing cells. Kiemperer, et al., *Virology* 31:120-128 (1967). To determine whether inactivation of the vaccinia virus TK gene by the insertion of foreign DNA led to attenuation, Buller, et al., examined several TK− recombinants for their ability to replicate. Buller, et al., *Nature* 317:813-815 (1985). Although reduced viral mediated pathogenesis was observed with these mutants, the TK− viruses retained the ability to replicate in non-dividing cells.

Although the vaccinia virus has been the subject of considerable research to date, there remains a need for a vaccinia virus expression vector that substantially fails to replicate in non-dividing cells.

BRIEF DESCRIPTION OF THE DRAWINGS

FIG. 1A depicts viral expansion in non-confluent NIH3T3 cells. FIG. 1B depicts viral expansion in confluent NIH3T3 cells.

DETAILED DESCRIPTION OF THE PREFERRED EMBODIMENT

Figure 1:
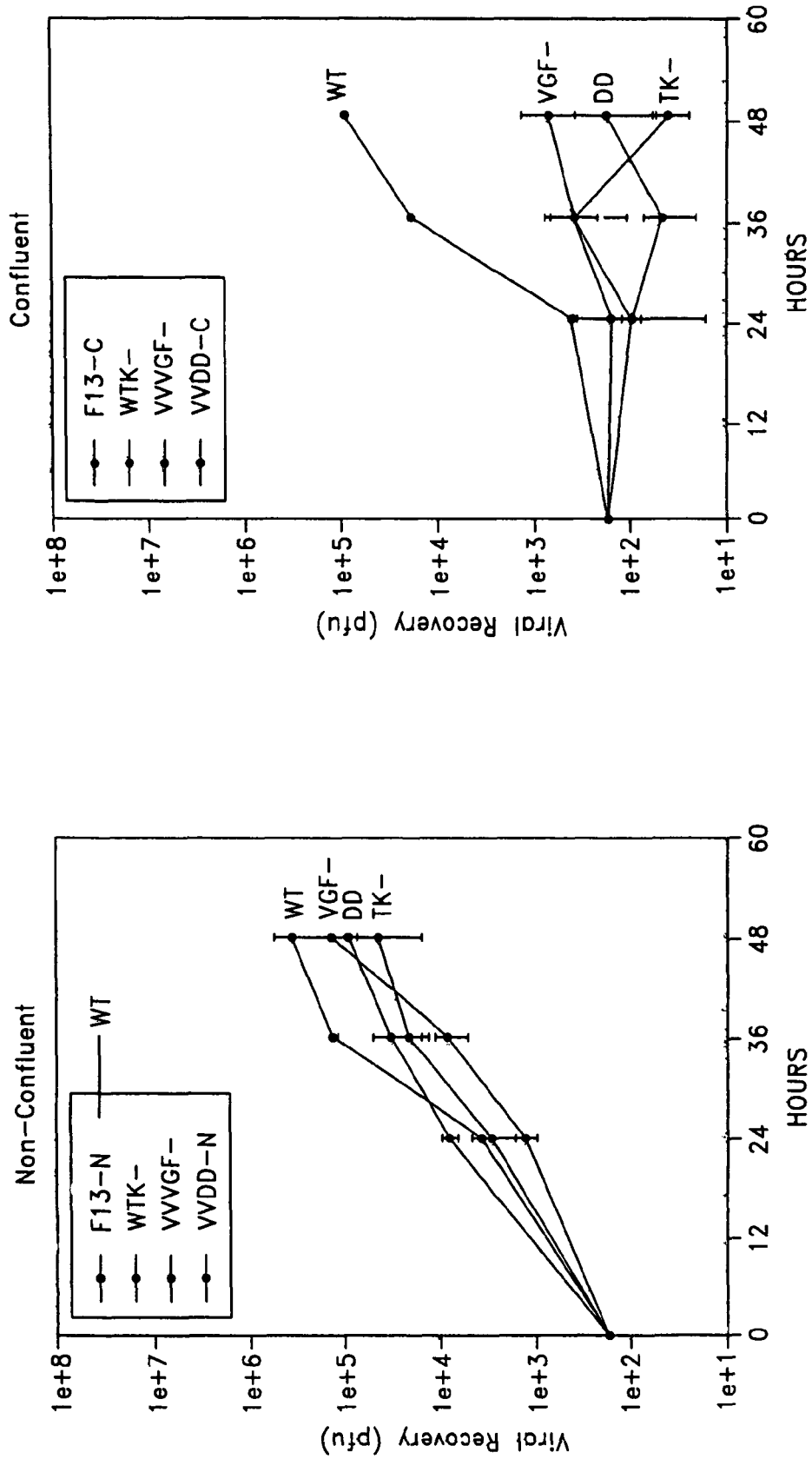
FIG. 1 depicts viral expansion in NIH3T3 cells of wild-type (F13), VGF− phenotype vaccinia virus VVVGF− (VSC20), TK− phenotype vaccinia virus VVTK− (VJS6), and the VGF−/TK− double mutant vaccinia virus VVDD.

The present invention relates to poxvirus expression vectors that are associated with TK and VGF negative phenotypes. The vectors of the present invention are substantially incapable of replicating in non-dividing cells. Substantially incapable of replication means a vaccinia virus that replicates 90% as well as the wild-type virus, or 80% as well, or 70% as well, or 60% as well, or 50% as well, or 40% as well, or 30% as well, or 20% as well, or 10% as well, or 1% as well, or any percent within this described field. More specifically, the present invention relates to vaccinia virus expression vectors that are associated with TK and VGF negative phenotypes. The present invention also relates to methods of making the vaccinia virus discussed herein, as well as to methods of using these expression vectors.

The expression vectors of the present invention are constructed from members of Poxviridae that possess a thymidine kinase phenotype and a virus associated growth factor phenotype. Expression vectors from the subfamilies Chordopoxvirinae and Entomopoxvirinae are encompassed by the present invention. Specifically, virus that are members of the genera *Orthopoxvirus, Parapoxvirus, Avipoxvirus, Capripoxvirus, Leporipoxvirus, Suipoxvirus, Molluscipoxvirus, Yatapoxvirus, Entomopoxvirus A, Entomopoxvirus B*, and *Entomopoxvirus C* are contemplated for use with the methods of the present invention. Specific examples of viruses that may be used with the methods of the present invention include: camelpox, cowpox, ectromelia, monkeypox, racoonpox, skunkpox, taterapox, Uasin Gishu, variola, volepox, Auzdyk disease, chamois contagious ecthyma, orf, pseudocowpox, parapox of deer, sealpox, carnarypox, fowlpox, juncopox, mynahpox, pigeonpox, psittachinepox, quailpox, peacockpox, penguinpox, sparrowpox, quailpox, sparrowpox, starlingpox, turkeypox, goatpox, lumpy skin disease, sheeppox, hare fibroma, myxoma, rabbit fibroma, squirrel fibroma, swinepox, molluscum contagiosum, tanapox, Yaba monkey tumor, *Melolonltha melolonltha, Amesacta moorei*, and *Chironimus luridus*. In a preferred embodiment, vaccinia virus is used as the expression vector.

There are a number of vaccinia virus strains presently known. Each of these strains can be used with the methods of the present invention. These strains include the WR strain (ATCC VR-119), the Wyeth strain (ATCC VR-325), the Lederle-Chorioallantoic strain (ATCC VR-325), the CL strain (ATCC VR-117), and others; all of these strains are available from the American Type Culture Collection (Manassas, Va.).

Vaccinia virus was introduced in 1982 as a vector for transient expression of genes in mammalian cells (Mackett et al., 1982). As a vector, vaccinia virus has a number of useful characteristics, including a capability that permits cloning large fragments of foreign DNA (>20 kbp) with retention of infectivity, a wide host range, a relatively high level of protein synthesis, and transport, secretion, processing, and posttranslational modifications as dictated by the primary structure of the expressed protein and the cell type used. For example, N- and O-glycosylation, phosphorylation, myristylation, and cleavage, as well as assembly of expressed proteins, occur in an apparently faithful manner.

Applications of vaccinia virus expression vectors are numerous. In in vitro applications, recombinant vaccinia virus expression vectors have utility in the production of biologically active proteins in tissue culture, analysis of mutant forms of proteins, and determination of transport and processing signals. In addition, recombinant vaccinia viruses have been important for immunological studies. (Bennink and Yewdell, *Curr Top Microbiol Immunol* 163:153-84 (1990)). In in vivo applications, recombinant vaccinia virus expression vectors have utility as vaccines and gene delivery vectors for human and veterinary uses.

Although the vaccinia virus has a number of potential uses, the virus also has a number of limitations that reduce its utility. For example, the virus itself is a human pathogen that can cause death in certain immune compromised individuals with defective cell-mediated immunity. Malaise, pustule formation, progressive vaccinia, and encephalitis are also known complications of vaccinia virus infection. Furthermore, accidental infection of individuals, especially children, who come into contact with an individual infected with the vaccinia virus is also a significant complication. This phenomenon is known as eczema vaccinatum, which occurs in eczematous subjects. Large areas of skin can be infected. Eczema vaccinatum is rarely fatal, but all cases require treatment. In view of these limitations, a vaccinia virus vector with a diminished capability to replicate in non-dividing cells would be extremely useful.

The present invention describes mutant vaccinia viruses that are substantially incapable of replicating in non-dividing cells. This inability arises from a combination of mutations in viral genes that result in a mutant virus that is substantially incapable of replication in non-dividing cells. This reduced capability can be achieved by mutating various viral genes including the ribonucleotide reductase-large subunit, the ribonucleotide reductase-small subunit, thymidylate kinase, DNA ligase, dUTPase, the thymidine kinase (TK) gene, and the vaccinia virus growth factor (VGF) gene. In a preferred embodiment, double mutations in the TK and VGF genes result in a virus with a TK– and VGF– phenotype.

It is one of the surprising observations of the present invention that the combination of TK and VGF minus phenotypes yield a vaccinia virus with a diminished ability to replicate in non-dividing cells, especially in vivo. That is, it replicates selectively in dividing cells. The teachings described below instruct how to make and use the mutant vaccinia viruses of the present invention.

The vaccinia virus TK gene is present in one copy in the vaccinia virus genome. To create a vaccinia virus with a TK– phenotype, it is necessary to disrupt the nucleic acid sequence of the TK gene in such a way that the TK gene no longer encodes an active and functional copy of the TK gene. Disruption of the TK gene can be achieved through an insertion, an amino acid sequence altering substitution of the existing nucleic acid sequence, or a deletion in the nucleic acid sequence of the gene. Alternatively, the entire gene sequence can be removed from the vaccinia virus genome so that all or most of the TK gene sequence is absent from the resulting recombinant vaccinia virus genome. The molecular biology techniques required to facilitate these changes are found, for example, in Current Techniques in Molecular Biology, (Ed. Ausubel, et al.) (1998).

A vaccinia virus with a negative VGF phenotype can be made in a manner similar to that described for the TK gene. For example, one or both of the VGF genes can be inactivated using standard molecular biology techniques that either create an insertion, a substitution, or a deletion of a portion, or of the entire VGF gene. Preferably, both copies of the VGF genes are inactivated. The end result of whatever procedure chosen to create the mutants described above is the production of a vaccinia virus with a negative TK and VGF phenotype.

Standard techniques in molecular biology can be used to generate the TK and VGF genotypes that result in TK and VGF negative phenotypes. Molecular biology techniques contemplated for use with the present invention include various nucleic acid manipulation techniques, nucleic acid transfer protocols, nucleic acid amplification protocols, and other molecular biology techniques. For example, point mutations are often introduced into a gene of interest through the use of oligonucleotide mediated site-directed mutagenesis. Alternatively, homologous recombination can be used to introduce exogenous sequence into a target sequence of interest. Nucleic acid transfer protocols include calcium chloride tranformation/transfection, electroporation, liposome mediated nucleic acid transfer, N-[1-(2,3-Dioloyloxy)propyl]-N,N,N-trimethylammonium methylsulfate meditated transformation, and others. In an alternative mutagenesis protocol, point mutations in a particular gene can also be selected for using a positive selection pressure. See Current Techniques in Molecular Biology, (Ed. Ausubel, et al.) Unit 16.17.9 to 16.17.19 (1998). Nucleic acid amplification protocols include but are not limited to the polymerase chain reaction (PCR).

Once the double mutant recombinant vaccinia virus is constructed, it must be tested for negative TK and VGF phenotypes. The presence of a positive phenotype for either of these genes can negatively effect the utility of the virus as a vector. A negative phenotype for either of these genes and their respective gene products is a state wherein the gene products of these genes are present in such low quantities that substantially no replicative advantage compared to the wild-type virus is conveyed to the mutant vaccinia virus encoding these genes. Accordingly, a negative phenotype for one or both of these genes would include a mutant vaccinia virus that produce such low levels of the products of these gene that substantially no viral replication occurs in non-dividing cells.

An assay that is capable of determining whether or not a functional TK or VGF protein is produced by a putatively recombinant vaccinia virus can be used with the methods of the present invention. For example, to determine the presence or absence of a VGF− phenotype, a putatively recombinant vaccinia virus is produced according to the methods of the present invention and tested for its ability to produce a functional VGF protein. Such assays include determining the presence of the VGF protein by examining VGF biological activity, by immunological techniques, or by molecular biology techniques such as PCR and gene sequencing to determine the presence of a gene and its sequence, and other methods well known in the art. For example, VGF protein activity can be measured by performing EGF-receptor competition binding assays, by measuring the amount of tyrosine phosphorylation of EGF receptors as a result of VGF binding, or by observing changes in signal transduction following binding to EGF receptors. The presence or absence of TK− phenotype is assayed for by examining TK enzymatic activity, by immunological techniques, by molecular biology techniques, or other methods well known in the art. For example, cells infected with a putative TK− vaccinia virus are capable of growth in the presence of 5-bromodeoxyuridine (BrdU), a nucleotide analog that incorporates into DNA in the presence of a functional TK gene. In contrast, cells infected with TK+ phenotype virus are not capable of growth in the presence of BrdU.

Following construction of the double mutant vaccinia virus vector, a gene of interest can be placed under the control of a vaccinia virus promoter and integrated into the genome of the mutant vaccinia virus. Alternatively, expression can be achieved by transfecting a shuttle vector or plasmid containing the vaccinia promoter-controlled gene into a cell that has been infected with vaccinia virus and introducing the exogenous sequence by homologous recombination. In still another variation, the bacteriophage T7 RNA polymerase gene can be integrated into the genome of vaccinia so that a gene controlled by a T7 promoter, either in a transfected plasmid or a recombinant vaccinia virus, is expressed.

There exist a number of vaccinia virus shuttle vectors that contain vaccinia virus promoters. These shuttle vectors are appropriate means to introduce by homologous recombination exogenous nucleotide sequences into the vaccinia virus genome for expression purposes. Such nucleotide sequences can also be introduced to "knock out" or inactivate the TK and/or VGF sequences. A table of such vectors is found in TABLE 1, which was taken from Current Techniques in Molecular Biology, (Ed. Ausubel, et al.) Unit 16.17.4 (1998).

TABLE 1

Vaccinia Virus Transfer Vectors

| Vector[a] | Promoter[b] | Cloning sites[c] | Insertion sites[d] | Selection/ screening | Reference[f] |
|---|---|---|---|---|---|
| PGS20 | $p_{7.5}$(E/L) | BamHI; SmaI | TK | TK- | Mackett et al., 1984 |
| PSC11 | $p_{7.5}$(E/L) | SmaI; MCS | TK | TK-, β-gal | Chakrabarti et al., 1985; Earl et al, 1990; Bacik et al., 1994 |
| PMJ601, pMJ602 | $p_{syn}$ (L) | MCS | TK | TK-, β-gal | Davison and Moss, 1990 |
| PRB21 | $p_{syn}$ (E/L) | MCS | F12L/F13L | Plaque | Blasco and Moss, 1995 |
| PMC02 | $p_{syn}$ (E/L) | MSC | TK | TK-, GUS | Carroll and Moss, 1995 |
| PSC59 | $p_{syn}$ (E/L) | MCS | TK | TK- | Chakrabarti et al., 1997 |
| PSC65 | $p_{syn}$ (E/L) | MCS | TK | TK-, β-gal | Chakrabarti et al., 1997 |
| PJS4 | $p_{syn}$ (E/L) x2 | MCS | TK | TK- | Chakrabarti et al., 1997 |
| PJS5 | $p_{syn}$ (E/L) x2 | MCS | TK | TK-, gpt | Chakrabarti et al., 1997 |
| PG06 | $p_{syn}$ (E/L) x2 | MCS | Del III | Transient gpt[e] | Sutter et al., 1994 |
| PLW-7 | $p_{syn}$ (E/L) | MCS | Del III | Transient gpt[e] | Wyatt et al., 1996 |
| PMC03 | $p_{syn}$ (E/L) | MCS | Del III | GUS | Carroll and Moss, 1995 |
| PLW-9 | $p_{H5}$ (E/L) | MCS | Del III | Transient gpt[e] | Wyatt et al., 1996 |
| PLW-17 | $p_{H5}$ (E/L) | MCS | Del II | None | L. Wyatt and B. Moss, unpub. Observ. |
| PLW-21 | $p_{syn}$ (E/L) | MCS | Del II | None | L. Wyatt and B. Moss, unpub. Observ. |

TABLE 1-continued Vaccinia Virus Transfer Vectors

| Vector[a] | Promoter[b] | Cloning sites[c] | Insertion sites[d] | Selection/screening | Reference[f] |
|---|---|---|---|---|---|
| PLW-22 | $p_{syn}$ (E/L) | MCS | Del II | β-gal | L. Wyatt and B. Moss, unpub. Observ. |
| PLW-24 | $p_{7.5}$ (E/L) | MCS | Del II | None | L. Wyatt and B. Moss, unpub. Observ. |

[a]pRB21 was specifically designed for use with vaccinia virus vRB12, which has a deletion in the F13L gene. The plasmids pG06, pLW-7, pMC03, pLW-9, pLW-17, pLW-21, pLW-22, and pLW-24 were designed for MVA.
[b]Abbreviations: E, early; L, late; E/L, early and late. The designation "x2" refers to two oppositely oriented promoters that can be used for expression of two genes.
[c]SmaI digestion gives a blunt end for cloning any fragment that has been blunt-ended. MCS signifies multiple cloning sites.
[d]Abbreviations: TK, thymidine kinase locus; F12L/F13L, between F12L and F13L open reading frames; Del III, site of natural deletion in MVA.
[e]Transient selection in which DXGPRT gene is deleted from recombinant vaccinia virus during recombination; see Background Information.
[f]Chakrabarti et al., 1997 Biotechniques 23: 1094-1097; Sutter et al., 1994 Vaccine 12: 1032-1040; Wyatt et al., 1996 Vaccine 14: 1451-1458; Carroll and Moss 1995 BioTechniques 19: 352-355.

The vaccinia virus expression vector of the present invention has utility for facilitating the expression of a broad number of exogenous nucleotide sequences. Genes, cDNAs encoding open reading frames derived from prokaryotic, eukaryotic, or viral sources other than vaccinia virus have been expressed using vaccinia virus vectors. The gene of interest is usually placed next to a vaccinia promoter and this expression cassette is then inserted into the virus genome by homologous recombination or direct ligation. Use of poxvirus promoters can be important since cellular and other viral promoters are not recognized by the vaccinia transcriptional apparatus. Strong late promoters are preferable when high levels of expression are desired. Early and intermediate-stage promoters, however, can also be used. The most versatile and widely used promoters contain early and late promoter elements. A list of suitable promoters appears in TABLE 1.

A number of plasmids are available with restriction endonuclease sites for insertion of foreign genes downstream of vaccinia promoters. The expression cassette is generally flanked by vaccinia DNA to permit homologous recombination when the plasmid is transfected into cells that have been infected with a vaccinia virus. The flanking vaccinia virus DNA is chosen so that recombination will not interrupt an essential viral gene. The shuttle vectors listed in TABLE 1 each have a multiple cloning site (MCS) to facilitate the insertion of exogenous nucleotide sequences.

In one embodiment, the vaccinia virus vectors of the present invention are contemplated for use as expression vectors in vitro and in vivo. Whole genes, open reading frames (ORFs), and other exogenous nucleotide fragments, such as nucleic acid sequences to generate antisense products, are contemplated for expression using the vaccinia virus vectors of the present invention.

Classes of genes contemplated for expression with the vectors of the present invention include tumor suppressor genes, cytotoxic genes, cytostatic genes, cytokines, and antigen encoding genes. Examples of tumor suppressor genes include: WT1, p53, p16, Rb, BRCA1, and others. Genes with therapeutic or scientific applications include: cystic fibrosis transmembrane regulator (CFTR), Factor VIII, low density lipoprotein receptor, beta-galactosidase, alpha-galactosidase, beta-glucocerebrosidase, insulin, parathyroid hormone, alpha-1-antitrypsin, and the like.

An additional class of genes for use with the vectors of the present invention are suicide genes. Suicide genes are genes that are involved in the process of programmed cell death or apoptosis. Genes with this function include: herpes simplex virus thymidine kinase, varicella thymidine kinase, cytosine deaminase, purine nucleoside phosphorylase, β-lactamase, carboxypeptidase G2, cytochrome P450-2B1, nitroreductase, β-glucuronidase, and others. These genes, inserted into target cells, provide an excellent method by which to sensitize cells to certain chemotherapeutic agents. The double mutant vaccinia virus expression vectors of the present invention are an excellent method for introducing these genes into dividing target cells.

The prototypical suicide gene system is the Herpes simplex virus thymidine kinase type 1 (HSV-TK)/Gancyclovir (GCV) system. HSV-TK phosphorylates nucleoside analogs (gancyclovir/acyclovir) into their monophosphate and triphosphate forms, which are incorporated into DNA during cell division, leading to cell death. Moolton et al first demonstrated in 1986 that transfection of the HSV-TK gene into sarcoma cells rendered them sensitive to the cytotoxic effects of GCV. Moolten, *Cancer Res* 46:5276-81 (1986). Since that time numerous studies have demonstrated the efficacy of the system. Many strategies for delivering the HSV-TK gene have been employed including liposomal transfections, retroviral transductions, and adenoviral infections. The vaccinia virus expression vectors of the present invention represent an additional method of delivering this gene. One advantage of this system is that only dividing cells are affected so systemic toxicity is minimal. Another advantage is that GCV has been shown to be safe in humans and is readily available.

In vitro treatment of glioma cells with a non-replicating adenovirus carrying HSV-TK was cytotoxic to cells in the presence of GCV at multiplicities of infection (MOI) above 150. Smythe et al demonstrated that 10-20% of mesothelioma cells expressing the HSV-TK gene were able to sensitize 70 to 80% of cells to GCV indicating a fairly significant bystander effect in these cells. Smythe et al, *Cancer Res* 54:2055-9 (1994). Although GCV triphosphate is unable to freely diffuse across the cell membrane, a variable bystander effect is seen. Several investigators have studied this phenomenon because a strong bystander effect is thought to be essential in vivo when tumor cell transduction is inefficient. The in vitro bystander effect for the HSV-TK system is thought to be mediated by gap junctions which allow transport of GCV triphosphate between cells. The observation that cell lines with relatively few gap junctions had minimal bystander effects led to the upregulation of a gap junction protein (connexin) in a glioma cell line which increased the bystander effect in vitro and in vivo.

Several in vivo studies have demonstrated the potential therapeutic utility of this system. Subcutaneous sarcomas in BALB/c mice, retrovirally transduced with the HSV-TK gene, demonstrated a complete response after treatment with intraperitoneal (IP) GCV. Hepatic metastases transduced in vivo with a retrovirus expressing HSV-TK, were treated with twice daily injection of GCV for 5 days. This led to a significant inhibition of tumor growth compared to controls, with some complete regressions. Non-replicating, recombinant adenovirus carrying the HSV-TK gene has been used in many tumor models. Mice with intracerebral gliomas were injected intratumorally with adenovirus carrying HSV-TK, and then received IP GCV twice daily for 6 days. This resulted in a 23-fold decrease in tumor size compared to controls, and 2 complete regressions. There was no toxicity to the surrounding normal brain. Similar adenoviral/HSV-TK/GCV systems have effectively treated experimental ovarian cancer, head and neck cancer, breast cancer and melanoma. No systemic toxicity from the converted prodrug has been demonstrated.

The varicella thymidine kinase gene is another suicide gene contemplated for use with the present invention. Varicella zoster (VZV) is another virus in the Herpesviridae family, whose TK gene shares 28% homology with the HSV-TK and has a different substrate specificity. Several prodrugs have been tested for activity in a suicide gene system using VZV-TK, including GCV, acyclovir, (E)-5-(2-bromovinyl)-2'-deoxyuridine (BVDU), and others.

Breast cancer cells retrovirally transfected with VZV-TK, or controls, were treated with GCV, acyclovir, or BVDU. In the non-transduced controls there was minimal toxicity due to the prodrugs. In the transduced cell lines there was minimally increased sensitivity to GCV or acyclovir, but extreme sensitivity to BVDU (400 to 2000-fold over the parental cells). 50% of glial cells were needed to express the VZV-TK in order to see a global cytotoxic effect. The bystander effect was dependent on the cell line tested rather than the VZV-TK/BVDU system itself and may be a reflection of the number of intercellular gap junctions similar to the HSV-TK system.

Subcutaneously injected cells expressing the VZV-TK gene were similarly sensitive to BVDU. Significant, dose dependent, growth inhibition was seen after 8 daily IP injections of BVDU though no complete regressions were seen. There was no systemic toxicity from the converted prodrug.

Another suicide gene is cytosine deaminase (CD), which is a bacterial enzyme that deaminates cytosine to uracil and 5-fluorocytosine (5-FC) to 5-fluorouracil (5-FU). As it is not normally present in mammalian cells, the CD gene is useful in suicide gene systems. Transfer of the CD gene to mammalian tumor cells allows local conversion of 5-FC into 5-FU, which inhibits both RNA and DNA synthesis and leads to cell death. 5-FU is an effective chemotherapy agent and it has selectivity for dividing cells. It is standard therapy for various gastrointestinal and breast cancers. The prodrug 5-FC is well tolerated by humans and has been used in antifungal therapy.

Several methods to selectively transfer the CD gene to tumor cells have been employed including plasmid transfections, retroviral transduction, adenoviral infection, vaccinia infection and antibody-conjugates.

In vitro studies have demonstrated the ability to sensitize tumor cells to 5-FC by expression of the CD gene. The ability of 5-FU to diffuse through the cell membrane makes this an attractive system because of the bystander effect. When 20% of the cells expressed the CD gene, 60 to 80% cytotoxicity was seen after 4 days. The detection of 5-FU in the supernatants of CD-transduced cells suggests that direct cell to cell contact (such as in the TK systems) is not needed for a bystander effect.

Subcutaneous tumors, retrovirally transduced with the CD gene, showed significant growth inhibition which was further improved with earlier treatment and higher doses of 5-FC. The use of viruses to deliver the CD gene to subcutaneous xenografts has also been successful with significant growth inhibition or tumor regression when injected intra-tumorally. Intra-hepatic or intravenous delivery of an adenovirus carrying the CD gene inhibited tumor growth after 5-FC administration with no systemic toxicity from the prodrug or its metabolites. Intravenous delivery of an antibody-CD conjugate followed by IP 5-FC, led to high tumor levels of 5-FU compared to other organs. This may be an additional method for achieving high tumor levels of 5-FU without systemic toxicity.

Purine nucleoside phosphorylase (PNP) is an enzyme involved in the purine salvage pathway. Both prokaryotic and eukaryotic enzymes exist, but utilize unique substrates. Only the Escherichia coli (E. coli) PNP can convert adenosine and adenosine analogs and has a 10-fold higher activity against purine arabinosides, allowing the system to be used in enzyme-prodrug therapy. The E. coli PNP converts the prodrug 6-methylpurine deoxyriboside (6MPDR) to the toxic metabolite 6-methylpurine (6-MP), which is highly toxic to tumor cells via inhibition of both RNA and protein synthesis. While this prodrug is well tolerated in animals, it has not been used in humans. Fludarabine is another substrate for this enzyme, which has been used in humans for the treatment of hematologic malignancies and is associated with systemic toxicity at high doses.

In vitro studies have shown >90% cytotoxicity in multiple cell types by day 5 after PNP gene transfer. These studies highlight several advantages of the PNP system. First, the conversion from 6-MPDR to 6-MP is very efficient with minimal measurable prodrug in cell supernatants by day 3. Secondly, because 6-MP inhibits both RNA and protein synthesis, it does not require cell proliferation to have an effect. Thirdly, 6-MP is freely diffusible across cell membranes leading to a strong bystander effect. Complete cytotoxicity was seen in vitro when as little as 2% of cells expressed the PNP gene illustrating the potency of the system.

In vivo studies have shown efficacy of this system in nude mice. It has been shown that significant regression of subcutaneous tumors can be retrovirally transduced by the expression of the PNP gene, when cells are treated with 6-MPDR for 3 days. In addition, no toxicity due to systemic 6-MP was seen for this dosing regimen. Puhlmann, et al., Hum Gene Ther 10:649-57 (1999). Puhlmann et al showed efficacy in a hepatic metastases model using a replicating vaccinia virus to deliver the PNP gene. Nude mice with hepatic metastases were treated with IP vaccinia virus carrying the PNP gene, followed by either weekly or every other daily injections of 6-MPDR. Both groups had a significant prolongation of survival with a 30% and 50% cure rate respectively. No evidence of toxicity from the converted prodrug was seen with this dosing regimen, but significant hepatic toxicity was seen at higher doses, presumably due to the potency and diffusability of 6-MP. This system is ultimately limited by systemic toxicity of the converted prodrug, requiring careful prodrug dosing.

β-lactamase is a bacterial enzyme that confers resistance to β-lactain antibiotics by cleavage of the amide bond in the β-lactam ring. The synthesis of nontoxic prodrugs, consisting of cephalosporins conjugated to chemotherapy agents, has allowed the system to be used for suicide gene therapy as the conjugated prodrug is similarly cleaved releasing active drug. Several prodrugs have been synthesized for this system including cephalosporin-doxorubicin (C-Dox), 7-(4-carboxybutanamido)-cephalosporin mustard (CCM), cephalosporin-mitomycin C, cephalosporin-paclitaxel, and cephalosporin-carboplatinum. Tumor-specific antibodies conjugated to the β-lactamase enzyme have allowed for tumor-targeted activation of the various prodrugs.

In vitro studies showed that treatment of melanoma cells with an antibody-β-lactamase conjugate followed by the prodrugs C-Dox and CCM, led to a 4 and 30-fold increase respectively, in the sensitivity of cells to the prodrugs although some nonspecific prodrug toxicity was seen. Subcutaneous melanoma xenografts in nude mice treated weekly with antibody-β-lactamase and C-Dox showed tumor regression which eventually progressed. In contrast, similar treatments using CCM led to complete long-term regression in 80% of the mice. Although some neurologic toxicity was seen with the C-Dox, there was no systemic toxicity from the CCM. Similar studies using antibody-β-lactamase/C-Dox to treat xenografts of breast carcinoma cells and colon carcinoma cells showed tumor growth inhibition in both histologies with minimal toxicity, although no complete regressions were seen. Finally, nude mice with subcutaneous melanoma xenografts were treated using a single-chain antibody/β-lactamnase fusion protein in combination with CCM. Complete tumor regressions, in the majority of animals treated with CCM 12 hours after delivery of the fusion protein, were seen with no evidence of systemic toxicity. While this system has not been studied in a gene delivery approach, the β-lactamnase protein is extremely versatile and should be functional in this context. Accordingly, this gene may provide an excellent means by which to kill cells infected with the double mutant vaccinia virus of the present invention expressing this gene.

Carboxypeptidase G2 (CPG2) is a bacterial enzyme that catalyzes the hydrolytic cleavage of folates and methotrexate to pteroates and L-glutamic acid. Similar cleavage releases active alkylating agents from prodrugs synthesized with a glutamic acid group blocking the enzyme's function. Various methods of tumor specific expression of CPG2 have been studied including antibody targeting and stable transfection, suggesting it would be a good enzyme for use in a suicide gene system.

Stable transfection of colon and ovarian carcinoma cell lines with CPG2 resulted in a 16 to 95-fold increase in sensitivity to the prodrug 4-[(2-chloroethyl)(2-mesyloxyethyl)amino]benzoyl-L-glutamic acid (CMDA). 100% cytotoxicity was seen when 3.7 to 12% of the cells expressed CPG2. In vivo studies have used tumor specific monoclonal antibodies conjugated to CPG2 as a means of enzyme delivery. A nude mouse model of human choriocarcinoma showed significantly increased survival when treated with anti-human chorionic gonadotrophin (HCG) antibody/CPG2 conjugates, followed by only 3 doses of prodrug 72 hours later. Subcutaneous colon carcinoma xenografts had significant growth delay when treated with antibody/CPG2 conjugate followed by prodrug, although the tumors subsequently regrew. Minimal toxicity to the prodrug and its metabolites was seen.

Cytochrome P450-2B1 (CYP2B1) is a naturally occurring liver enzyme necessary in the conversion of cyclophosphamide and ifosfamide to their 4-hydroxy derivatives. These metabolites are unstable and further degrade to become the toxic metabolites acrolein and phosphoramide mustard, which cause protein and DNA alkylation respectively. Because tumor levels of the enzyme are low, these chemotherapeutic agents are normally metabolized in the liver, leading to systemic toxicity prior to a maximal tumor response. Use in a suicide gene system allows upregulation of CYP2B1 expression in tumor cells, leading to local conversion of cyclophosphamide and ifosfamide, and potentially less systemic toxicity. This system is appealing because it may enhance the effect of agents which have already shown to be effective in cancer therapy and for which a safety profile has already been defined.

In vitro studies demonstrated that glioma cells and breast cancer cells, stably transfected with the CYP2B1 gene, acquired sensitivity to cyclophosphamide and ifosfamide. This sensitivity was blocked by the CYP2B1 inhibitor metyrapone. A significant bystander effect was seen when 20-50% of the cells expressed the CYP2B1 gene, and this persisted in co-culture experiments suggesting that direct cell contact is not needed for this effect.

Several studies have shown enhanced sensitivity of subcutaneous tumors (glioma-breast cancer) retrovirally transduced with CYP2B1 (ex vivo) to cyclophosphamide. In one study, this led to complete inhibition of tumors in 95% of animals after a single IP injection of cyclophosphamide. Inoculation of retroviral producer cells or replication deficient adenovirus expressing the CYP2B1 gene into intracerebral gliomas led to prolonged survival after 1 dose of IP cyclophosphamide. There was no notable toxicity from the cyclophosphamide conversion at the doses studied.

Finally, Chase et al (1998) were able to show that intratumoral injection of a CYP2B1 expressing herpes simplex virus and cyclophosphamide, had an enhanced oncolytic effect compared to the virus alone. Chase M, et al., Nature Biotech 16:444-8 (1998).

Another interesting suicide gene is nitroreductase. Initial studies of the alkylating agent CB1954 showed promise in a rat Walker tumor model, however human trials were disappointing. Subsequently it was shown that the human equivalent of rat DT diaphorase, was inefficient at converting CB1954 to its active metabolite, the 4-hydroxylamino derivative which causes DNA crosslinking and cell death. The identification of a bacterial enzyme with similar activity, *E. coli* nitroreductase (ntr), led to its use in suicide gene systems, where tumor-specific expression of the bacterial enzyme would render tumor cells uniquely sensitive to CB1954.

In vitro studies have shown a 10 to 100-fold increase in sensitivity of pancreatic, colonic, and mammary cell tumor lines to CB1954 when transfected with plasmids expressing the ntr gene. Retroviral transduction led to a 17 to 500-fold increase insensitivity to CB1594, which correlated with the amount of nitroreductase produced by the cells. Cell mixing experiments demonstrated a significant in vitro bystander effect if 30% of the cells express the gene. Transgenic mice engineered to express a CD2/ntr transgene in T cells and thymocytes had much smaller spleens and thymuses, and a significantly increased level of apoptosis in these organs, 5 days after treatment with CB1954. Clark et al (1997) showed that transgenic mice expressing ntr under the control of the β-lactoglobin promoter, had increased levels of ntr mRNA and protein in mammary glands compared to other tissues, and treatment with CB1954 resulted in disrupted mammary glands with increased apoptosis. Clark et al., Gene Ther. 4:101-10 (1997). Nonspecific toxicity from the prodrug or converted active drug was not seen.

Traditionally the *E. coli* xanthine-guanine phosphoribosyl transferase (gpt) gene has been used for positive selection in a purine salvage pathway as it catalyzes the conversion of xanthine, hypoxanthine and guanine to their respective monophosphates. Cells which express the gpt gene can utilize xanthine as a purine analog in the presence of mycophenolic acid and hypoxanthine which inhibit the mammalian pathway. Conversely, gpt has recently been used to selectively sensitize tumor cells to 6-thioxanthine (6-TX) as it is incorporated into this purine synthesis pathway. Mroz and Moolton showed that retrovirally transducing the gpt gene into sarcoma cells conferred an 86-fold increased sensitivity to 6-TX. Human Gene Therapy 1993; 4:589-95. Tamiya et al showed that glioma cells were sensitive to 6-TX at an LD50 of 2.5 umol/L when transduced with gpt. Cancer Gene Therapy 1996; 3:155-62 Untransfected cells were minimally sensitive at 50 umol/L. As well, a significant bystander effect (75% cytotoxicity) was seen when 10% of the cells expressed gpt. This effect was abrogated when the cells were separated suggesting that cell to cell contact was required. Syngeneic Balb/C mice injected subcutaneously with a transduced sarcoma cell line showed complete regression in 95% of the animals after 5 days of treatment with 6-TX. A 10% treatment mortality due to toxicity of the converted prodrug was seen and was eradicated with an alternate day dosing schedule. Nude mice subcutaneously injected with transduced glioma cells showed a significant inhibition of tumor growth when treated with IP 6-TX for 10 days at a reduced dose, with no treatment toxicity. In the same study, nude mice with transduced intracerebral gliomas showed prolonged survival after 6-TX treatment. In another study similar subcutaneous tumor inhibition was seen, and regrowth was correlated with loss of the retrovirally expressed gpt gene after 3 weeks. In this study, survival after intracerebral tumor injection was prolonged by 6-TX, in the presence of the gpt gene. Pathological evaluation of these brains did not show any neurotoxicity from the 6-TX treatment.

β-glucuronidase (GUS) is a glycosidase normally present in low amounts in normal human tissues and slightly higher levels in tumor tissues. GUS hydrolyses inactive glucuronide-conjugates into active drugs Several glucuronide prodrugs have been described for use in a GUS suicide gene system including conjugates of epirubicin, danorubicin, p-hydroxyaniline mustard and doxorubicin. While these prodrugs are nontoxic in animals, they have not been used in humans.

GUS has been conjugated to monoclonal antibodies to increase tumor-specific expression. Haisma et al used the anti-pan carcinoma antibody (323/A3) conjugated to GUS and demonstrated equivalent activity of the antibody-GUS/epirubicin-glucuronide to epirubicin alone in vitro, demonstrating activation of the prodrug. Br J Cancer 1999; 66:474-8. Similar effects were seen for the danorubicin prodrug. A single-chain antibody against the pan carcinoma antigen, conjugated to GUS was also effective against an ovarian cell line treated with a doxorubicin-glucuronide prodrug. In vivo treatment of a rat hepatoma model of ascites, with a hepatoma cell-specific antibody conjugated to GUS, resulted in long term cure of rats when treated with 3 IP injections of the p-hydroxyaniline glucuronide prodrug. Minimal toxicity of prodrug conversion was noted despite the presence of native GUS in some tissues.

Several other suicide gene systems have been recently described. Thymidine phosphorylase, which catalyzes the reversible phosphorolytic cleavage of thymidine, deoxyuridine and their analogs, has been used to convert the prodrug 5'-deoxy-5-fluorouridine to 5-FU. Cytosine arabinoside (ara-C) requires phosphorylation by deoxycytidine kinase (dCK) to form its active metabolite. Delivery of dCK to glioma cells sensitized them to treatment by ara-C. Overexpression of a rabbit carboxylesterase was shown to sensitize human cells to 7-ethyl-10-[4-(1-piperidino)-1-piperidino]-carbonyloxy-camptothecin (CPT-11) by its conversion to an active metabolite (SN38). Both β-glucosidase and the plant equivalent linamarase have been shown to hydrolyse amygdalin and linamarase respectively to cyanide. This leads to tumor specific toxicity when delivered via antibody-targeting or retroviral transduction, with no noted systemic toxicity.

Bovine carboxypeptidase A has been shown to cleave the amide bond of a methotrxate-phenylalanine prodrug, yielding free methotrexate. This enzyme was conjugated to a monoclonal antibody for tumor specific delivery, and in vitro studies showed that ovarian carcinoma cells became sensitive to the methotrexate-phenylalanine prodrug in the presence of carboxypeptidase A. Finally, a novel rabbit cytochrome P450 isoenzyme (CYP4B1) has been shown, to convert the prodrugs 2-aminoanthracene (2-AA) and 4-ipomeanol (4-IM) into toxic alkylating agents. Glioma cells stably transfected with CYP4B1 showed increased sensitivity to 2-AA and 4-IM in vitro and in vivo compared to control. A strong bystander effect was seen with 70 to 80% cytotoxicity when 1% of the cells expressed the CYP4B1 gene.

A table of certain suicide genes and drugs with activity associated with these genes is found at TABLE 2.

TABLE 2

Enzyme/Prodrug Systems

| ENZYME | PRODRUG | ACTIVE DRUG |
|---|---|---|
| Herpes Simplex Virus thymidine kinase | Gancyclovir | Gancyclovir triphosphate |
| Varicella Zoster Virus thymidine kinase | (E)-5-(2-bromovinyl)-2'-deoxyuridine (BVDU) | BVDU triphosphate |
| Cytosine deaminase | 5-fluorocytosine | 5-fluorouracil |
| Purine nucleoside phosphorylase | 6-methylpurine deoxyriboside | 6-methylpurine |
| β-lactamase | 7-(4-carboxybutanamido)-cephalosporin mustard | phenylenediamine mustard |
| Carboxypeptidase G2 | 4-[(2-chloroethyl)(2-mesyloxyethyl)amino]benzoyl-L-glutamic acid (CMDA) | 4-[(2-chlorocthyl)(2-mesyloxyethyl)amino]benzoic acid (CJS11) |
| Cytochrome P450-2B1 | Cyclophosphamide/ifosfamide | acrolein + phosphoramide mustard |
| E. coli nitroreductase | CB1954 (S-aziridin--yl-2-4-dinitrobenzamide) | 5-aziridin-1-yl-4-hydroxylamino-2-nitrobenzamide |
| Xanthine-guanine phosphoribosyl-transferase | 6-thioxanthine | 6-thioxanthine monophosphate |
| β-glucuronidase | epirubicin-glucoronide | Epirubicin |
| Thymidine phosphorylase | 5'-deoxy-5-fluorouridine | 5-fluorouracil |
| Deoxycytidine kinase | Cytosine arabinoside | Cytosine ababinoside monophosphate |
| Carboxylesterase | 7-ethyl-10-[4-(1-piperidino)-1-piperidino]carbonyl-oxycamptothecin (CPT-11) | 7-theyl-10-hydroxycamptothecin (SN-38) |
| Linamarase/β-glucosidase | Linamarin/Amygdalin | Cyanide |
| Carboxypeptidase A | Methotrexate-phenylalamine | Methotrexate |
| Cytochrome P450-4B1 | 2-aminoanthracene,4-ipomeanol | unknown alkylating agents |

The vaccinia virus expression vectors of the present invention are also contemplated for in vitro expression purposes. Any gene, ORF, or other segment of nucleic acid can be expressed in vitro using the expression vectors of present invention.

The present invention has utility in expressing genes in vivo and in vitro. Examples of genes expressable by the vaccinia virus expression vector of the present invention include expressing human genes. An exemplary list of genes includes the list of human genes and genetic disorders authored and edited by Dr. Victor A. McKusick and his colleagues at Johns Hopkins and elsewhere, and developed for the World Wide Web by NCBI, the National Center for Biotechnology Information. Online Mendelian Inheritance in Man, OMIM™. Center for Medical Genetics, Johns Hopkins University (Baltimore, Md.) and National Center for Biotechnology Information, National Library of Medicine (Bethesda, Md.), 1999. <<http://www.ncbi.nlm.nih.gov/omim/>>. These genes include: 239f2h9, 3pk, 4ebp1, 4ebp2, a11, a12m1, a12m2, a12m3, a12m4, a15, a1b, a1bg, a1st, a2m, a2mr, a2mrap, aa, aaa, aaa, aabt, aac1, aac2, aact, aadac, aanat, aars, aas, aat, aavs1, abc1, abc2, abc3, abc7, abc8, abcr, abi1, abl1, abl2, abll, abo, abp, abp1, abpa, abpx, abr, acaa, acac, acaca, acacb, acadl, acadm, acads, acadsb, acadvl, acat, acat1, acat2, acc, accb, accn1, accn2, accpn, ace1, ach, ache, achm1, achm2, achrb, achrd, achrg, acls, acly, aco1, aco2, acox, acox1, acox2, acox3, acp1, acp2, acp5, acpp, acr, acrv1, acs3, acs3, acs4, act2, act35, acta1, acta2, acta3, actb, actc, actg1, actg2, actl1, actn1, actn2, actn3, actsa, acug, acvr1, acvr2b, acvrl1, acvrlk1, acvrlk2, acvrlk3, acy1, ad1, ad2, ad3, ad4, ad5, ada, adam10, adam11, adam12, adam3, adam3a, adam3b, adam8, adar, adarb1, adarb2, adcp1, adcp2, adcy1, adcy2, adcy3, adcy3, adcy4, adcy5, adcy6, adcy7, adcy8, adcy9, adcyap1, adcyap1r1, add1, add2, add3, addl, adfn, adh1, adh2, adh3, adh4, adh5, adh7, adhaps, adhc1@, adhr, adhr, adk, adl, adm, adm1x, adora1, adora2a, adora2b, adora2l, adora2l1, adora3, adprt, adra1a, adra1b, adra1c, adra1d, adra2a, adra2b, adra2c, adra2l1, adra2l2, adra2r, adrb1, adrb1r, adrb2, adrb2rl1, adrb3, adrbk1, adrbk2, ads1, adss, adtb1, adx, adxr, ae1, ae2, ae3, aegl1, aemk, aes, af10, af17, af4, af6, af8t, af9, afd1, afdn, afg3, afg3l1, afm, afp, afx1, aga, agc1, ager, agl, agmx1, agmx2, agp1, agp7, agps, agrn, agrp, agrt, ags, agt, agtil, agtr1, agtr1a, agtr2, agtrl1, agxt, ahc, ahcy, ahd, ahds, ahnak, aho2, ahr, ahsg, ahx, aib1, aic, aicl, aied, aih1, aih2, aih3, aim1, air, airc, aire, ak1, ak2, ak3, akap149, akt1, akt2, aku, alad, alas1, alas2, alb, alb2, alba, alcam, ald, aldh1, aldh10, aldh2, aldh3, aldh4, aldh5, aldh6, aldh9, aldl1, aldoa, aldob, aldoc, aldr1, alds, alk, alk1, alk2, alk3, alk6, alms1, alox12, alox15, alox5, alp, alpi, alpl, alpp, alppl2, alr, alr, als1, als2, als4, als5, alss, ambn, ambp, amcd1, amcd2b, amcn, amcn1, amcx1, amd1, amdm, amelx, amely, amfr, amg, amgl, amgx, amh, amhr, amhr2, aml1, aml1t1, aml2, aml3, amog, ampd1, ampd2, ampd3, amph, amph1, ampk, amt, amy1a, amy1b, amy1c, amy2a, amy2b, an2, anc, ancr, ang, ang1, anh1, ank1, ank2, ank3, anop1, anova, anp, anpep, anpra, anprb, anprc, ans, ant1, ant2, ant3, ant3y, anx1, anx11, anx13, anx2, anx2l4, anx3, anx4, anx5, anx6, anx7, anx8, aoah, aoc2, aox1, ap2tf, apah1, apba1, apba2, apbb1, apbb2, apc, apcs, ape, apeced, apeh, apex, api1, api2, api3, apj, aplp, aplp1, aplp2, apnh, apo3l, apoa1, apoa2, apoa4, apob, apobec1, apoc1, apoc2, apoc3, apoc4, apod, apoe, apoer2, apoh, apolmt, apolp1@, apolp2@, app, appbp1, appl1, aprf, aprt, aps, apt1, apt1lg1, apx1, apy, aqdq, aqp0, aqp1, aqp2, aqp2l, aqp3, aqp4, aqp5, aqp6, aqp7, ar, ar1, ara, araf1, araf2, arcn1, ard1, ard1, areg, arf1, arf2, arf3, arf4l, arf5, arg, arg1, args, arh12, arh6, arh9, arha, arhb, arhc, arhg, arhgap2, arhgap3, arhgap6, arhgdia, arhgdib, arhh, arix, arl2, armd1, arnt, arntl, aro, arp, arp1, arpkd, arr3, arrb1, arrb2, arsa, arsacs, arsb, arsc1, arsc2, arsd, arse, arsf, art, art1, art3, art4, arts, arvd1, arvd2, arvd3, arvd4, as, asat, asb, ascl1, ascl2, asct1, asd1, asd2, asgr1, asgr2, ash1, asip, asl, asln, asm1, asma, asmd, asmt, asmtlx, asmty, asnrs, asns, aspa, ass, astml, astn, asv, at, at1, at2r1, at3, ata, atbf1, atcay, atf1, ath1, aths, atm, atoh1, atox1, atp1a1, atp1a2, atp1a3, atp1al1, atp1b1, atp1b2, atp1b3, atp1bl1, atp1g1, atp2a1, atp2a2, atp2a3, atp2b, atp2b1, atp2b2, atp2b2, atp2b3, atp2b4, atp4a, atp4b, atp5, atp5a, atp5b, atp5g1, atp5g2, atp5g3, atp5o, atp6a, atp6b1, atp6c, atp6e, atp6n1, atp7a, atp7b, atpm, atpsb, atpsk1, atpsk2, atq1, atr, atr, atr1, atr1, atr2, atrc1, atrc2, atrx, ats, atsv, atx1, atx2, au, auf1, auf1a, aut, avcd, aved, avp, avpr1a, avpr1b, avpr2, avpr3, avrp, avsd, awal, axl, axl1g, axsf, azf1, azf2, azgp1, azu1, b120, b144, b1g1, b29, b2m, b2mr, b3galt4, b4galt1, ba2r, babl, bag1, bai1, bai2, bai3, bak1, bam22, bap1, bap135, bapx1, bard1, bark2, bas, bat1, bat2, bat3, bat4, bat5, bax, bb1, bbbg1, bbbg2, bbs1, bbs2, bbs3, bbs4, bbs5, bcas1, bcat1, bcat2, bcate2, bcd1, bcei, bche, bckdha, bckdhb, bcl1, bcl10, bcl2, bcl2a1, bcl2l2, bcl3, bcl5, bcl6, bcl7, bcl7a, bcl8, bcl9, bclw, bcm, bcm1, bcma, bcns, bcns, bcp, bcpm, bcpr, bcr, bcrl2, bcrl3, bcrl4, bcsg1, bct1, bct2, bdb, bdb1, bdc, bde, bdkrb1, bdkrb2, bdmf, bdmr, bdnf, bed, bedp, bek, bene, bevi, bf, bf1, bf2, bfhd, bfic, bfls, bfnc2, bfp, bfsp1, bft, bglap, bgmr, bgn, bgp, bhd, bhpcdh, bhr1, bicd1, bid, bigh3, bin1, bir, bjs, bkma1, blast1, blau, blk, blm, blmh, bltr, blvra, blvrb, blym, bmal1, bmd, bmh, bmi1, bmp1, bmp2, bmp2a, bmp2b1, bmp3, bmp4, bmp5, bmp6, bmp7, bmp8, bmpr1a, bmpr1b, bmx, bmyb, bn51t, bnc, bnc1, bnp, bor, bpad, bpag1, bpag2, bpes, bpes1, bpes2, bpgm, bphl, bpi, br, br140, braf, brca1, brca2, brca3, brcacox, brcd1, brcd2, brdt, brf1, brhc, bric, brks, brn3a, brn3b, brn3c, brrn1, brw1c, bs, bsap, bsep, bsf2, bsg, bsnd, bssl, bst1, bst2, btak, btc, btd, bteb, bteb1, btg1, btg2, bths, btk, btkl, btn, bts, bub1b, bubr1, bwr1a, bwr1b, bws, bwscr1a, bwscr1b, bzrp, bzx, c11orf13, c1nh, c1qa, c1qb, c1qbp, c1qg, c1r, c1s, c2, c21orf1, c21orf2, c21orf3, c2ta, c3, c3br, c3dr, c3g, c4a, c4b, c4bpa, c4bpb, c4f, c4s, c5, c5ar, c5r1, c6, c7, c8a, c8b, c8g, c9, ca1, ca12, ca125, ca2, ca21h, ca3, ca4, ca5, ca6, ca7, ca8, ca9, caaf1, cabp9k, cac, cac@, caca, cacd, cacna1a, cacna1b, cacna1c, cacna1d, cacna1e, cacna1f, cacna1s, cacna2, cacnb1, cacnb2, cacnb3, cacnb4, cacng, cacnl1a1, cacnl1a2, cacnl1a3, cacnl1a4, cacnl1a5, cacnl1a6, cacnl2a, cacnlb1, cacnlg, cacp, cact, cacy, cad, cad11, cadasil, cae1, cae3, caf, cafla, caga, cagb, cain, cak, cak1, call1, calb1, calb2, calb3, calc1, calc2, calca, calcb, calcr, cald1, calla, calm1, calm2, calm3, calml1, calml3, calna, calna3, calnb, calnb1, calr, cals, calt, calu, cam, camk4, camkg, caml1, camlg, camp, can, canp3, canx, cap2, cap3, cap37, capb, capg, capl, capn1, capn2, capn3, capn4, cappa2, cappb, capr, caps, capza2, capzb, car, carp, cars, cart1, cas, cas2, casil, casp1, casp10, casp2, casp3, casp3, casp4, casp5, casp6, casp7, casp8, casq1, casq2, casr, cast, cat, cat1, cat4, catf1, catm, cav1, cav2, cav3, cbbm, cbd, cbfa1, cbfa2, cbfa2t1, cbfa3, cbfb, cbg, cbl, cbl2, cbln2, cbp, cbp, cbp2, cbp68, cbr1, cbs, cbt, cbt1, cc10, cca, cca1, ccal1, ccal2, ccbl1, ccckr5, ccg1, ccg2, cchl1a1, cchl1a2, cchl1a3, cchlb1, cck, cckar, cckbr, ccl, ccm1, ccm2, ccm3, ccn1, ccna, ccnb1, ccnc, ccnd1, ccnd2, ccnd3, ccne, ccnf, ccng1, ccnh, ccnt, ccnt1, cco, ccr10, ccr2, ccr3, ccr9, ccsp, cct, ccv, cczs, cd, cd10, cd11a, cd1b, cd11c, cd13, cd137, cd14, cd15, cd151, cd156, cd16, cd164, cd18, cd19, cd1a, cd1b, cd1c, cd1d, cd1e, cd2, cd20, cd22, cd23, cd24, cd26, cd27, cd27l, cd28, cd28lg, cd28lg2, cd30, cd32, cd33, cd34, cd36, cd36l1, cd36l2, cd37, cd38, cd39, cd39l1, cd3d, cd3e, cd3g, cd3z, cd4, cd40, cd40lg, cd41b, cd43, cd44, cd45, cd46, cd47, cd48, cd49b, cd49d, cd5, cd53, cd57, cd58, cd59, cd5l, cd6, cd63, cd64, cd68, cd69, cd7, cd70, cd71, cd72, cd74, cd79a, cd79b, cd80, cd81, cd82, cd82, cd86, cd8a, cd8b, cd8b1, cd9, cd94, cd95, cd97, cd99, cda, cda1, cda3, cdan1, cdan2, cdan3, cdb2, cdc2, cdc20, cdc25a, cdc25b, cdc25c, cdc27, cdc2l1, cdc2l2, cdc2l4, cdc34, cdc42, cdc5l, cdc7, cdc7l1, cdcd1, cdcd2, cdcd3, cdcl1, cdcrel, cdg1, cdgdl, cdgg1, cdgs2, cdh1, cdh11, cdh12, cdh13, cdh14, cdh15, cdh16, cdh16, cdh17, cdh2, cdh3, cdh5, cdh7, cdh8, cdhb, cdhh, cdhp, cdhs, cdk2, cdk3, cdk4, cdk5, cdk7, cdk8, cdk9, cdkn1, cdkn1a, cdkn1b, cdkn1c, cdkn2a, cdkn2b, cdkn2d, cdkn3, cdkn4, cdl1, cdm, cdmp1, cdmt, cdpx1, cdpx2, cdpxr, cdr1, cdr2, cdr3, cdr62a, cdsn, cdsp, cdtb, cdw50, cdx1, cdx2, cdx3, cdx4, cea, cebp, cebpa, cebpb, cebpd, cebpe, cecr, cel, cell, cen1, cenpa, cenpb, cenpc, cenpc1, cenpe, cenpf, cerd4, ces, ces1, cetn1, cetp, cf, cf2r, cfag, cfag, cfc, cfd1, cfeom1, cfeom2, cfh, cfl1, cfl2, cfnd, cfns, cftr, cg1, cga, cgat, cgb, cgd, cgf1, cgh, cgrp, cgs23, cgt, cgthba, chac, chat, chc1, chd1, chd2, chd3, chd4, chd5, chdr, che1, che2, ched, chek1, chga, chgb, chgc, chh, chi3l1, chip28, chit, chk1, chlr1, chlr2, chm, chm1, chn, chn1, chn2, chop10, chr, chr39a, chr39b, chr39c, chrm1, chrm2, chrm3, chrm4, chrm5, chrna1, chrna2, chrna3, chrna4, chrna5, chrna7, chrnb1, chrnb2, chrnb3, chrnb4, chrnd, chrne, chrng, chrs, chs1, chx10, ciipx, cip1, cirbp, cish, ck2a1, ckap1, ckb, ckbb, ckbe, ckm, ckmm, ckmt1, ckmt2, ckn1, ckn2, ckr3, ckrl1, ckrl3, cl, cl100, cla1, cla1, clac, clapb1, clapm1, claps3, clc, clc7, clck2, clcn1, clcn2, clcn3, clcn4, clcn5, clcn6, clcn7, clcnka, clcnkb, cld, cldn3, cldn5, clg, clg1, clg3, clg4a, clg4b, cli, clim1, clim2, clk2, clk3, cln1, cln2, cln3, cln5, cln6, cln80, clns1a, clns1b, clp, clpp, clps, clta, cltb, cltc, cltcl1, cltd, clth, clu, cma1, cmah, cmar, cmd1, cmd1a, cmd1b, cmd1c, cmd1d, cmd1e, cmd1f, cmd3a, cmdj, cmh1, cmh2, cmh3, cmh4, cmh6, cmkbr1, cmkbr2, cmkbr3, cmkbr5, cmkbr6, cmkbr7, cmkbr8, cmkbr9, cmkbrl2, cmklr1, cmkrl1, cmkrl2, cml, cmm, cmm2, cmoat, cmp, cmpd1, cmpd2, cmpd2, cmpd3, cmpx1, cmt1a, cmt1b, cmt2a, cmt2b, cmt2d, cmt2d, cmt4a, cmt4b, cmtnd, cmtx1, cmtx2, cna1, cna2, cnbp1, cnc, cncg1, cncg2, cncg3l, cnd, cng3, cnga1, cnga3, cngb1, cnn1, cnn2, cnn3, cnp, cnr1, cnsn, cntf, cntfr, cntn1, co, coca1, coca2, coch, cod1, cod2, coh1, coil, col10a1, col11a1, col11a2, col12a11, col13a1, col15a1, col16a1, col17a1, col18a1, col19a1, col1a1, col1a2, col1ar, col2a1, col3a1, col4a1, col4a2, col4a3, col4a4, col4a5, col4a6, col5a1, col5a2, col6a1, col6a2, col6a3, col7a1, col8a1, col8a2, col9a1, col9a11, col9a2, col9a3, colq, comp, comt, copeb, copt1, copt2, cord1, cord2, cord5, cord6, cort, cot, cox10, cox4, cox5b, cox6a1, cox6b, cox7a1, cox7a2, cox7a3, cox7am, cox8, cp, cp107, cp115, cp20, cp47, cp49, cpa1, cpa3, cpb2, cpb2, cpd, cpe, cpetr2, cpm, cpn, cpn1, cpn2, cpo, cpp, cpp32, cpp32, cppi, cps1, cpsb, cpsd, cpt1a, cpt1b, cpt2, cpu, cpx, cpx, cpxd, cr1, cr2, cr3a, crabp1, crabp2, crapb, crarf, crat, crbp1, crbp2, crd, crd1, creb1, creb2, crebbp, crebl1, crem, crfb4, crfr2, crh, crhbp, crhr, crhr1, crhr2, crip, crk, crk1, crm1, crmp1, crmp2, crp, crp1, crs, crs1c, crs2, crs3, crsa, crt, crtl1, crtm, crx, cry1, cry2, crya1, crya2, cryaa, cryab, cryb1, cryb2, cryb3, cryba1, cryba2, cryba4, crybb1, crybb2, crybb3, cryg1, cryg2, cryg3, cryg4, cryg8, cryg@, cryga, crygb, crygc, crygd, crygs, crym, cryz, cs, csa, csb, csbp1, csci, csd, csd2, csda, cse, cse11, csf1, csf1r, csf2, csf2ra, csf2rb, csf2ry, csf3, csf3r, csh1, csh2, csk, csmf, csn, csn10, csn2, csn3, csnb1, csnb2, csnb3, csnk1a1, csnk1d, csnk1e, csnk1g2, csnk2a1, csnk2a2, csnk2b, csnu3, cso, cspb, cspg1, cspg2, cspg3, csr, csrb, csrp, csrp1, csrp2, cst1, cst1, cst2, cst3, cst4, cst5, cst6, csta, cstb, csx, ct2, ctaa1, ctaa2, ctag, ctb, ctbp1, ctbp2, ctgf, cth, cthm, ctk, ctla1, ctla3, ctla4, ctla8, ctm, ctnna1, ctnna2, ctnnb1, ctnnd, ctnnd1, ctnr, ctns, ctp, ctpct, ctps, ctr1, ctr2, ctrb1, ctrl, ctsa, ctsb, ctsc, ctsd, ctse, ctsg, ctsgl2, ctsh, ctsk, ctsl, ctss, ctsw, ctsz, ctx, cubn, cul3, cul4b, cul5, cutl1, cvap, cvd1, cvl, cx26, cx31, cx32, cx37, cx40, cx43, cx46, cx50, cxb3s, cxcr4, cxorf4, cyb5, cyb561, cyba, cybb, cyc1, cyk4, cyld1, cymp, cyp1, cyp11a, cyp11b1, cyp11b2, cyp17, cyp19, cyp1a1, cyp1a2, cyp1b1, cyp21, cyp24, cyp27, cyp27a1, cyp27b1, cyp2a, cyp2a3, cyp2a6, cyp2b, cyp2c, cyp2c19, cyp2c9, cyp2d, cyp2d@, cyp2e, cyp2e1, cyp2f1, cyp2j2, cyp3a4, cyp4a11, cyp4b1, cyp51, cyp7, cyp7a1, cyr61, cyrn1, cyrn2, czp3, d10s105e, d10s170, d10s170, d11s302e, d11s636, d11s813e, d11s833e, d12s2489e, d12s53e, d13s1056e, d13s25, d14s46e, d15s12, d15s226e, d15s227e, d16s2531e, d16s469e, d17s136e, d17s811e, d18s892e, d19s204, d19s381e, d1s111, d1s155e, d1s166e, d1s1733e, d1s2223e, d1s61, d2h, d2s201e, d2s448, d2s448e, d2s69e, d3s1231e, d3s1319e, d3s48e, d4, d4s90, d5s1708, d5s346, d6, d6s1101, d6s207e, d6s2244e, d6s2245e, d6s228e, d6s229e, d6s230e, d6s231e, d6s51e, d6s52e, d6s54e, d6s81e, d6s82e, d7s437, d8s2298e, d9s46e, da1, da2b, dab2, dac, dad1, daf, dag, dag1, dag2, dagk1, dagk4, dam10, dam6, damox, dan, dao, dap, dap3, dap5, dapk1, dar, dat1, dax1, daxx, daz, dazh, dazl, dba, dbccr1dbcn, dbh, dbi, dbi, dbl, dbm, dbn1, dbp, dbp, dbp1, dbp2, dbpa, dbt, dbx, dby, dcc, dce, dci, dck, dcn, dcoh, dcp1, dcr, dcr3, dct, dctn1, dcx, ddb1, ddb2, ddc, ddh1, ddh2, ddit1, ddit3, ddost, ddp, ddpac, ddr, ddx1, ddx10, ddx11, ddx12, ddx15, ddx16, ddx2a, ddx3, ddx5, ddx6, ddx9, dec, decr, def1, def4, def5, def6, defa1, defa4, defa5, defa6, defb1, defb2, dek, denn, dents, dep1, der12, des, dff1, dffa, dffrx, dffry, dfn1, dfn2, dfn3, dfn4, dfn6, dfna1, dfna10, dfna11, dfna12, dfna13, dfna2, dfna2, dfna4, dfna5, dfna6, dfna7, dfna8, dfna9, dfnb1, dfnb12, dfnb13, dfnb14, dfnb16, dfnb17, dfnb18, dfnb2, dfnb3, dfnb4, dfnb5, dfnb6, dfnb7, dfnb8, dfnb9, dgcr, dgcr2, dgcr2, dgcr6, dgi1, dgka, dgkq, dgpt, dgpt, dgs, dgs2, dgsi, dgu, dhc2, dhcr7, dhfr, dhlag, dhp, dhpr, dhps, dhrd, dhtr, di, di1, dia, dia1, dia2, dia4, diaph1, diaph2, dif2, diff6, dipi, dir, dkc, dkc1, dlc1, dld, dlg1, dlg2, dlg3, dlg4, dlst, dlx1, dlx2, dlx2, dlx3, dlx4, dlx5, dlx6, dlx7, dlx8, dm, dm2, dmahp, dmbt1, dmd, dmda1, dmdl, dmh, dmk, dmp1, dmpk, dmsfh, dmt, dmt1, dmtn, dna2l, dnah, dnah1, dnah11, dnah12, dnah2, dnahc1, dnahc11, dnahc2, dnahc3, dnase1, dnase1l1, dnase1l3, dnase2, dnch2, dncl, dncm, dnecl, dnel1, dnl, dnl1, dnl1l, dnm1, dnmt1, dnmt2, dnpk1, dns, dntt, do, doc1, doc2, dock1, dock180, dod, dok1, dom, dp1, dp1, dp2, dp3, dpagt2, dpc4, dpd, dpde1, dpde2, dpde3, dpde4, dpep1, dph2l2, dpp, dpp4, dpp6, dpt, dpyd, dpys, dpysl1, dpysl2, dr1, dr3, dr3lg, dr5, dra, drad, drada, dral, drd1, drd1b, drd1b, drd1l2, drd2, drd3, drd4, drd5, drill, drp1, drp1, drp2, drp2, drp3, drpla, drt, dsc1, dsc2, dsc3, dsc3, dsc4, dscam, dscr, dsg1, dsg2, dsg3, dsp, dspg3, dspp, dss, dss1, dtd, dtdp2, dtdst, dtna, dtr, dts, dus, dusp1, dusp11, dusp2, dusp3, dusp4, dusp5, dusp6, dusp7, dusp8, dut, dvl, dvl1, dvl1, dvl3, dxf68s1e, dxs1272e, dxs128, dxs1283e, dxs423e, dxs435e, dxs522e, dxs648, dxs707, dxs8237e, dxys155e, dylx2, dyrk, dys, dysf, dyt1, dyt3, dyt5, dyt6, dyt7, dyt8, dyt9, dyx1, dyx2, e11s, e14, e1b, e2a, e2f1, e2f2, e2f3, e2f4, e3, e4f, e4fl, e4tfla, e4tfl b, ea1, eaac1, eaat1, eaat2, eac, ead, eag, eap, ear1, ear2, ear3, ebaf, ebf, ebi1, ebm, ebn1, ebn1, ebn2, ebr2a, ebs1, ebvm1, ebvs1, ec1, eca1, ecb2, ece1, ecgf1, ech1, echs1, eck, ecm1, ecp, ecs1, ect2, ed1, ed2, ed3, ed4, eda, eda3, eddr1, edg3, edg6, edh, edh17b2, edh17b2, edh17b3, edm1, edm2, edm3, edmd, edmd2, edn, edn1, edn2, edn3, ednra, ednrb, eec1, eec2, eef1a1, eef1a2, eef1b1, eef1b2, eef1b3, eef1b4, eef2, eeg1, eegv1, eek, een, ef1a, ef2, efe2, efempl, ef16, efmr, efna1, efna3, efna4, efnb1, efnb2, efnb3, efp, eftu, egf, egfr, egi, egr1, egr2, egr3, egr4, ehhadh, ehoc1, ei, eif1a, eif2g A, eif2s3 A, eif3s10, eif3s6, eif4al, eif4a2, eif4c, eif4e, eif4ebp1, eif4ebp2, eif4el1, eif4el2, eif4g, eif4g1, eif4g2, eif5a, ejm1, el1, ela1, ela2, elam1, elanh2, elavl1, elavl2, elavl4, elc, ele1, elf3, elk1, elk2, elk3, elk4, ell, eln, em9, emap, emapl, emd, emd2, emk1, emp1, emp55, emr1, ems1, emt, emtb, emx1, emx2, en1, en2, ena78, end, endog, enfl2, eng, enl, eno1, eno2, eno3, enpep, ent1, entk, enur1, enur2, enx2, eos, ep3, ep300, epa, epb3, epb3l1, epb41, epb4l2, epb42, epb49, epb72, epha1, epha2, epha3, epha8, ephb1, ephb2, ephb3, ephb4, ephb6, epht1, epht2, epht3, ephx1, ephx2, epim, eplg1, eplg2, eplg3, eplg4, eplg5, eplg8, epm1, epm2, epm2a, epmr, epo, epor, eppk, eprs, eps15, eps8, ept, erba1, erba2, erba12, erbal3, erbb2, erbb3, erbb4, erc55, ercc1, ercc2, ercc3, ercc4, ercc5, ercc6, ercm1, erda1, erf1, erg, erg3, ergic53, erh, erk, erk1, erk2, erk3, erm, erpl1, erv1, erv1, erv3, ervr, ervt1, ervt2, ervt3, ervt4, ervt5, eryf1, es1, es130, esa, esa1, esa4, esat, esb3, esd, esg, esr, esr1, esr2, esrl1, esrl2, esrra, esrrb, esrrg, ess1, est, est, est2, est25263, esx, etfa, etfb, etfdh, etk1, etk2, etm1, etm2, eto, ets1, ets2, etv1, etv3, etv4, etv5, etv6, evc, evcl, evda, evdb, evi1, evi2, evi2a, evi2b, evpl, evr1, evx1, evx2, ews, ewsr1, exlm1, ext1, ext2, ext3, extl1, extl2, eya1, eya2, eya3, eycl1, eycl3, ezh1, ezh1, ezh2, f10, f11, f12, f13a f13a1, f13b, f2, f2r, f2rl2, f2rl3, f3, f5, f5f8d, f7, f7e, f7r, f8a, f8b, f8c, f8vwf, f9, fa, fa1, faa, fabp1, fabp2, fabp3, fabp4, fabp6, fac1, faca, facc, facd, face, facl1, facl2, facl3, facl4, facvl1, fad, fadd, fadk, fah, fak2, faldh, fall39, falz, fanca, fancc, fancd, fance, fancg, fap, fapa, farr, fas, fasl, fasn, fast1, fat, fau, fbln1, fbln2, fbn1, fbn2, fbn1, fbp1, fcar, fcc1, fce, fce2, fcer1a, fcer1b, fcer1g, fcer2, fcgr1a, fcgr1b, fcgr1c, fcgr2a, fcgr3a, fcgrt, fcmd, fcn1, fcn2, fcp, fcp1, fcpx, fct3a, fdc, fdft1, fdh, fdpsl1, fdpsl2, fdpsl3, fdpsl4, fdpsl5, fdx1, fdxr, fe65, fe65l1, fea, feb1, feb2, fecb, fech, fen1, feo, feom, feom1, feom2, fer, fes, fet1, fevr, ffm, fga, fgarat, fgb, fgc@, fgd1, fgdy, fgf1, fgf10, fgf11, fgf12, fgf13, fgf14, fgf2, fgf2, fgf3, fgf4, fgf5, fgf6, fgf7, fgf8, fgf9, fgfa, fgfb, fgfr1, fgfr2, fgfr3, fgfr4, fgg, fgr, fgs1, fh, fh, fh3, fhc, fhf1, fhf3, fhf4, fhh2, fhit, fhl1, fhl2, fhr2, fic1, figf, fih, fim, fim1, fim3, fimg, fkbp12, fkbp1a, fkbp2, flch2, fkhl1, fkhl10, fkhl12, fkhl15, fkhl16, fkhl17, fkhl2, fkhl5, fkhl6, fkhl7, fkhl8, fkhl9, fkhr, fkhrl1, flg, fli1, flii, fln1, fln2, flna, flnb, flnms, flot2, flt1, flt2, flt3, flt4, fmf, fmn, fmo1, fmo2, fmo3, fmod, fmr1, fmr2, fms, fn1, fnl2, fnra, fnrb, fnrb1, fnta, fntb, folh, folh1, folr1, folr2, folt, fos, fosb, fosl1, fosl2, fpah, fpc, fpd1, fpdmm, fpf, fpgs, fp1, fpp, fpr1, fprh1, fprh2, fprl1, fprl2, fprp, fpsl2, fpsl3, fpsl4, fpsl5, fr, frap1, fraxa, fraxe, fraxf, frda, freac2, freac6, freac9, frg1, frp1, frv1, frv2, frv3, fsg1, fsgs, fshb, fshd1a, fshmd1a, fshprh1, fshr, fssv, fth1, fth16, ftl, ftz1, ftzf1, fuca1, fica2, fur, fus, fuse, fut1, fut2, fut3, fut4, fut5, fut6, fit7, fut8, fvt1, fxr1, fxy, fy, fyn, fzd1, fzd2, fzd3, fzd5, fzd6, fzd7, fzr, g0s8, g10pl, g10p2, g17, g17p1, g19p1, g1p1, g1p2, g1p3, g22p1, g6pc, g6pd, g6pd1, g6pd1, g6pt, g6pt1, g6s, g7p1, ga2, gaa, gabatr, gabpa, gabpb1, gabra1, gabra2, gabra3, gabra4, gabra5, gabra6, gabrb1, gabrb2, gabrb3, gabrd, gabre, gabrg1, gabrg2, gabrg3, gabrr1, gabrr2, gad1, gad2, gad3, gadd153, gadd45, gak, gal, galbp, galc, gale, galgt, galk1, galk2, galn, galnact, galnr, galnr1, galns, galnt1, galnt2, galnt3, galr1, galt, gan, gan1, ganab, ganc, gap, gap1m, gap43, gapd, gar22, garp, gars, gart, gas, gas1, gas2, gas41, gas6, gas7, gasr, gast, gata1, gata2, gata3, gata4, gata6, gay1, gba, gbas, gbbb1, gbbb2, gbe1, gbp1, gbx2, gc, gcap, gcap2, gcdh, gcf1, gcf2, gcfx, gcg, gcgr, gch1, gck, gckr, gcn5l1, gcn5l2, gcnf, gcnt1, gcnt2, gep, gcp2, ges, gcs1, gcsf, gcsfr, gcsp, gctg, gcy, gda, gde, gdf5, gdf8, gdh, gdi1, gdi2, gdid4, gdld, gdnf, gdnfr, gdnfra, gdnfrb, gdx, gdxy, ge, gem, geney, gey, gfl, gfl, gfap, gfer, gfer, gfi1, gfpt, gfra1, gfra2, ggcx, ggt1, ggt2, ggta1, ggtb1, ggtb2, gh1, gh2, ghc@, ghdx, ghn, ghr, ghrf, ghrh, ghrhr, ghs, ghv, gif, gifb, gip, gip, gipr, girk1, girk2, girk3, girk4, gja1, gja3, gja4, gja5, gja8, gjb1, gjb2, gjb3, gk, gk2, gla, glat, glb1, glb2, glc1a, gl1b, glc1c, glc1d, glc1f, glc3a, glc3b, glc1c, glc1r, glct2, glct3, gldc, glepp1, glg1, gli, gli2, gli3, gli4, glnn, glns, glo1, glo2, glp1r, glra1, glra2, glra3, glrb, glrx, gls, glud1, glud2, glul, glur1, glur2, glur3, glur4, glur5, glur6, glur7, glut1, glut2, glut3, glut4, glut5, glvr1, glvr2, gly96, glya, glyb, glys1, glyt1, glyt1, glyt2, gm2a, gma, gmcsf, gmds, gml, gmpr, gmps, gna11, gna15, gna16, gnai1, gnai2, gnai2a, gnai2b, gnai2l, gnai3, gnal, gnao1, gnaq, gnas, gnas1, gnat1, gnat2, gnaz, gnb1, gnb2, gnb3, gng5, gnl1, gnpta, gnrh1, gnrh2, gnrhr, gns, gnt1, golga4, got1, got2, gp130, gp1ba, gp1bb, gp2, gp2b, gp39, gp3a, gp75, gp78, gp9, gpa, gpam, gpat, gpb, gpc, gpc1, gpc3, gpc4, gpd, gpd1, gpd2, gpds1, gpe, gpi, gpi2, gpm6a, gpm6b, gpoa, gpr1, gpr10, gpr11, gpr12, gpr13, gpr15, gpr17, gpr18, gpr19, gpr2, gpr20, gpr21, gpr22, gpr23, gpr25, gpr29, gpr3, gpr30, gpr31, gpr32, gpr35, gpr37, gpr39, gpr4, gpr5, gpr6, gpr7, gpr8, gpr9, gprcy4, gprk21, gprk4, gprk5, gprk6, gprv28, gpsa, gpsc, gpt, gpx1, gpx2, gpx3, gpx4, gr2, grb1, grb10, grb2, grf2, gria1, gria2, gria3, gria4, grid2, grik1, grik2, grik3, grik4, grik5, grin1, grin2a, grin2b, grin2c, grin2d, grina, grk1, grk5, grk6, grl, grll1, grm3, grm8, grmp, grn, gro1, gro2, gro3, grp, grp58, grp78, grpr, grx, gs, gs1, gsas, gsc, gscl, gse, gshs, gsl, gsm1, gsn, gsp, gspt1, gsr, gss, gst12, gstl1, gst2, gst2, gst3, gst4, gst5, gsta1, gsta2, gstm1, gstm1, gstm2, gstm3, gstm4, gstm5, gstp1, gstt2, gt1, gt335, gta, gtb, gtbp, gtd, gtf2e2, gtf2f1, gtf2h1, gtf2h2, gtf2h4, gtf2i, gtf2s, gtf3a, gtg, guc1a2, guc1a3, guc1b3, guc2c, guc2d, guc2f, guca1a, guca1b, guca2, guca2, guca2a, guca2b, gucsa3, gucsb3, gucy1a2, gucy1a3, gucy1b3, gucy2c, gucy2d, gucy2f, guk1, guk2, gulo, gulop, gusb, gusm, gust, gxp1, gypa, gypb, gypc, gype, gys, gys1, gys2, gzma, gzmb, gzmh, gzmm, h, h142t, h19, h1f0, h1f1, h1f2, h1f3, h1f4, h1f5, h1fv, h2a, h2ax, h2az, h2b, h2b, h3f2, h3f3b, h3ft, h3t, h4, h4f2, h4f5, h4fa, h4fb, h4fc, h4fd, h4fe, h4fg, h4fh, h4fi, h4fj, h4fk, h4fl, h4fm, h4m, h6, ha2, habp1, hadha, hadhb, hadhsc, haf, hagh, hah1, haip1, hal, hap, hap1, hap2, hars, has2, hat1, hausp, hb1, hb1, hb6, hba1, hba2, hbac@, hbb, hbbc@, hbd, hbe1, hbegf, hbf2, hbg1, hbg2, hbgr, hbhr, hbm, hbp, hbq1, hbz, hc2, hc3, hca, hcat2, hccs, hcdh, hcf2, hcfc1, hcg, hck, hcl1, hcl2, hcl3, hcls1, hcp, hcp1, hcs, hcvs, hd, hdac1, hdc, hdgf, hdhc7, hdlbp, hdld, hdldt1, hdr, hed, hed, hegfl, hek, hek3, heln1, hem1, hema, hemb, hemc, hempas, hen1, hen2, hep, hep10, her2, her4, herg, herv1, hes1, hesx1, het, hexa, hexb, hf1, hf10, hfc1, hfe, hfe2, hfh11, hfsp, hgd, hgf, hgf, hgfl, hgl, hh, hh72, hhc1, hhc2, hhd, hhh, hhmjg, hhr23a, hht1, hht2, hiap2, higm1, hilda, hint, hiomt, hip, hip1, hip116, hip2, hir, hira, his1, his2, hive1, hivep1, hivep2, hjcd, hk1, hk2, hk3, hk33, hke4, hke6, hkr1, hkr2, hkr3, hkr4, hl11, hl19, hla-a, hla-b, hla-c, hla-cda12, hla-dma, hla-dmb, hla-dna, hla-dob, hla-dpa1, hla-dpb1, hla-dqa1, hla-dr1b, hla-dra, hla-e, hla-f, hla-g, hla-ha2, hladp, hlaf, hlals, hlcs, hlm2, hlp, hlp3, hlr1, hlr2, hlt, hlx1, hlxb9, hmaa, hmab, hmat1, hmbs, hmcs, hmg1, hmg14, hmg17, hmg2, hmgcl, hmgcr, hmgcs1, hmgcs2, hmgic, hmgiy, hmgx, hmmr, hmn2, hmox1, hmox2, hmr, hms1, hmsn1, hmx1, hmx2, hnd, hnf1a, hnf2, hnf3a, hnf3b, hnf4a, hnp36, hnpcc6, hnrpa1, hnrpa2b1, hnrpd, hnrpf, hnrpg, hnrph1, hnrph2, hnrph3, hnrpk, homg, hops, hox10, hox11, hox12, hox1@, hox1a, hox1b, hox1c, hox1d, hox1e, hox1f, hox1g, hox1h, hox1i, hox1j, hox2@, hox2a, hox2b, hox2c, hox2d, hox2e, hox2f, hox2g, hox2h, hox2i, hox3@, hox3a, hox3b, hox3c, hox3d, hox3e, hox3f, hox3g, hox4@, hox4a, hox4b, hox4c, hox4d, hox4e, hox4f, hox4g, hox4h, hox4i, hox7, hox8, hoxa1, hoxa10, hoxa11, hoxa13, hoxa3, hoxa4, hoxa5, hoxa6, hoxa7, hoxa9, hoxa@, hoxb1, hoxb2, hoxb3, hoxb4, hoxb5, hoxb6, hoxb7, hoxb8, hoxb9, hoxb@, hoxc12, hoxc13, hoxc4, hoxc5, hoxc6, hoxc8, hoxc9, hoxc@, hoxd1, hoxd10, hoxd11, hoxd12, hoxd13, hoxd3, hoxd4, hoxd8, hoxd9, hoxd@, hoxhb9, hp, hp4, hpafp, hpc1, hpc2, hpca, hpcal1, hpcx, hpd, hpdr1, hpdr2, hpe1, hpe2, hpe3, hpe4, hpe5, hpect1, hpfh, hpfh2, hpgd, hplh1, hplh2, hpn, hpr, hprt, hprt1, hps, hpt, hpt1, hptp, hptx, hpv18i1, hpv18i2, hpx, hr, hras, hrb, hrc, hrc1, hrca1, hrd, hres1, hrf, hrg, hrga, hrh1, hrh2, hrmt1l1, hrpt2, hrx, hrx, hry, hsal1, hsal2, hsan1, hsas1, hscr2, hsd11, hsd11b1, hsd11b2, hsd11k, hsd11l, hsd17b1, hsd17b2, hsd17b3, hsd17b4, hsd3b1, hsd3b2, hsh, hsn1, hsorc1, hsp27, hsp73, hspa1a, hspa1b, hspa1l, hspa2, hspa3, hspa4, hspa5, hspa6, hspa7, hspa8, hspa9, hspb1, hspb2, hspc2, hspcal1, hspcal2, hspcal3, hspcal4, hspcb, hspg1, hspg2, hsr1, hsst, hstd, hstf1, htc2, htf4, htk, htkl, htl, htlf, htlvr, htn1, htn2, htn3, htnb, htor, htr1a, htr1b, htr1d, htr1e, htr1el, htr1f, htr2a, htr2b, htr2c, htr3, htr4, htr5a, htr6, htr7, htrx1, hts1, htt, htx, htx1, hub, hud, hup2, hur, hus, hv1s, hvbs1, hvbs6, hvbs7, hvem, hvh2, hvh3, hvh8, hxb, hxbl, hy, hya, hyal1, hyd2, hygn1, hyl, hyp, hyplip1, hypp, hypx, hyr, hyrc1, hys, ia1, ia2, iap, iapp, iar, iars, ibd1, ibd2, ibm2, ibsp, ica1, icam1, icam2, icam3, icca, ich1, icr2, icr2b, ics1, id1, id2, id3, id4, ida, idd, iddm1, iddm10, iddm11, iddm12, iddm13, iddm15, iddm17, iddm2, iddm3, iddm4, iddm5, iddm6, iddm7, iddm8, iddmx, ide, idg2, idh1, idh2, idh3a, idh3g, ido, ids, idua, ier1, ier3, iex1, if, ifcr, ifgr2, ifi16, ifi27, ifi35, ifi4, ifi5111, ifi54, ifi56, ifi616, ifi78, ifna1, ifna10, ifna13, ifna14, ifna16, ifna17, ifna21, ifna6, ifna7, ifna8, ifna@, ifnai1, ifnar1, ifnar2, ifnb1, ifnb2, ifnb3, ifng, ifngr1, ifngr2, ifngt1, ifnr, ifnw1, ifrd2, iga, igat, igb, igbp1, igd1, igda1, igdc1, igds2, iger, iges, igf1, igf1r, igf2, igf2r, igfbp1, igfbp10, igfbp2, igfbp3, igfbp4, igfbp6, igfbp7, igfr1, igfr2, igfr3, igh@, igha1, igha2, ighd, ighdy2, ighe, ighg1, ighg2, ighg3, ighg4, ighj, ighm, ighmbp2, ighr, ighv@, igi, igi, igk@, igkc, igkdel, igkj, igkjrb1, igkv, iglc, iglc1, iglj, iglp1, iglp2, iglv, igm, igo1, igsfl, ihh, ik1, ikba, il10, il10r, il11, il11ra, il12a, il12b, il12rb1, il12rb2, il13, il13ra1, il13ra2, il15, il15ra, il17, il1a, il1b, il1bc, il1r1, il1r2, il1ra, il1rap, il1rb, il1rn, il2, il2r, il2ra, il2rb, il2rg, il3, il3ra, il3ray, il4, il4r, il4ra, il5, il5ra, il6, il6r, il6st, il7, il7r, il8, il8ra, il8rb, il9, il9r, ila, ilfl, illbp, imd1, imd2, imd4, imd5, imd6, impa1, impdh1, impdh2, impdhl1, impg1, impt1, indx, infa2, infa4, infa5, ing1, inha, inhba, inhbb, inhbc, ini1, ink4b, inlu, inp10, inpp1, inpp5a, inpp5b, inpp5d, inppl1, ins, insig1, insl, insl3, insl4, insr, insrr, int1, int111, int2, int3, int4, int6, iosca, ip2, ipf1, ip1, ipm150, ipox, ipp, ipp2, ipw, iqgap1, ir10, ir20, ireb1, ireb2, irf1, irf2, irf4, irf4, irr, irs1, isa, iscw, isl1, islr, isot, issx, it15, itba1, itba2, itf, itf2, itga1, itga2, itga2b, itga4, itga5, itga6, itga7, itgad, itgal, itgam, itgav, itgax, itgb1, itgb2, itgb3, itgb4, itgb6, itgb7, iti, itih1, itih2, itih3, itih4, itihl1, itil, itk, itm1, itpa, itpka, itpkb, itpr1, itpr2, itpr3, itsn, ivd, ivl, jag1, jak1, jak2, jak3, jbs, jcap, jh8, jip, jk, jme, jmj, joag, jpd, jrk, jrkl, jtk14, jtv1, jun, junb, jund, jup, jv18, jws, k12t, kai1, kal1, kar, kars, katp1, kcna1, kcna10, kcna1b, kcna2b, kcna3, kcna4, kcna5, kcna6, kcna7, kcna8, kcna9, kcnab1, kcnab2, kcnb1, kcnc1, kcnc2, kcnc3, kcnc4, kcne1, kcnh1, kcnh2, kcnj1, kcnj10, kcnj11, kcnj12, kcnj15, kcnj3, kcnj4, kcnj5, kcnj6, kcnj6, kcnj7, kcnj8, kcnjn1, kcnk1, kcnk2, kcnk3, kcnma1, kcnq1, kcnq2, kcnq3, kcnq4, kcns2, kd, kdr, kel, kera, kf1, kfs, kfsd, kfsl, khk, kiaa0122, kid, kid1, kif2, kif3c, kif5b, kip1, kip2, kiss1, kit, klc2, klk1, klk2, klk3, klk3, klkb1, klkr, klrb1, klrc1, klrc2, klrc3, klrc4, klrd1, klst, kms, kms, kng, kno, kns1, kns2, knsl1, knsl4, kox1, kox11, kox12, kox13, kox15, kox16, kox18, kox19, kox2, kox2, kox22, kox25, kox30, kox32, kox4, kox5, kox6, kox7, kox9, kpna3, kpps1, kpps2, krag, kras1p, kras2, krev1, krg2, krn1, krnl1, krox20, krt1, krt10, krt12, krt13, krt14, krt15, krt16, krt17, krt18, krt19, krt2a, krt2e, krt3, krt4, krt5, krt6a, krt6b, krt7, krt8, krt9, krtha2, krtha5, krthb1, krthb6, ks, ktn1, ku70, kup, kvlqt1, kwe, l1.2, l1cam, l23mrp, lab7, lab72, lac, laci, lacs, lad, lad, lad1, laf4, lag3, lag5, lair1, lakl, lalba, lall, lam1, lama1, lama2, lama3, lama3, lama4, lama5, lamb1, lamb2, lamb2, lamb2t, lamb3, lambr, lamc1, lamc2, lamm, lamnb2, lamp, lamp1, lamp2, lamr1, lams, lap, lap18, laptm5, lar, lar1, lard, large, lars, lbp, lbr, lca, lca1, lcad, lcamb, lcat, lccs, lcfs2, lch, lck, lcn1, lcn2, lco, lcp1, lcp2, lct, ld, ld78, ldb1, ldb2, ldc, ldh1, ldh3, ldha, ldhb, ldhc, ldlr, le, lect2, lef1, lefty1, lefty2, lep, lepr, lerk5, lerk8, leu1, leu7, leut, lfa1a, lfa3, lfhl1, lfp, lgals1, lgals3, lgals3bp, lgals3p, lgcr, lgmd1, lgmd1a, lgmd1b, lgmd1c, lgmd1d, lgmd2b, lgmd2c, lgmd2d, lgmd2e, lgmd2f, lgmd2g, lgmd2h, lgs, lgtn, lhb, lhcgr, lhs, lhx1, lhx3, li, li2, lif, lifr, lig1, lig3, lig4, lim1, lim2, limab1, limk1, limpii, lip2, lipa, lipb, lipc, lipd, lipe, lipo, lis1, lis2, lisx, litaf, lkb1, lkn1, llgl1, lman1, lmn1, lmn2, lmna, lmnb1, lmnb2, lmo1, lmo2, lmo3, lmo4, lmo5, lmp10, lmp2, lmp7, lmpx, lms, lmx1, lmx1a, lmx1b, lmyc, lnhr, lnrh, locr, loh11cr2a, lor, lot1, lox, loxl, loxl1, lpa, lpaab, lpaata, lpap, lpc1, lpc2d, lpd1, lph, lpi, lpl, lpna3, lpp, lps, lpsa, lqt1, lqt2, lqt3, lqt4, lr3, lre1, lre2, lrp, lrp1, lrp2, lrp5, lrp7, lrp8, lrpap1, lrpr1, lrs1, lsamp, lsirf, lsl, lsn, lsp1, lss, lst1, lta, lta4h, ltb, ltb4r, ltbp1, ltbp2, ltbp2, ltbp3, ltbp3, ltbr, ltc4s, ltf, ltk, ltn, lu, lum, luxs, luzp, lw, ly64, ly6e, ly9, lyam1, lyb2, lyf1, lyl1, lyn, lyp, lyst, lyt10, lyz, lztr1, m11s1, m130, m17s1, m17s2, m195, m1s1, m3s1, m4s1, m6a, m6b, m6p2, m6pr, m6s1, m7v1, m7vs1, mab21l1, mac1a, mac2, mac25, macam1, macs, mad, mad2l1, madd, madh1, madh2, madh3, madh4, madh5, madh6, madh6, madh7, madh9, madm, madr1, maf, mafd1, mafd2, mag, mage1, mageb3, mageb4, magel1, magoh, magp, magp1, magp2, mak, mal, mall, man2a2, mana1, mana2, mana2x, manb, manb1, manba, maoa, maob, map1a, map1a1c3, map1b, map1b1c3, map2, map4, map80, map97, mapk1, mapkap3, mapkkk4, mapt, mar, mark3, mars, mas1, masp1, mat1a, mat2a, mata1, mata2, matk, matn1, matn3, max, maz, mb, mbd1, mbl, mbl2, mbp, mbp1, mbs, mbs2, mc1r, mc2r, mc3r, mc4r, mc5r, mcad, mcc, mcdc1, mcdr1, mcf2, mcf3, mcfd1, mch2, mch3, mch4, mch5, mckd, mcl, mcl1, mcm, mcm2, mcm2, mcm3, mcm6, mcm7, mcmt, mcop, mcor, mcp, mcp1, mcp3, mcph1, mcr, mcs, mcsf, mcsp, mct1, md1, mdb, mdc, mdcr, mddc, mdeg, mdf1, mdg, mdg1, mdh1, mdh2, mdk, mdk, mdm2, mdm4, mdr1, mdr3, mdrs1, mdrv, mds, mds1, mdu1, mdu2, mdu3, mdx, me1, me2, mea, mea6, mecl1, mecp2, med, mef, mef2a, mef2b, mef2c, mef2d, mefv, mehmo, meis1, meis2, mekk, mekk1, mekk4, mel, mel18, melf, memo1, men1, men2a, meox1, meox2, mep1a, mep1b, mer2, mer6, mest, met, metrs, mfap1, mfap2, mfap3, mfap4, mfd1, mfi2, mfs1, mfs2, mft, mfts, mg50, mga, mga1, mga3, mgat1, mgat2, mgat5, mgc1, mgcn, mgcr, mgct, mgdf, mgea, mgf, mgi, mgmt, mgp, mgsa, mgst1, mgst2, mhc, mhc2ta, mhp2, mhs, mhs2, mhs3, mhs4, mhs6, mia, mic10, mic11, mic12, mic17, mic18, mic2, mic2x, mic2y, mic3, mic4, mic7, mica, micb, mid1, midas, mif, mif, mig, mip, mip2a, mip2b, mip3b, mipep, mitf, miwc, mjd, mk, mki67, mkks, mkp2, mkp3, mkpx, mks, mks, mks1, mks2, mla1, mlck, mlf1, mlf2, mlh1, mlk1, mlk3, mll, mll2, mllt1, mllt2, mllt3, mllt4, mllt6, mllt7, mlm, mlm, mln, mlp, mlr, mlrg, mlrw, mls, mltn, mlvar, mlvi2, mlvt, mmac1, mme, mmp1, mmp10, mmp11, mmp12, mmp13, mmp14, mmp15, mmp16, mmp17, mmp19, mmp2, mmp21, mmp22, mmp3, mmp7, mmp8, mmp9, mn, mn, mnb, mnbh, mnda, mng1, mnk, mns, mnt, mocod, mocs1, mocs2, mody1, mody3, mog, mok2, mom1, mos, mot2, mov34, mox1, mox2, mox44, moz, mp19, mpb1, mpd1, mpdz, mpe, mpe16, mpg, mpi, mpif2, mpl, mpllg, mpo, mpp1, mpp2, mpp3, mppb, mpri, mprm, mps2, mps3a, mps3c, mps4a, mpsh, mpts, mpv17, mpz, mr1, mr77, mrbc, mrc1, mre11, mre11a, mrg1, mrgh, mros, mrp, mrp, mrp1, mrpl23, mrs, mrsd, mrsr, mrst, mrx1, mrxl4, mrx2, mrx20, mrx21, mrx23, mrx29, mrx41, mrx48, mrx49, mrx9, mrxa, mrxs1, mrxs2, mrxs3, mrxs4, mrxs5, mrxs6, mrxs8, ms3315, ms336, msg1, msh2, msh3, msh4, msh6, msi1, msk16, msk39, msk41, mslr1, msmb, msn, msr1, mss1, mss4, mss4, msse, mst, mst1, mst1r, mstd, mstn, msud1, msx1, msx2, mt1a, mt1b, mt1e, mt1f, mt1g, mt1h, mt1i, mt1j, mt1k, mt1l, mt1x, mt2, mt2a, mt3, mtacr1, mtap, mtbt1, mtcp1, mterf, mtf1, mth1, mthfc, mthfd, mthfr, mtk1, mtm1, mtmr1, mtmx, mtnr1a, mtnr1b, mtp, mtpa, mtr, mtrns, mtrr, mts, mts, mts1, mts1, mts2, mttf1, mtx, mtxn, mu, muc1, muc2, muc3, muc4, muc5, muc5ac, muc5b, muc6, muc8, mul, mum1, mupp1, musk, mut, mvk, mvlk, mvwf, mwfe, mx, mx1, mx2, mxi1, mxs1, myb, mybl1, mybl2, mybpc1, mybpc2, mybpc3, mybpcf, mybph, myc, mycl1, mycl2, myclk1, mycn, myd88, myf3, myf4, myf5, myf6, myh1, myh10, myh11, myh12, myh1, myh2, myh3, myh4, myh6, myh7, myh8, myh9, myk1, myl, myl1, myl2, myl3, myl4, myl5, mylk, mymy, myo10, myo15, myo1a, myo1c, myo1d, myo1e, myo5a, myo6, myo7a, myo9b, myoc, myod1, myog, myp1, myp2, myp3, myr5, mzf1, n33, nab1, nab2, nabc1, nac1a, naca, nacae, nacp, nadmr, naga, nagc@, naglu, nagr1, naip, namsd, nanta3, nap1l4, nap2, nap2l, napb, naptb, nars, nat1, nat1, nat2, nb, nb4s, nbat, nbc3, nbccs, nbccs, nbia1, nbs, nbs, nbs1, nca, ncad, ncam1, ncan, ncbp, ncc1, ncc2, ncc3, ncc4, ncct, ncf1, ncf2, ncf4, nck, ncl, ncst2, ncx1, ncx2, nd, ndhii, ndn, ndp, ndst1, ndufa1, ndufa2, ndufa5, ndufa6, ndufa7, ndufb8, ndufb9, ndufs1, ndufs2, ndufs4, ndufs7, ndufs8, ndufv1, ndufv2, ndufv3, neb, nec1, nec2, nedd1, nedd2, nedd4, nefh, nefl, negf1, negf2, nell1, nell2, nem1, neo1, nep, net, het1, neu, neu, neud4, neurod, neurod2, neurod3, nf1, nf1a, nf2, nfatc1, nfatc2, nfatp, nfe1, nfe2, nfe2l1, nfe2l2, nfe2u, nfia, nfib, nfic, nfix, nfkb1, nfkb2, nfkb3, nfkbia, nfkbil1, nfrkb, nfya, nfyb, ngal, ngbe, ngfb, ngfg, ngfic, ngfr, ngl, ngn, nhbp, nhcp1, nhcp2, nhel1nhe3, nhe4, nhe5, nhlh1, nhlh2, nhp2l1, nhs, nid, niddm1, ninj1, nipp1, nipsnap1, nipsnap2, nis, nk1r, nkcc1, nkcc2, nkg2, nkg2a, nkg2c, nkg2e, nkg2f, nkhc, nkna, nknar, nknb, nkrp1a, nks1, nksf2, nktr, nkx2a, nkx3.2, nkx3a, nkx6a, nli, nm, nm1, nm23, nmb, nmbr, nmdar1, mndar2a, nmdar2b, nmdar2c, nmdar2d, nmdara1, nme1, nme2, nme4, nmor1, nmor2, nmsl, nmyc, nnat, nmmt, nno1, nog, nol1, nos1, nos2a, nos2b, nos2c, nos3, not, notch1, notch2, notch3, notch4, nov, nov, nov2, nova1, nova3, novp, np, np10, npat, npc, npc1, npd, nph1, nph2, nphl2, nphn, nphp1, nphp2, nphs1, npm1, nppa, nppb, nppc, npps, npr1, npr2, npr3, nps1, npt1, npt2, nptx2, npy, npy1r, npy2r, npy3r, npy5r, npy6r, nqo2, nramp, nramp1, nramp2, nrap, nras, nrb54, nrcam, nrd1, nrf1, nrf1, nrf2, nrgn, nrip1, nrk2, nrl, nrtn, nru, ns1, nsf, nsp, nspl1, nsrd9, nt4, nt5, nt5, ntcp1, ntcp2, ntf3, ntf4, ntf5, nthl1, ntn, ntn, ntn2l, ntrk1, ntrk2, ntrk3, ntrk4, ntrkr1, ntrkr3, nts, ntt, ntt, nuc1, nucb1, numa1, nup214, nup98, nurr1, nvl, nys1, nys2, nysa, oa1, oa2, oa3, oar, oasd, oasl, oat, oatl1, oatl2, oatl3, oatp, oaz, ob, ob10, obf1, obp, obr, oca2, ocm, ocp2, ocrl, ocrl1, oct, oct1, oct1, oct2, oct2, oct3, oct7, octn2, octs3, odc1, oddd, odf1, odg1, odod, ofc1, ofc2, ofc3, ofd1, ofe, og12, ogdh, ogg1, ogr1, ogs1, ogs2, ohds, ohs, oias, oip1, ok, olf1, olfmf, olfr1, olfr2, omg, omgp, omp, on, op2, opa1, opa2, opa3, opca3, opcm1, opd1, opgl, ophn1, opll, opn, oppg, oprd1, oprk1, oprm1, oprt, opta2, optb1, oqtl, or1d2, or1f1, orc1l, orc2l, orc4l, orc5l, orfx, orm1, orm2, orw, osbp, osm, osp, ost, ost48, osx, otc, otf1, otf2, otf3, otm, otof, ots, otx1, otx2, ovc, ovcs, ovol1, ox40, oxa11, oxct, oxt, oxtr, ozf, p, p, p1, p15, p16, p167, p28, p2rx3, p2rx4, p2ry1, p2ry2, p2ry4, p2ry7, p2u, p2x3, p2x4, p2y1, p2y2, p2y4, p3, p40phox, p450c11, p450c17, p450c2a, p450c2d, p450c2e, p450scc, p4ha, p4ha1, p4hb, p5cdh, p79r, pa2g4, pab1, pab2, pabp2, pabpl1, pac1, pac1, pacapr, pace, pace4, paep, paf1, paf2, pafah, pafah1b1, pafah1b2, pafah1b3, paga, pah, pahx, pai1, pai2, paics, pak1, pak3, palb, pals, pam, pang, pap, papa, papa2, pappa, par1, par1, par2, par3, par4, par4, par5, park1, park2, park3, pawr, pax1, pax2, pax3, pax4, pax5, pax6, pax7, pax8, pax9, pbca, pbcra, pbfe, pbgd, pbt, pbx1, pbx2, pbx3, pc, pc1, pc2, pc3, pc3, pcal, pcad, pcap, pcar1, pcbc, pcbd, pcbp1, pcbp2, pcca, pccb, pcdh7, pcdx, pchc, pchc1, pci, pck1, pcl, pclp, pcm1, pcm1, pcmt1, pcna, pcnt, pcolce, pcp, pcp4, pcs, pcsk1, pcsk2, pcsk3, pcsk4, pcsk5, pcsk6, pctk1, pctk3, pcyt1, pdb, pdb2, pdc, pdc, pdcd1, pdcd2, pddr, pde1a, pde1b, pde1b1, pde3b, pde4a, pde4b, pde4c, pde4d, pde5a, pde6a, pde6b, pde6c, pde6d, pde6g, pde6h, pde7a, pdea, pdea2, pdeb, pdeg, pdes1b, pdgb, pdgfa, pdgfb, pdgfr, pdgfra, pdgfrb, pdha1, pdha2, pdhb, pdj, pdk4, pdnp1, pdnp2, pdnp3, pdr, pds, pds1, pdx1, pdyn, pe1, pea15, pebp2a1, pebp2a3, pecam1, ped, ped, pedf, pee, peg1, peg3, pemp, penk, pent, peo, peo1, peo2, pepa, pepb, pepc, pepd, pepe, pepn, peps, per, per2, peta3, pets1, pex1, pex5, pex6, pex7, pf4, pf4v1, pfas, pfbi, pfc, pfd, pfhb1, pfic1, pfic2, pfkfb1, pfkfb2, pfkl, pfkm, pfkp, pfkx, pfl, pfm, pfn1, pfn2, pfrx, pga3, pga4, pga5, pgam1, pgam2, pgamm, pgc, pgd, pgf, pgft, pgk1, pgk2, pgka, pgl, pgl1, pgl2, pgm1, pgm2, pgm3, pgm5, pgn, pgp, pgp1, pgr, pgs, pgt, pgy1, pgy3, pha1, pha2, pha2a, pha2b, phap1, phb, phc, phe1a, phe3, phex, phf1, phhi, phhi, phk, phka1, phka2, phkb, phkd, phkg1, phkg2, phl, phll1, phog, phox1, phox2a, php, php1b, phpx, phyh, pi, pi10, pi3, pi4, pi5, pi6, pi7, pi8, pi9, piga, pigc, pigf, pigh, pigr, pik3c2b, pik3ca, pik3r1, pik4cb, pil, pim1, pin, pin1, pin1l, pip, pip5k1b, pir1, pir51, pit, pit1, pitpn, pitx1, pitx2, pitx3, pjs, pk1, pk120, pk3, pk428, pkca, pkcb, pkcc, pkcg, pkcsl, pkd1, pkd2, pkd4, pkdts, pkhd1, pklr, pkm2, pkp1, pks1, pks1, pks2, pku1, pl, pla2, pla2a, pla2b, pla2g1b, pla2g2a, pla2g4, pla2g4a, pla2g5, pla2l, pla2l, plag1, plagl1, planh1, planh2, planh3, plat, plau, plaur, plb, plc, plc1, plcb3, plcb4, plcd1, plce, plcg1, plcg2, plc1, pld1, plec1, plg, plgf, plg1, pli, pln, plod, plod2, plos1, plp, pls, pls1, plt1, pltn, pltp, plzf, pmca1, pmca2, pmca3, pmca4, pmch, pmchl1, pmchl2, pmd, pmel17, pmi1, pm1, pmm1, pmm2, pmp2, pmp22, pmp35, pmp69, pmp70, pms1, pms2, pmsl1, pmsl2, pmx1, pn1, pnd, pnem, pnkd, pnlip, pnmt, pnoc, pod1, podx1, pof, pof1, pol2rb, pola, polb, pold1, pold2, pole, polg, polr2a, polr2c, polr2e, polr2g, polr2i, polmit, polz, pomc, pon, pon1, pon2, pon3, por, porc, potx, pou1f1, pou2af1, pou2f2, pou3f1, pou3f2, pou3f1, pou3f4, pou4f1, pou4f3, pou5f1, pp, pp14, pp2, pp4, pp5, ppac, ppard, pparg, pparg1, pparg2, ppat, ppbp, ppcd, ppd, ppef1, ppef2, ppfia3, ppgb, pph, pph1, ppia, ppid, ppil1, ppkb, ppks1, ppks2, ppl, ppla2, ppmx, ppnd, ppnoc, ppo1, ppox, ppp1a, ppp1ca, ppp1cb, ppp1cc, ppp1r2, ppp1r5, ppp1r7, ppp1r8, ppp2b, ppp2ca, ppp2cb, ppp2r1b, ppp2r4, ppp2r5a, ppp2r5b, ppp2r5c, ppp2r5d, ppp2r5e, ppp3ca, ppp3cb, ppp3cc, ppp3r1, ppp4c, ppp5c, ppt, ppt2, ppx, ppy, ppyr1, pr@, prad1, prb1, prb2, prb3, prb4, prca1, prca2, prcc, prcp, prelp, prep, prf1, prg, prg1, prg1, prgs, prh1, prh2, prim1, prim2a, prim2b, prip, prk1, prkaa1, prkaa2, prkab1, prkaca, prkacb, prkacg, prkag1, prkag2, prkar1a, prkar1b, prkar2b, prkca, prkcb1, prkcd, prkcg, prkci, prkcl1, prkcnh1, prkcq, prkcsh, prkdc, prkg1, prkg1b, prkg2, prkgr1b, prkgr2, prkm1, prkm3, prkm4, prkm9, prkn, prkr, prkx, prky, pr1, pr1r, prm1, prm2, prmt2, prnp, proa, proc, prodh, prohb, prop1, pros1, pros30, prox1, prph, prph, prps1, prps2, prpsap1, prr1, prr2, prs, prsc1, prss1, prss11, prss2, prss7, prss8, prssl1, prtn3, prts, psa, psa, psach, psap, psbg1, psbg2, psc2, psc5, psca, psd, psen1, psen2, psf1, psf2, psg1, psg11, psg12, psg13, psg2, psg3, psg4, psg5, psg6, psg7, psg8, psgl1, pskh1, psm, psma1, psma2, psma3, psma5, psmb1, psmb10, psmb2, psmb3, psmb4, psmb5, psmb8, psmb9, psmc1, psmc2, psmc3, psmc5, psmd7, psmd9, psme1, psme2, psors1, psors2, psors3, psp, psps1, psps2, pss1, psst, pst, pst, pst1, psti, ptafr, ptc, ptc, ptc, ptch, ptd, pten, ptgds, ptger1, ptger2, ptger3, ptgfr, ptgfrn, ptgir, ptgs1, ptgs2, pth, pth1h, pthr, pthr1, pthr2, ptk1, ptk2, ptk2b, ptk3, ptk7, ptlah, ptma, ptms, ptn, ptos1, ptp18, ptp1b, ptp4a1, ptp4a2, ptpa, ptpa, ptpd, ptpg, ptpg1, ptpgmc1, ptpn1, ptpn10, ptpn11, ptpn12, ptpn13, ptpn14, ptpn2, ptpn5, ptpn6, ptpn7, ptpra, ptprb, ptprc, ptprcap, ptprd, ptpre, ptprf, ptprg, ptprh, ptprj, ptprk, ptprl1, ptprl2, ptpm, ptprn, ptpro, ptprs, ptprz1, ptpt, pts, pts1r, ptxl1ptx3, pujo, pum, pur1, pur1, pura, pvalb, pvr, pvrl1, pvrl2, pvrr1, pvrr2, pvs, pvt1, pwcr, pwp2, pwp2h, pws, pxaaa1, pxe, pxe1, pxf, pxmp1, pxmp11, pxmp3, pxr1, pycr1, pycs, pygb, pyg1, pygm, pyk2, pyst1, pyst2, pzp, qars, qdpr, qin, qm, qpc, qprs, rab, rab1, rab13, rab1a, rab21, rab3a, rab3b, rab4, rab5, rab5a, rab6, rab7, rabgd1a, rabgdib, rabggta, rabggtb, rabif, rac2, rac3, rad1, rad17, rad23a, rad23b, rad51a, rad51c, rad51d, rad51l3, rad52, rad54, rad6a, rad6b, raf1, rafa1, rag1, rag2, rage, rala, ralb, ralgds, ramp, ranbp2l1, ranbp3, rao, rap1a, rap1b, rap1ga1, rap1gds1, rap2a, rap74, rapsn, rara, rarb, rarg, rars, rasa1, rasa2, rasgfr3, rask2, rb1, rbbp2, rbbp5, rbbp6, rbl1, rbl2, rbm1, rbm2, rbm3, rbmy1a1, rbp1, rbp2, rbp3, rbp4, rbp5, rbp56, rbp6, rbq3, rbtn1, rbtnl1, rbtnl2, rca1, rcac@, rcc1, rccp1, rccp2, rcd1, rcd2, rcdp1, rcn1, rcn2, rcp, rcv1, rd, rdbp, rdc7, rdp, rdpa, rdrc, rds, rdt, rdx, reca, recc1, recq1, red1, red2, reg, reg1a, regl, rel, re1a, reln, ren, renbp, rens1, rent1, rep8, req, ret, rev3, rev31, rfc1, rfc2, rfc3, rfc4, rfc5, rfp, rfx1, rfx2, rfx5, rfxank, rfxap, rgc1, rgr, rgs, rgs1, rgs14, rgs16, rgs2, rgs2, rgs3, rgs5, rh50a, rhag, rhbdl, rhc, rhce, rhd, rheb2, rho, rho7, rhogap2, rhogap3, rhoh12, rhoh6, rhoh9, rhok, rhom1, rhom2, rhom3, rieg1, rieg2, rige, rigui, ring1, ring10, ring11, ring12, ring3, ring31, ring4, ring5, ring6, ring7, rip, rip140, riz, rk, rl, rlbp1, rlf, rln1, rln2, rmch1, rmd1, rmrp, rmrpr, rn5s1@, rnase1, rnase2, rnase3, rnase4, rnase5, rnase6, rnasel, rnaseli, rne1, rnf1, rnf3, rnf4, rnf5, rnh, rnpep, rnpu1z, rnr1, rnr2, rnr3, rnr4, rnr5, rns1, rns2, rns3, rns4, rns4, rns4i, rntmi, rnu1, rnu15a, rnu17a, rnu17b, rnu1a, rnu2, rnu3, ro52, rom1, romk1, ron, ror1, rora, rorb, rorc, rorg, ros1, rosp1, rox, rp1, rpl, rp10, rp105, rp11, rp12, rp13, rp14, rp15, rp17, rp18, rp19, rp2, rp22, rp24, rp25, rp3, rp4, rp6, rp7, rp9, rpa1, rpa2, rpa3, rpd311, rpe, rpe65, rp119, rpl22, rpl23a, rpl231, rpl29, rpl30, rpl35a, rpl36a, rpl7a, rpms12, rpn1, rpn2, rpol2, rpsll1, rps14, rps17, rps17a, rps17b, rps17l1, rps17l2, rps18, rps20a, rps20b, rps24, rps25, rps3, rps4x, rps4y, rps6, rps6ka1, rps6ka2, rps6ka3, rps8, rpsm12, rptpm, rpu1, rpx, rrad, rras, rrbp1, rreb1, rrm1, rrm2, rrp, rrp22, rs1, rs1, rsc1a1, rsk1, rsk2, rsk3, rsn, rss, rsts, rsu1, rt6, rtef1, rtkn, rtn1, rtn2, rts, rts, rtt, rws, rxra, rxrb, rxrg, ryr1, ryr2, ryr3, rzrb, rzrg, s100a1, s100a10, s100a11, s100a12, s100a13, s100a2, s100a3, s100a4, s100a5, s100a6, s100a7, s100a8, s100a9, s100b, s100d, s100e, s100l, s100p, s152, s4, s7, saa1, saa2, saa4, sacs, safb, sag, sah, sahh, sai1, sakap84, sall1, sall2, sams1, sams2, sap, sap1, sap1, sap2, sap62, sar, sar1, sar2, sard, sas, sat, satb1, satt, sbma, sc, sc1, sc5dl, sca1, sca10, sca2, sca2, sca3, sca4, sca5, sca6, sca7, sca8, sca8, scar, scca1, scca2, sccd, scd, sceh, scg1, scg2, scg3, schad, scida, scidx, scidx1, scl, sclc1, scll, scn, scn1a, scn1b, scn2a, scn2a1, scn2a2, scn2b, scn3a, scn4a, scn5a, scn6a, scn8a, scnn1a, scnn1b, scnn1d, scnn1g, scot, scp, scp1, scp2, scpn, scra1, scra1, scs, sctr, scya1, scya11, scya13, scya14, scya15, scya16, scya19, scya2, scya21, scya22, scya24, scya25, scya3, scya311, scya4, scya5, scya7, scya8, scyb5, scyb6, scyd1, sczd1, sczd2, sczd3, sczd4, sczd5, sczd6, sczd7, sczd8, sdc1, sdc2, sdc4, sdf1, sdf2, sdh1, sdh2, sdha, sdhb, sdhc, sdhd, sdhf, sds22, sdty3, sdys, se, sea, sec13l1, sec13r, sec14l, sec7, sedl, sedt, sef2, sel11, sele, sell, selp, selplg, sema3f, sema4, sema5, semg, semg1, semg2, sen1, sep, sepp1, serca1, serca3, serk1, ses1, set, sex, sf, sf1, sfa1, sfd, sfmd, sfrs1, sfrs2sfrs7, sftb3, sftp1, sftp2, sftp4, sftpa1, sftpa2, sftpb, sftpc, sftpd, sgb, sgca, sgcb, sgcd, sgcg, sgd, sgk, sglt1, sglt2, sgm1, sgne1, sgp2, sgpa, sgsh, sh2d1a, sh3bp2, sh3d1a, sh3gbr, sh3p17, shb, shbg, shc1, shcl1, shfd1, shfd2, shfm1, shfm2, shfm3, shh, ship, shmt1, shmt2, shoc2, shot, shox, shox2, shps1, shs, shsfl, si, siah1, siah2, siasd, siat1, siat4, siat4c, siat8, sids, sil, silv, sim1, sim2, sipa1, sis, siv, six1, six5, sja, sjs, ski, ski2, ski2w, skiv2l, skp1a, skp1b, skp2, sla, slap, slbp, slc, slc10a1, slc10a2, slc12a1, slc12a2, slc12a3, slc14a1, slc14a2, slc15a1, slc16a1, slc16a2, slc17a1, slc17a2, slc18a1, slc18a2, slc18a3, slc19a1, slc1a1, slc1a2, slc1a3, slc1a4, slc1a5, slc20a1, slc20a2, slc20a3, slc21a2, slc21a3, slc22a1, slc22a2, slc22a5, slc2a1, slc2a2, slc2a3, slc2a4, slc2a5, slc2c, slc3a1, slc4a1, slc4a2, slc4a6, slc5a1, slc5a2, slc5a3, slc5a5, slc6a1, slc6a10, slc6a12, slc6a2, slc6a3, slc6a4, slc6a6, slc6a8, slc6a9, slc7a1, slc7a2, slc7a4, slc7a5, slc7a7, slc8a1, slc8a2, slc9a1, slc9a2, slc9a3, slc9a4, slc9a5, sld, sle1, sleb1, slim1, sln, slo, slos, slp76, sls, slug, sm1, sm22, sma4, smad1, smad1, smad2, smad3, smad4, smad5, smad6, smad7, smad9, sma1, smam1, smarca1, smarca2, smarca3, smarca5, smarcb1, smax2, smc1, smcc, smcr, smcx, smcy, sml1, smn, smn1, smn2, smnr, smo, smoh, smpd1, sms, smt3, smt3h1, smtn, smubp2, sn, snap25, snat, snca, sncb, sncg, snf2h, snf2l1, snf2l2, snf2l3, snf5, sn1, snn, snrp70, snrpa, snrpe, snrpn, snt1, snt2b1, snt2b2, sntb1, snt1, snx, soat, sod1, sod2, sod3, solh, son, sord, sorl1, sosl, sos2, sox1, sox10, sox11, sox2, sox20, sox22, sox3, sox4, sox9, sp1, sp1, sp3, sp3, sp4, spa1, spag1, spag4, spam1, sparc, spat, spbp, spch1, spd, spf30, spg3a, spg4, spg5a, spg6, spg7, spg8, spg9, spgp, spgyla, sph2, spi1, spink1, spk, spmd, spn, spp1, spp2, sppm, spr, sprk, sprr1a, sprr1b, sprr2a, sprr2b, sprr2c, sprr3, sps1, spsma, spta1, sptan1, sptb, sptbn1, sra1, sra2, src, src1, src1, src2, srd5a1, srd5a2, srebf1, srebf2, sri, srk, srm, srn1, srp14, srp19, srp46, srpr, srpx, srs, srvx, sry, ss, ss, ssa, ssa1, ssa2, ssadh, ssav1, ssbp, ssdd, ssr2, ssrc, sst, sstr1, sstr2, sstr3, sstr4, sstr5, ssx1, ssxt, st2, st3, st4, st5, st6, st8, sta, stac, stam, star, stat, stat1, stat3, stat4, stat6, stath, stau, stc, stc1, stch, std, std, ste, step, stfl, stfa, stfb, stgd1, stgd2, stgd3, stgd4, sthe, stk1, stk11, stk15, stk2, stk6, stl, stm, stm2, stm7, stmy1, stmy2, stmy3, stp, stp1, stp2, sts, sts1, stx, stx1b, stx7, stxbp1, stxbp2, sult1c1, supt6h, sur, sur1, surf1, surf2, surf3, surf4, surf5, surf6, svct2, svmt, sw, sxi2, syb1, syb2, sybl1, sycp1, syk, sym1, syn1, syn2, syn3, syngap, syns1, syp, syt, syt1, syt2, syt3, syt4, syt5, t, t3d, taal6, tac1r, tac2, tac2r, tac3, tacr1, tacr2, taf2a, taf2a, taf2d, taf2h, taf2n, tafii100, tagln, tak1, tal1, tal2, taldo1, tam, tan1, tap1, tap2, tapa1, tapbp, tapvr1, tars, tas, task, tat, taut, tax, tax1, taz, tbg, tbp, tbp1, tbs, tbx1, tbx2, tbx3, tbx5, tbxa2r, tbxas1, tc1, tc2, tcbp, tcd, tcea1, tceb1l, tceb3, tcf1, tcf12, tcf13, tcf13l1, tcf14, tcf15, tcf17, tcf19, tef2, tcf20, tcf21, tcf3, tcf4, tcf5, tcf611, tcf612, tcf7, tcf8, tcf9, tcfeb, tcfl1, tcfl4, tcl1, tcl1a, tcl2, tcl3, tcl4, tcl5, tcn1, tcn2, tco, tcof1, tcp1, tcp10, tcp11, tcp228, tcpt, tcra, tcrb, tcrd, tcrg, tcrz, tcs1, tcta, tcte1, tcte3, tctel1, tdf, tdfa, tdfx, tdg, tdgf1, tdn, tdo, tdo2, tdt, tead4, tec, tec, teck, tecta, tef, tegt, tek, tel, tem, tep1, terc, terf1, tert, tes1, tesk1, tex28, tf, tf2, tf6, tfa, tfam, tfap2a, tfap2b, tfap2c, tfap4, tfcoup1, tfcoup2, tfcp2, tfdp1, tfdp2, tfe3, tff1, tff2, tff3, tfiiia, tfm, tfpi, tfpi2, tfr, tfrc, tfs1, tft, tg, tg737, tgb1, tgb2, tgd, tgfa, tgfb1, tgfb2, tgfb3, tgfb4, tgfbi, tgfbr1, tgfbr2, tgfbr3, tgfbre, tgfr, tgm1, tgm2, tgm3, tgm4, tgn38, tgn46, th, thas, thbd, thbp1, thbs1, thbs2, thbs3, thc, thh, th1, thop1, thpo, thr1, thra, thra1, thra1, thrb, thrm, thrsp, thy1, tial1, tiam1, tiar, tic, tie, tie1, tie2, tigr, til, til3, til4, tim, timp, timp1, timp2, timp3, tinur, titf1, titf2, tjp1, tk1, tk2, tkc, tkcr, tkr, tkt, tkt2, tktl1, tla519, tlcn, tle1, tle2, tle3, tlh1, tln, tlr1, tlr2, tlr3, tlr4, tlr5, tm4sf1, tm4sf2, tm7sf2, tmc, tmd, tmdci, tmem1, tmf1, tmip, tmod, tmp, tmpo, tmprss2, tms, tmsa, tmsb, tmvcf, tna, tndm, tnf, tnfa, tnfaip1, tnfaip2, tnfaip4, tnfaip6, tnfar, tnfb, tnfbr, tnfc, tnfcr, tnfr1, tnfr2, tnfrsf10b, tnfrsf12, tnfrsf14, tnfrsf16, tnfrsf17, tnfrsf1a, tnfrsf1b, tnfrsf4, tnfrsf5, tnfrsf6, tnfrsf6b, tnfrsf7, tnfrsf8, tnfrsf9, tnfsf11, tnfsf12, tnfsf5, tnfsf6, tnfsf7, tnnc1, tnnc2, tnii1, tnni2, tnni3, tnnt1, tnnt2, tnnt3, tnp1, tnp2, tnr, tns, tnx, tnxa, toc, top1, top2, top2a, top2b, top3, tp1, tp120, tp250, tp53, tp53bp1, tp63, tp73, tpa, tpbg, tpc, tpc, tph, tph2, tpi1, tpl2, tpm1, tpm2, tpm3, tpm4, tpmt, tpo, tpo, tpp2, tpr, tpr1, tprd, tps1, tps2, tpsn, tpst1, tpst2, tpt, tpt1, tptps, tpx, tpx1, tr, tr2, tr4, tra1, trafl, traf5, trailr2, tran, trance, trap170, trc3, trc8, tre, treb36, trek, trf1, trg1, trh, trhr, tric5, trio, trip1, trip14, trip6, trk, trk1, trka, trkb, trkc, trke, trl1, trl2, trm1, trm1, trm2, trma, trmi1, trmi2, trn, trnl, tro, trp1, trp1, trp2, trp3, trpc1, trpm2, trpo, trps1, trps2, trq1, trr, trr3, trrap, trsp, trt1, trt2, trv1, trv2, trv3, trv4, trv5, try1, try2, ts, ts13, ts546, tsbn51, tsc, tsc1, tsc2, tsd, tse1, tsg101, tsg7, tshb, tshr, tsix, tsp3, tspy, tssc3, tst1, tst1, tsta3, tsy, ttc1, ttc3, ttf, ttf1, ttf2, ttg2, ttim1, ttn, ttp, ttp1, ttpa, ttr, tuba3, tuba11, tubb, tufm, tuft1, tulp1, tuple1, tw, tweak, twik1, twist, txgp11, txk, txn, txnr, txnrd1, tyh, tyk1, tyk2, tyk3, tyms, tyr, tyr1, tyro3, tyrp1, tyrp2, tys, u17hg, u1rnp, u22hg, u2af1, u2af1rs1, u2af1rs2, u2af1rs3, uba52, ubb, ubc, ubc4, ubc7, ubc8, ubch2, ubc1, ube1, ube2, ube2a, ube2b, ube2e2, ube2g, ube2g2, ube2h, ube2i, ube2l1, ube2v1, ube3a, ubh1, ubid4, ubl1, uchl1, ucn, ucp1, ucp2, ucp3, udpgdh, uev1, ufd11, ufs, ugalt, ugb, ugcg, ugdh, ugn, ugp1, ugp2, ugpp2, ugt1, ugt1a1, ugt2b11, ugt2b15, ugt2b17, ugt2b4, ugt2b7, ugt2b8, ugt2b9, ugtl, uhg, uhx1, ukhc, umod, umph2, umpk, umps, unc18, unc18b, und, ung, unr, unr, uox, up, upk1b, ups, uqbp, uqcrb, uqcrc1, uqcrc2, uqcrfs1, uqor1, uqor13, uqor22, urk, urkr, uroc, urod, uros, usf1, usf2, ush1, ush1a, ush1b, ush1c, ush1d, ush1e, ush1f, ush2a, ush3, usp11, usp5, usp7, usp9x, usp9y, ut1, ut2, ute, utr, utrn, utx, uty, uv20, uv24, uvo, vacht, vacm1, vamp1, vamp2, vars1, vasp, vat1, vat2, vav, vav1, vav2, vbch, vbp1, vcam1, vcf, vcl, vcp, vdac1, vdac2, vdd1, vdi, vdr, vegf, vegfb, vegfd, vegfr3, vgf, vgl, vgr1, vhl, vhr, vil1, vil2, vin, vip, vipr1, vipr2, vis1, vla1, vla5a, vlacs, vlcad, vldlr, vmat1, vmcm, vmd1, vmd2, vnra, vnt, vp, vpp1, vpp3, vpreb1, vpreb2, vrf, vrk1, vrk2, vrnf, vrni, vsnl1, vtn, vwf, vws, waf1, wars, was, wbs, wd1, wdr2, wee1, wfrs, wfs, wfs1, wgn1, whcr, wi, wisp1, wisp2, wisp3, wnd, wnt1, wnt10b, wnt13, wnt14, wnt15, wnt2, wnt3, wnt5a, wnt7a, wnt7b, wnt8b, wrb, wrn, ws1, ws2a, ws2b, ws4, wsn, wss, wss, wt1, wt2, wt3, wt4, wt5, wts, wts1, wws, x11, xbp1, xbp2, xce, xdh, xe169, xe7, xe7y, xg, xgr, xh2, xiap, xic, xist, xk, xla, xla2, xlp, xlpd, xlrs1, xm, xpa, xpb, xpc, xpcc, xpct, xpf, xpf, xpg, xpmc2h, xpnpep2, xpo1, xrcc1, xrcc2, xrcc3, xrcc4, xrcc5, xrcc9, xrs, xs, xwnt2, yb1, yes1, ykl40, yl1, yrrm1, yt, ywha1, ywhab, ywhah, ywhaz, yy1, zac, zag, zan, zap70, zf87, zfm1, zfp3, zfp36, zfp37, zfx, zfy, zic1, zic2, zic3, zipk, znf1, znf10, znf117, znf11a, znf11b, znf12, znf121, znf123, znf124, znf125, znf126, znf13, znf14, znf141, znf144, znf146, znf147, znf157, znf16, znf160, znf162, znf163, znf165, znf169, znf173, znf179, znf18, znf189, znf19, znf192, znf193, znf195, znf198, znf2, znf20, znf200, znf204, znf217, znf22, znf23, znf24, znf25, znf26, znf27, znf29, znf3, znf32, znf34, znf35, znf36, znf38, znf4, znf40, znf41, znf42, znf44, znf45, znf46, znf5, znf6, znf69, znf7, znf70, znf71, znf72, znf73, znf74, znf75, znf75a, znf75c, znf76, znf77, znf79, znf8, znf80, znf81, znf83, znf9, znfc150, znfc25, znfxy, znt3, znt4, zp3a, zp3b, zpk, zws1, and zyx.

Furthermore, genes from bacteria, plants, yeast, and mammals (e.g., mice) can be used with the present invention. Examples of *E. coli* genes include: aarF, aas, aat, abpS, abs, accA, accB, accC, accD, acd, aceA, aceB, aceE, aceF, aceK, ackA, ackB, acnA, acnB, acpD, acpP, acpS, acpX, acrA, acrB, acrC, acrD, acrE, acrF, acrR, acs, ada, add, adhB, adhC, adhE, adhR, adiA, adiY, adk, aegA, aer, aes, agaA, agaB, agaC, agaD, agaI, agaR, agaS, agaV, agaW, agaZ, agp, ahpC, ahpF, aidB, ais, alaS, alaT, alaU, alaV, alaW, alaX, aldA, aldB, aldH, alkA, alkB, alpA, alr, alsA, alsB, alsC, alsE, alsK, alx, amiA, amiB, amn, ampC, ampD, ampE, ampG, ampH, amtB, amyA, ansA, ansB, apaG, apaH, aphA, appA, appB, appC, appY, apt, aqpZ, araA, araB, araC, araD, araE, araF, araG, araH, araJ, arcA, arcB, argA, argB, argC, argD, argE, argF, argG, argH, argI, argM, argP, argQ, argR, argS, argT, argU, argV, argW, argY, argZ, aroA, aroB, aroC, aroD, aroE, aroF, aroG, aroH, aroI, aroK, aroL, aroM, aroP, aroT, arsB, arsC, arsR, artI, artJ, artM, artP, artQ, ascB, ascF, ascG, asd, aslA, aslB, asmA, asnA, asnB, asnC, asnS, asnT, asnU, asnV, asnW, aspA, aspC, aspS, aspT, aspU, aspV, asr, asu, atoA, atoB, atoC, atoD, atoS, atpA, atpB, atpC, atpD, atpE, atpF, atpG, atpH, atpI, avtA, azaA, azaB, azl, bacA, baeR, baeS, barA, basR, basS, bax, bcp, bcr, betA, betB, betI, betT, bfd, bfm, bfr, bglA, bglB, bglF, bglG, bglJ, bglT, bglX, bioA, bioB, bioC, bioD, bioF, bioH, bioP, bipA, birA, bisC, bisZ, blc, bolA, brnQ, brnR, brnS-??, brnT, btuB, btuC, btuD, btuE, btuR, bymA, cadA, cadB, cadC, cafA, caiA, caiB, caiC, caiD, caiE, caiF, caiT, calA, calC, calD, can, carA, carB, cbl, cbpA, cbt, cca, ccmA, ccmB, ccmC, ccmD, ccmE, ccmF, ccmG, ccmH, cdd, cde, cdh, cdsA, cdsS, cedA, celA, celB, celC, celD, celF, cfa, cfcA, chaA, chaB, chaC, cheA, cheB, cheR, cheW, cheY, cheZ, chpA, chpB, chpR, chpS, cirA, citA, citB, cld, clpA, clpB, clpP, clpX, cls, cmk, cmlA, cmr, cmtA, cmtB, coaA, cobS, cobT, cobU, codA, codB, cof, cog?, corA, cpdA, cpdB, cpsA, cpsB, cpsC, cpsD, cpsE, cpsF, cpsG, cpxA, cpxB, cpxP, cpxR, crcA, crcB, creA, creB, creC, creD, crg, crl, crp, crr, csdA, csgA, csgB, csgD, csgE, csgF, csgG, csiA, csiB, csiC, csiD, csiE, csiF, cspA, cspB, cspC, cspD, cspE, cspG, csrA, csrB, cstA, cstC, cup, cutA, cutC, cutE, cutF, cvaA(ColV), cvaB(ColV), cvaC(ColV), cvi(ColV), cvpA, cxm, cyaA, cybB, cybC, cycA, cydA, cydB, cydC, cydD, cynR, cynS, cynT, cynX, cyoA, cyoB, cyoC, cyoD, cyoE, cysA, cysB, cysC, cysD, cysE, cysG, cysH, cysI, cysJ, cysK, cysM, cysN, cysP, cysQ, cysS, cysT, cysU, cysW, cysX?, cysZ?, cytR, dacA, dacB, dacC, dacD, dadA, dadB, dadQ, dadX, dam, dapA, dapB, dapD, dapE, dapF, dbpA, dcd, dcm, dcp, dcrB, dctA, dctB, dcuA, dcuB, dcuC, ddlA, ddlB, ddpA, ddpB, ddpC, ddpD, ddpF, ddpX, deaD, dedA, dedD, def, degP, degQ, degS, del, deoA, deoB, deoC, deoD, deoR, dfp, dgd, dgkA, dgkR, dgoA, dgoD, dgoK, dgoR, dgoT, dgsA, dgt, dicA, dicB, dicC, dicF, dinB, dinD, dinF, dinG, dinI, dinY, dipZ, djlA, dksA, dld, dmsA, dmsB, dmsC, dnaA, dnaB, dnaC, dnaE, dnaG, dnaI, dnaJ, dnaK, dnaL, dnaN, dnaQ, dnaT, dnaX, dppA, dppB, dppC, dppD, dppF, dppG, dps, dsbA, dsbB, dsbC, dsbG, dsdA, dsdC, dsdX, dsrA, dsrB, dut, dvl, dxs, ebgA, ebgB, ebgC, ebgR, ecfA, eco, ecpD, eda, edd, efp, emrA, emrB, emrD, emrE, endA, eno, entA, entB, entC, entD, entE, entF, envN-??, envP, envQ, envR, envT, envY, envZ, epd, EppA, minigene, EppB, minigene, EppC, minigene, EppD, minigene, EppE, minigene, EppG, minigene, EppH, minigene, era, esp, evgA, evgS, exbB, exbC, exbD, expA, exuR, exuT, fabA, fabB, fabD, fabF, fabG, fabH, fabI, fabZ, fadA, fadB, fadD, fadE, fadH, fadL, fadR, farR, fatA, fbaA, fbaB, fbp, fcl, fcsA, fdhD, fdhE, fdhF, fdnG, fdnH, fdnI, fdoG, fdoH, fdoI, fdrA, fdx, feaB, feaR, fecA, fecB, fecC, fecD, fecE, fecI, fecR, feoA, feoB, fepA, fepB, fepC, fepD, fepE, fepG, fes, fexB, ffh, ffs, fhlA, fhlB, fhuA, fhuB, fhuC, fhuD, fhuE, fhuF, fic, fimA, fimB, fimC, fimD, fimE, fimF, fimG, fimH, fimI, fipB, fipC, fis, fiu, fixA, fixB, fixC, fixX, fklB, fkpA, fldA, flgA, flgB, flgC, flgD, flgE, flgF, flgG, flgH, flgI, flgJ, flgK, flgL, flgM, flgN, flhA, flhB, flhC, flhD, fliA, fliC, fliD, fliE, fliF, fliG, fliH, fliI, fliJ, fliK, fliL, fliM, fliN, fliO, fliP, fliQ, fliR, fliS, fliT, fliy, fliz, flk, flu, fmt, fnr, focA, focB, folA, folC, folD, folE, folK, folP, folX, fpr, frdA, frdB, frdC, frdD, frr, fruA, fruB, fruK, fruR, fsr, ftn, ftsA, ftsE, ftsI, ftsJ, ftsK, ftsL, ftsN, ftsQ, ftsW, ftsX, ftsY, ftsZ, fucA, fucI, fucK, fucO, fucP, fucR, fumA, fumB, fumC, fur, fusA, fusB, gabC-??, gabD, gabP, gabT, gadA, gadB, gadR, galE, galF, galK, galM, galP, galR, galS, galT, galU, gapA, gapC, garA, garB, gatA, gatB, gatC, gatD, gatR, gatY, gatZ, gcd, gcl, gcpE, gcvA, gcvH, gcvP, gcvR, gcvT, gdhA, gef, ggt, gidA, gidB, gip, glcB, glcC, glcD, glcE, glcG, gldA, glf, glgA, glgB, glgC, glgP, glgS, glgX, glk, glmM, glmS, glmU, glmX, glnA, glnB, glnD, glnE, glnG, glnH, glnK, glnL, glnP, glnQ, glnR, glnS, glnT, glnU, glnV, glnW, glnX, gloA, glpA, glpB, glpC, glpD, glpE, glpF, glpG, glpK, glpQ, glpR, glpT, glpX, gltA, gltB, gltD, gltE, gltF, gltH, gltJ, gltK, gltL, gltM, gltP, gltR, gltS, gltT, gltU, gltV, gltW, gltX, glyA, glyQ, glyS, glyT, glyU, glyV, glyW, glyX, glyY, gmd, gmk, gmm, gnd, gntK, gntP, gntR, gntS, gntT, gntU, gntV, goaG, gor, gph, gpmA, gpp, gprA, gprB, gpsA, gpt, greA, greB, groL, groS, grpE, grxA, grxB, grxC, gshA, gshB, gsk, gsp, gsp*, gst, guaA, guaB, guaC, gurB, gurC, gutM, gutQ, gyrA, gyrB, hcaB, hcaC, hcaD, hcaE, hcaF, hcaR, hcaT, hdeA, hdeB, hdeD, hdhA, helD, hemA, hemB, hemC, hemD, hemE, hemF, hemG, hemH, hemK, hemL, hemM, hemX, hemY, hepA, het, hflB, hflC, hflK, hflX, hfq, hha, hipA, hipB, hisA, hisB, hisC, hisD, hisF, hisG, hisH, hisI, hisJ, hisM, hisP, hisQ, hisR, hisS, hlpA, hlyE, hmp, hns, holA, holB, holC, holD, holE, hopB, hopC, hopD, hpt, hrpA, hrpB, hrsA, hscA, hscB, hsdM, hsdR, hsdS, hslC, hslD?, hslE-H, hslJ, hslK, hslL-N, hslO-R, hslU, hslV, hslW, htgA, htpG, htpx, htrB, htrC, htrE, htrL, hupA, hupB, hyaA, hyaB, hyaC, hyaD, hyaE, hyaF, hybA, hybB, hybC, hybD, hybE, hybF, hybG, hycA, hycB, hycC, hycD, hycE, hycF, hycG, hycH, hycI, hydA, hydG, hydH, hydN, hyfA, hyfB, hyfC, hyfD, hyfE, hyfF, hyfG, hyfH, hyfI, hyfJ, hyfR, hypA, hypB, hypC, hypD, hypE, hypF, iadA, iap, ibpA, ibpB, icd, iclR, ihfA, ihfB, ileR, ileS, ileT, ileU, ileV, ileX, ileY, ilvA, ilvB, ilvC, ilvD, ilvE, ilvF, ilvG, ilvH, ilvI, ilvJ-??, ilvM, ilvN, ilvR, ilvU, ilvY, imp, inaA, inaR?, infA, infB, infc, inm, insA(IS1), intA, isb(IS1), isfA, ispA, ispB, KanR, katE, katG, kba, kbl, kch, kdgK, kdgR, kdgT, kdpA, kdpB, kdpC, kdpD, kdpE, kdpF, kdsA, kdsB, kdtA, kdtB, kefB, kefC, kgtP, ksgA, ksgB, ksgC, ksgD, lacA, lacI, lacY, lacZ, lamB, lar, ldcC, ldhA, lepA, lepB, leuA, leuB, leuC, leuD, leuJ, leuO, leuP, leuQ, leuR, leuS, leuT, leuU, leuV, leuW, leuX, leuY, leuZ, lev, lexA, lgt, lhr, ligA, ligT, linB, lipA, lipB, lit, livF, livG, livH, livJ, livK, livM, lldD, lldP, lldR, lolA, lon, lpcA, lpcB, lpd, lplA, lpp, lpxA, lpxB, lpxC, lpxD, lpxK, lrb, lrhA, lrp, lrs-??, lspA, lysA, lysC, lysP, lysQ, lysR, lysS, lysT, lysU, lysV, lysW, lysX, lysY, lysZ, lytA, lytB, lyx, maa, mac, mae, mafA, mafB, malE, malF, malG, malI, malK, malM, malP, malQ, malS, malT, malX, malY, malZ, manA, manC, manX, manY, manZ, map, marA, marB, marR, mbrB, mcrA, mcrB, mcrC, mcrD, mdaB, mdh, mdoB, mdoG, mdoH, meb, melA, melB, melR, menA, menB, menC, menD, menE, menF, mepA, mesJ, metA, metB, metC, metD, metE, metF, metG, metH, metJ, metK, metL, metR, metT, metU, metV, metW, metY, metZ, mfd, mglA, mglB, mglC, mglR, mgsA, mgtA, mhpA, mhpB, mhpC, mhpD, mhpE, mhpF, mhpR, miaA, miaD, micF, minC, minD, minE, mioC, mltA, mltB, mltC, mltD, mmrA(rhlB?), mng, mntA, moaA, moaB, moaC, moaD, moaE, mobA, mobB, moc, modA, modB, modC, modE, modF, moeA, moeB, mog, molR, motA, motB, mpl, mppA, mprA, mraA-?, mraY, mrcA, mrcB, mrdA, mrdB, mreB, mreC, mreD, mrp, mrr, msbA, msbB, mscL, msrA, msyB, mtg, mtgA, mtlA, mtlD, mtlR, mtr, mttA, mttB, mttC, mukB, mukE, mukF, mul, murA, murB, murC, murD, murE, murF, murG, murH, murI, mutG(putative), mutH, mutL, mutM, mutS, mutT, mutY, nac, nadA, nadB, nadC, nadE, nagA, nagB, nagC, nagD, nagE, nalB, nalD, nanA, nanE, nanK, nanR, nanT, napA, napB, napC, napD, napF, napG, napH, narG, narH, narI, narJ, narK, narL, narP, narQ, narU, narV, narW, narX, narY, narZ, ndh, ndk, neaB, nei, nemA, nfi, nfnA, nfnB, nfo, nfrA, nfrB, nfrD, nfsA, nhaA, nhaB, nhaR, nikA, nikB, nikC, nikD, nikE, nirB, nirC, nirD, nlpA, nlpB, nlpC, nlpD, nmpC(qsr'), non, npr, nrdA, nrdB, nrdD, nrdE, nrdF, nrdG, nrfA, nrfB, nrfC, nrfD, nrfE, nrfF, nrfG, nth, ntpA, nuoA, nuoB, nuoC, nuoE, nuoF, nuoG, nuoH, nuoI, nuoJ, nuoK, nuoL, nuoM, nuoN, nupC, nupG, nusA, nusB, nusG, nuvA, nuvC, ogrK, ogt, ompA, ompC, ompF, ompG, ompR, ompT, ompX, oppA, oppB, oppC, oppD, oppE, oppF, opr, ops, oraA, ordL, orf-23(purB, reg) orf195(nikA-reg), orn, osmB, osmC, osmE, osmY, otsA, otsB, oxyR, oxyS, pabA, pabB, pabC, pac, pal, panB, panC, panD, panF, parC, parE, pat, pbpG, pck, pcm, pcnB, pdhR, pdxA, pdxB, pdxH, pdxj, pdxK, pdxL, pdxY, pepA, pepD, pepE, pepN, pepP, pepQ, pepT, pfkA, pfkB, pflA, pflB, pflC, pflD, pfs, pgi, pgk, pgl, pgm, pgpA, pgpB, pgsA, pheA, pheP, pheS, pheT, pheU, pheV, phnC, phnD, phnE, phnF, phnG, phnH, phnI, phnJ, phnK, phnL, phnM, phnN, phnO, phnP, phoA, phoB, phoE, phoH, phoP, phoQ, phoR, phoU, phrB, phxB, pin, pioO, pit, pldA, pldB, plsB, plsC, plsX, pmbA, pncA, pncB, pnp, pntA, pntB, pnuC, poaR, polA, polB, popD, potA, potB, potC, potD, potE, potF, potG, potH, potI, poxA, poxB, ppa, ppc, pphA, pphB, ppiA, ppiB, ppiC, ppk, pppA, pps, ppx, pqiA, pqiB, pqqL, pqqM, prc, prfA, prfB, prfC, priA, priB, priC, prlC, prlZ, prnA, prmB, proA, proB, proC, proK, proL, proM, proP, proQ, proS, proT, proV, proW, proX, prpA, prpC, prpR, prr, prs, psd, psiF, pspA, pspB, pspC, pspE, pspF, pssA, pssR, pstA, pstB, pstC, pstS, psu, pta, pth, ptrA, ptrB, ptsG, ptsH, ptsI, ptsN"-", ptsP, purA, purB, purC, purD, purE, purF, purH, purK, purL, purM, purN, purP, purR, purT, purU, pus, putA, putP, pykA, pykF, pyrB, pyrC, pyrD, pyrE, pyrF, pyrG, pyrH, pyrI, qmeC, qmeD, qmeE, qor, queA, racC, racR, radA, radC, ranA, rarD, ras, rbfA, rbn, rbsA, rbsB, rbsC, rbsD, rbsK, rbsR, rcsA, rcsB, rcsC, rcsF, rdgA, rdgB, recA, recB, recC, recD, recE, recF, recG, recJ, recN, recO, recQ, recR, recT, relA, relB, relE, relF, relX, rep, rer, rfaB, rfaC, rfaD, rfaF, rfaG, rfaH, rfaI, rfaJ, rfaK, rfaL, rfap, rfaQ, rfaS, rfaY, rfaZ, rfbA, rfbB, rfbC, rfbD, rfbX, rfc, rfe, rffA, rffC, rffD, rffE, rffG, rffH, rffM, rffT, rhaA, rhaB, rhaD, rhaR, rhaS, rhaT, rhlB, rhlE, rho, ribA, ribB, ribC, ribD, ribE, ribF, ridA, ridB, rimB, rimC, rimD, rimE, rimG, rimH, rimI, rimJ, rimK, rimL, rimM, rit, rlpA, rlpB, rluA, rluC, rluD, rmf, rna, rnb, rnc, rnd, rne, rnhA, rnhB, rnk, rnpA, rnpB, rnr, rnt, rob, rorB, rpe, rph, rpiA, rpiB, rpiR, rplA, rplB, rplC, rplD, rplE, rplF, rplI, rplJ, rplK, rplL, rplM, rplN, rpelO, rplP, rplQ, rplR, rplS, rplT, rplU, rplV, rplW, rplX, rplY, rpmA, rpmB, rpmC, rpmD, rpmE, rpmF, rpmG, rpmH, rpmI, rpmJ, rpoA, rpoB, rpoC, rpoD, rpoE, rpoH, rpoN, rpoS, rpoZ, rpsA, rpsB, rpsC, rpsD, rpsE, rpsF, rpsG, rpsH, rpsI, rpsJ, rpsK, rpsL, rpsM, rpsN, rpsO, rpsP, rpsQ, rpsR, rpsS, rpsT, rpsU, rrfA, rrfB, rrfC, rrfD, rrfE, rrfF, rrfG, rrfH, rrlA, rrlB, rrlC, rrlD, rrlE, rrlG, rrlH, rrmA, rrsA, rrsB, rrsC, rrsD, rrsE, rrsG, rrsH, rsd, rseA, rseB, rseC, rspA, rspB, rssA, rssB, rsuA, rtcA, rtcB, rtcR, rtn, rus(qsr'), ruvA, ruvB, ruvC, sad, sanA, sapA, sapB, sapC, sapD, sapF, sbaA, sbcB, sbcC, sbcD, sbmA, sbmC (gyrI), sbp, sdaA, sdaB, sdaC, sdhA, sdhB, sdhC, sdhD, sdiA, sds, secA, secB, secD, secE, secF, secG, secY, selA, selB, selC, selD, semA, seqA, serA, serB, serC, serR-??, serS, serT, serU, serV, serW, serX, sfa, sfcA, sfiC, sfsA, sfsB, shiA, sipC, sipD, sir, sixA, sloB, slp, slr, slt, slyD, slyX, smp, smtA, sodA, sodB, sodC, sohA, sohB, solA, soxR, soxS, speA, speB, speC, speD, speE, speF, speG, spf, spoT, sppA, spr, srlA, srlB, srlD, srlE, srlR, srmB, srnA, ssaE, ssaG, ssaH, ssb, sseA, sseB, sspA, sspB, ssrA, ssrS, ssyA, ssyD-??, stfZ, stkA, stkB, stkC, stkD, stpA, strC, strM, stsA, sucA, sucB, sucC, sucD, sufI, sugE, suhA, suhB, sulA, supQ, surA, surE, syd, tabC, tag, talA, talB, tanA, tanB, tap, tar, tas, tauA, tauB, tauC, tauD, tbpA, tdcA, tdcB, tdcC, tdcD, tdcE, tdcF, tdcG, tdcR, tdh, tdi-??, tdk, tehA, tehB, tesA, tesB, tgt, thdA, thdC, thdD, thiB?, thiC, thiD, thiE, thiF, thiG, thiH, thiI, thiJ, thiK, thiL, thiM, thrA, thrB, thrC, thrS, thrT, thrU, thrV, thrW, thyA, tig, tktA, tktB, tldD, tlnA, tmk, tnaA, tnaB, tnaC, tnm, tol-orf1, tol-orf2, tolA, tolB, tolC, tolD, tolE, tolI, tolJ, tolM, tolQ, tolR, tonB, topA, topB, torA, torC, torD, torR, torS, torT, tpiA, tpr, tpx, treA, treB, treC, treF, treR, trg, trkA, trkD, trkG, trkH, trmA, trmB, trmC, trmD, trmE, trmF, trmH, trmU, trnA, trpA, trpB, trpC, trpD, trpE, trpR, trpS, trpT, truA, truB, trxA, trxB, trxC, tsaA, tsf, tsmA, tsr, tsx, ttdA, ttdB, ttk, tufA, tufB, tus, tynA, tyrA, tyrB, tyrP, tyrR, tyrS, tyrT, tyrU, tyrV, ubiA, ubiB, ubiC, ubiD, ubiE, ubiF, ubiG, ubiH, ubiX, ucpA[ ], udk, udp, ugpA, ugpB, ugpC, ugpE, ugpQ, uhpA, uhpB, uhpC, uhpT, uidA, uidB, uidR, umuC, umuD, ung, upp, uppS, ups, uraA, usg-1, ushA, uspA, uup, uvh, uvrA, uvrB, uvrC, uvrD, uvs, uxaA, uxaB, uxaC, uxuA, uxuB, uxuR, valS, valT, valU, valV, valW, valX, valY, valZ, vsr, wrbA, xapA, xapB, xapR, xasA, xerC, xerD, xni, xseA, xseB, xthA, xylA, xylB, xylE, xylF, xylG, xylH, xylR, yccA, yhhP, yihG, yjaB, fl47, yjaD, yohF, yqiE, yrfE, zipA, zntA, znuA, znuB, znuC, zur, and zwf.

Examples of mouse genes include: Ilr1, Ilr2, Gas10, Tnp1, Inhbb, Inha, Creb1, Mpmv34, Acrd, Acrg, Il10, Otf1, Rab11b-r, Ab11, ald, Amh-rs1, Bcl2B, Cchl1a3, Ccnb1-rs2, Gpcr16, Htr5b, Idd5, Igfbp2, Igfbp5, Il8rb, Kras2-rs1, Mov7, Mpmv6, Mpmv16, Mpmv22, Mpmv25, Mpmv29, Mpmv42, Mtv7, Mtv27, Mtv39, Oprk1, Otf3-rs1, Otf8, Otfl1-rs1, Ptgs2, Ren1, Ren2, Ril3, Sxv, Taz4-rs1, Tgfb2, Wnt6, Xmmv6, Xmmv9, Xmmv36, Xmmv61, Xmmv74, Xmv21, Xmv32, Xmv41, Il2ra, Abl, Mpmv3, Rap1a-ps2, anx, Mpmv43, Ryr3, Rasl2-4, Adra2b, Avp, Glvr1, Il1a, Il1b, Mpmv28, Oxt, Pcsk2, a, Xmv10, Tcf4, Acra, Acra4, Ak1, Bdnf, bs, Cyct, Cyp24, Dbh, Fshb, Gcg, Gdf5, Gnas, Gpcr8, Grin1, Hcs4, Hior2, Hsp84-2, Idd12, Ilrn, Jund2, Kras3, Mc3r, Mpmv14, Mtv40, Mxi1-rs1, Otf3-rs2, Ptgs1, Ptpra, Rapsn, Src, Svp1, Svp3, Tcf3b, Wt1, Xmmv71, Xmv48, Ccna, Fgf2, Fth-rs1, Csfm, Mov10, Egf, Acrb2, Capl, Crh, Fim3, Fpsl1, Glut2, Gpcr2, Gria2, Hsd3b-1, Hsd3b-2, Hsd3b-3, Hsd3b-4, Hsp86-ps2, Idd3, Il2, Il7, Mpmv9, Mpmv20, Mtv4.8, Ngfb, Npra, Nras, Nras, Ntrk, Otf3-rs3, Otf3-rs4, Rap1a, Tshb, Xmmv22, Xmmv65, Mos, Rasl2-7, Lyr, Ifa, Ifb, Jun, azh, db, Ipp, Mpl, Do1, Ak2, Ccnb1-rs4, Cdc211, Cga, Fgr, Foc1, Fpsl2, Gabrr1, Gabrr2, Gdf6, Glut1, Gnb1, Gpcr14, Grb2-ps, Grik3, Grik5, Hsp86-1ps4, Htr1da, Htr1db, Idd9, Ifa1, Ifa2, Ifa3, Ifa4, Ifa5, Ifa6, Ifa7, Ifa8, Ifa9, Ifa10, Lap18, Lmyc1, Mpmv19, Mpmv44, Mtv13, Mtv14, Mtv17, Nppb, Otf6, Otf7, Ril2, Ski, Tnfr2, Wnt4, Xmmv8, Xmmv23, Xmmv62, Xmv1, Xmv2, Xmv8, Xmv9, Xmv14, Xmv44, Xpa, Tec, Fgf5, Nos1, Tcfl, Epo, Gnb2, Flt1, Flt3, Ache, Adra2c, Adrbk2, Afp, Alb1, Ccnb1-rs1, Clock, Cyp3, Cyp3a11, Cyp3a13, Drd1b, Drd5, Fgfr3, Flk1, Gc, Gchr, Gpcr1, Hcs5, Hnfl, Htr5a, Il5r, Il6, Kit, Ltrm3, Mgsa, Mpmv7, Mpmv13, Mpmv23, Mtv32, Mtv41, Pdgfa, Pdgfra, Por, Txk, Xmmv3, Xmmv5, Xmmv52, Xmv17, Xmv28, Xmv34, Xmv38, Xmv45, Zp3, Trh, Rafl, Fth-rs2, Ntf3, Kras2, Pth1h, Mov1, Alox5, Braf2, Cftr, Egr4, Fpsl10, Fgf6, Gdf3, Ghrfr, Glut3, Grin2a, Hior3, Hoxa10, hop, Ica1, Il5r, Int41, Itpr1, Krag, Mad, Met, Mi, Mtv8, Mtv23, Mtv29, Mtv33, Mtv34, Nkna, Npy, ob, Otf3-rs5, Tgfa, Tnfr1, Wnt2, Wnt5B, Wnt7A, Xmmv27, Xmv24, Xmv61, Fosb, Ryr1, Ngfa, Ufo, Xrcc1, Abpa, Abpga, Gabra4, Gas2, Acra7, Ccnb1-rs7, Egfbp3, Xmv30, Zp2, Fes, Pcsk3, Calc, Ccnb1-rs10, Pth, Ad, Bcl3, Cea, Cea2, Cea3, Cea4, Cea5, Cea6, Cebp, Dm9, Dm15, Drd4, Egfbp1, Egfbp2, Ercc2, Fgf3, Fgfr2, Gabra5, Gabrb3, Gtx, Hcs1, Igflr, Igf2, Il4r, Ins2, Int40, Lhb, Mpmv1, Mtv1, Mtv35, Ngfg, Ntf5, Otf2, 2, Pkcc, Rasl4, Rras, Ryr, Svp2, Tcf3g, Tgfb1, tub, Xmmv31, Xmmv35, Xmmv73, Xmv33, Xmv53, Taz83, Adrb3, Junb, Jund1, Mel, Gpcr19-rs2, Agt, Cadp, Ccnb1-rs9, E, Fgfr1, Gas6, Gnb-rs1, Hcs2, Insr, Maf, Mov34, Mpmv21, Mpmv41, Mtv21, Mtnr1a, Plat, Rasl5-2, Rasl6, Sntb2, Xmmv29, Xmv12, Xmv26, Xmv62, Epor, Gpcr13, Otfl1, Pthr, Acra3, Acra5, Acrb4, Camkl, Cdc25Mm, Crbp, Crbp2, Csk, Cyp11a, Cyp19, Drd2, Ets1, Fli1, Gnai1, Gnat1, Gpcr6, Gria4, Hgfl, Hior1, Hpx, Hsp86-1ps3, Hst2, Idd2, Il1bc, Lagrs1, Lap18-rs1, M11, Mpmv27, Penk, Pgr, Rasl2-2, Tp11, Trf, Xmmv2, Xmmv67, Xmv15, Xmv16, Xmv25, Xmv60, Mgf, Amh, Braf, Cdc2a, Dmdl, Estr, Fpsl3, Fpsl4, Fpsl5, Gli, Gpcr17, Grik2, Ifgr, Igfl, Mpmv5, Mpmv12, Mpmv40, Myb, Oprm, Pg, Pmch, Ros1, Xmv31, Xmv51, Xmv54, Camk2b, Egfr, Int6, Lif, Mtv44, Ews, Csfgm, Flt4, Il3, Il4, Il5, Irfl, Gria1, Glut4, Crhr, Csfg, Mov9, Xmv20, Acrb, Mpmv4, Mpmv15, Ngfr, Nos2, Rara, Taz4, Tcf2, Xmv42, Mtv3, Adra1, Crko, df, Erbb2, Gabra1, Gabra6, Gabrg2, Gh, Glra1, Grb2, Hnflb, Hsp86-ps1, Idd4, Igfbp1, Igfbp3, Il13, Int4, Mpmv2, Mpmv8, Mpmv18, Mtv45, nu, Pkca, Rab1, Rel, Shbg, Tcf7, Thra, Tnz1, Trp53, Wnt3, Wnt3A, Xmv4, Xmv5, Xmv47, Xmv49, Xmv63, Akt, Amh-rs4, Ccs1, Fps16, Fos, Gdf7, Hcs3, Hsp70-2, Hsp84-3, Hsp86-1, hyt, Ltrm1, Max, Mpmv11, Mpmv24, Mtv9, Mtv30, Pomc1, Tcf3a, Tda2, Tgfb3, Tpo, Tshr, Xmmv21l, Xmmv25, Xmmv34, Xmmv50, Gli3, Xmv55, Ryr2, Inhba, Gas1, Pcsk1, Amh-rs2, Ccnb1-rs6, Ccnb1-rs13, Crhpb, Dat1, Drd1a, Fgfr4, Fpsl7, Fim1, Gpcr15, Gpcr18, Hbvi, Hilda, Htr1a, Idd11, Il9, Ltrm4, Mak, mes, Pl1, Pl2, Prl, Ral, Rasa, Srd5a1, Tpbp, Xmv13, Xmv27, Rarb, Rbp3, Htr2, Rb1, Acra2, Camkg, Cchl1a2, Ccnb1-rs5, Ccnb1-rs12, Gnrh, Mtv11, Nras-ps, Otf3-rs6, Plau, Ptprg, Myc, Trp53-ps, Wnt5A, Xmv19, Ghr, Il7r, Lifr, Mlvi2, Prlr, Myc, Ril1, cog, Amh-rs7, Il2rb, Pdgfb, Acr, CP2, Rarg, Sp1-1, Wnt1, Afr1, Atf4, Bzrp, Ccnb1-rs11, Cyp11b, Il3rb1, Il3rb2, Ins3, Itga, Mlvi1, Mlvi3, Mtv36, Pdgfec, Svp5, Tef, Trhr, Wnt7B, Xmmv55, Xmmv72, Xmv37, Tnp2, Ets2, Casr, Chuck-rs1, din, Drd3, Erg, G22p1, Gap43, Gas4, Grik1, Htr1f, Ifgt, Int53, Ltrm2, Mpmv17, Mtv6, Mtvr1, Pit1, Xmv3, Xmv35, Xmv50, Igf2r, Mas, Tcd3, Glp1r, Idd1, Tla, Aeg1, Ccnb1-rs3, Cdc2b, Csi, Cyp21, Cyp21-ps1, Fps18, Gna-rs1, Gpcr19-rs1, Grr1, Grr2, Hom1, Hsc70t, Hsp70, Hsp70-1, Hsp70-3, Hsp84-1, Hst1, Hst4, Hst5, Hst6, Hye, Int3, Itpr3, Lap18-rs2, Otf3, Ptprs, Rab11b, Rasl2-1, Rasl2-3, Rasl3, Rrs, Rxrb, Tas, Tcd1, Tcd2, Tera1, Tla-rs, Tnfa, Tnfb, Tpx1, Tpx2, Xmmv15, Xmv36, Xmv57, Csfmr, Pdgfrb, Adrb2, Apc, Camk2a, Camk4, Dcc, Fgf1, Gnal, Gpcr7, Grl1, Grp, Hsp74, Mcc, Mtv2, Mtv38, Ptpn2, Tpl2, Xmv22, Xmv23, Xmv29, Fth, Csfgmra, Mxi1, Adra2a, Adrb1, Adrbk1, Chuck, Cyp17, Gna14, Gnb-ps1, Hcs6, Htr7, Ide, Ins1, Lpc1, Pomc2, Seao, Tlx1, Xmmv42, Xmv18, Tcfe3, Araf, Avpr2, mdx, Ar, Zfx, Otf9, Ccg1, Ccnb1-rs8, Fps19, Gabra3, Glra2, Glra4, Gria3, Grpr, Hsp74-ps1, Hst3, Htr1c, Il2rg, Mov14, Mov15, Mtv28, Otf3-rs8, Sts, Sxa, Sxr, Xta, Tdy, Hya, Zfy1, Zfy2, Mov15, Mov24, Mtv31, Mtv42, Sdma, Spy, Sts, Sxa, Sxr, XmmvY, Xmv7, Xmv11, and Xmv40.

Examples of *Phaseolus vulgaris* genes include: Acc, ace, Adk, Am, Amv-1, Amv-2, Ane, aph, Arc, Are, arg, Arl (Arc), asp, B, bc-u, bc-1$^1$, bc-1$^2$, bc-2$^1$, bc-2$^2$, bc-3, Bcm, Beg, Bip, blu, Bpm, Bsm, By-1, By-2, C, C/c, c$^{cr}$, C$^{cir}$, C$^{ma}$ (M, R$^{ma}$), C$^r$, C$^{res}$, C$^{rho}$, C$^{st}$, [C$^{St}$R Acc] (Aeq), c$^u$ (inh, i$_e$), [c$^u$ Prp$^i$] (Prp, c$^{ui}$, Nud), [c$^u$prp$^{st}$] (prp$^{st}$), [C Prp] (Prp), c$^v$, [C R] (R), [C r] (r), Ca, Cam, Cav, cc, chl, cl, cml, Co-1 (A), Co-2 (Are), Co-3 (Mexique 1), Co-3$^2$, Co-4 (Mexique 2), Co-5 (Mexique 3), Co-6, Co-7, cr-1 cr-2, cry, cs, Ct, ctv-1 ctv-2, cyv (by-3), D (Can, Ins), Da, Db, def, dgs (gl, le), dia, Diap-1, Diap-2, diff, dis, Dl-1Dl-2 (DL$_1$ DL$_2$), do, ds (te), dt-1$^a$ dt-2$^a$, dt-1$^b$ dt-2$^b$, dw-1 dw-2, Ea Eb, ers (restr), ers-2, Est-1, Est-2, exp, F, Fa, fast, Fb Fc, fa fb fc, Fcr, Fcr-2, fd, Fe-1 Fe-2, Fin (in), Fop-1, Fop-2, Fr, Fr-2, G (Flav, Ca, Och), Ga, gas, glb, Gpi-c1, Gr, Hbl (L$_{HB-1}$), Hbnc (SC$_{HB-1}$), Hbp (PD$_{HB-1}$), hmb, Hss, Hsw, Ht-1Ht-2 (L-1 L-2), I, Ia Ib, ian-1 ian-2 (ia), lbd, ico, Igr (Ih), ilo, ip, iter, iv, iw, J(Sh), Ke, L, la, Lan, Ld, Lds (Ds), Lec, Li (L), lo, lr-1 lr-2, mar, Me, Mel (Me), Mel-2 (Me-2), mel-3 (me-3), Mf, mi, mia, Mic (Mip), miv, Mrf, Mrf$^2$, mrf, ms-1, Mue, mu mutator, Nag, Nd-1 Nd-2 (D-1 D-2), nie, nnd (sym- 1), nnd-2, No, nts (nod), Nudus, ol, P, p$^{gri}$ (Gri, v$^{pal}$), pa, pc, pg (pa$_1$), Pha, Pmv, ppd (neu), Pr, prc (pc), Prx, punc, ram, Rbcs (rbcS), rf-1, rf-2, rf-3, rfi (i), Rfs (m), Rk, rk, rk$^d$ (lin), rn-1 m-2 (r r☐), rnd, Ro, Sal, sb, sb$^{ms}$, sb-2, sb-3, sil, Skdh, sl, Smv, St, Sur, sw-1 sw-2, T, t (z-1), Th-1 Th-2, Tm, To, Tor (T), Tr, tri, trv, Ts, tw, uni, Uni-2, uni$^{nde}$, uni$^{nie}$, Ur-1, Ur-2, Ur-2$^2$, Ur-3 (Ur-3, Ur-4), Ur-3$^2$, Ur-4 (p-2, Ur-C), Ur-5 (B-190), Ur-6 (Ur$_a$, Ur-G), Ur-7 (R$_{B11}$), Ur-8 (Up-1), Ur-9 (Ur$_p$), us, V(Bl), v$^{lac}$ (Cor), v, var, vi (vir$_f$), wb, Wmv, X$^{su}$, y, and Z.

Examples of *Saccharomyces cerevisiae* genes include: PRE3, PUP1, PUP3, PRE2, PRE10, PRE1, PRE8, SCL1, PUP2, PRE5, PRE7, PRE4, RPT2, RPT3, RPN3, RPN11, RPN12, RPT6, RPN1, RPN2, RPT1, RPT5, RPT4, SKI6, RRP4, DIS3, TSC10, RAT1, GND1, EXO70, ERG10, ACC1, RPP0, ACT1, ARP100, ARP3, PAN1, ARP2, ARP4, ARP9, SPE2, CYR1, ALA1, TPS1, TUB1, ABF1, DED81, NIP1, YHC1, SNU71, ATM1, MAK5, ROK1, DED1, SPB4, AUR1, PSE1, ALG1, TUB2, BPL1, MSL5, ERG24, ERG26, ERG25, CMD1, HCA4, SHE9, SHE10, CAK1, PIS1, CHO1, CDS1, ESR1, NUD1, CDC47, CDC13, CDC37, CDC1, CDC4, CDC20, CDC6, CDC46, CDC3, KAR1, BBP1, HRP1, CCT2, CCT3, HSP10, SMC1, SMC2, CHC1, CFT2, CLP1, COP1, SEC26, SEC27, RET2, SEC21, COF1, CCT4, CCT1, CCT6, SEC24, SEC7, PCF11, RNA15, RNA14, FIP1, YSH1, TFB4, TSM1, APC2, APC5, SEC31, TAF47, TAP42, MPP10, CDC53, CKS1, CDC28, KIN28, CNS1, ERG11, DBP10, DBP8, PRO3, DYS1, ALR1, TID3, DNA2, SSL2, RAD3, RFA3, RFA2, RFA1, RFC4, RFC5, RFC3, RFC2, RFC1, TOP2, RAP1, RPC25, PRI2, PRI1, POL1, POL12, HUS2, CDC2, POL2, DPB2, RPB10, RPA135, RPA190, RPA43, RPB8, RPO26, RPB5, RPC40, RPC19, SRB7, SRB4, RGR1, RPB11, SRB6, RPB2, RPB7, RPO21, RET1, RPO31, RPC31, RPC34, RPC53, RPC82, RPB12, RPB3, DPM1, DIP2, RNT1, CDC8, CDC14, DUT1, UBA2, UBA1, UBC9, CDC34, ENP1, ERD2, SSS1, SEC61, SEC63, SEC62, GNA1, GPI8, DAM1, DUO1, IRR1, PRP3, TIM9, HSH49, SUP35, EXM2, MEX67, ERG9, ERG20, FAS2, FAS1, NOP1, FAD1, AOS1, FBA1, NCB2, BRN1, TUB4, GDI1, GOG5, SRM1, CDC25, SPT16, YIF2, BET4, CDC43, MRS6, BET2, PRO1, GLN1, GLN4, GRS1, YIP1, FOL2, GPA1, CDC42, SAR1, YPT1, SEC4, GSP1, TEM1, RHO1, CDC24, RNA1, GUK1, VMA16, PMA1, HKR1, SIS1, MGE1, HSP60, HSF1, HAS1, MOT3, HTS1, ESA1, HSL7, HOM6, RIB7, SLY1, CSL4, PUR5, CSE1, IPP1, MDM1, USO1, SOF1, MAK11, LAS1, TEL2, DPB11, SGD1, FAL1, MTR3, MTR4, SPP2, SIK1, RRP7, POP4, RRP1, POP3, BFR2, CDC5, NRD1, MET30, MCM6, RRP46, SAS10, SCC2, ECO1, PRP43, BET3, BET5, STN1, NFS1, IDI1, SRP1, KAP95, CBF2, SKP1, CEP3, CTF13, ERG7, KRS1, PSA1, PMI40, ALG2, SSF1, MED7, RSC4, CDC54, MCM2, AFG2, ERG12, MVD1, CDC48, MHP1, ERV1, SSC1, TIM44, TIM17, TIM23, TOM22, TOM40, MAS1, MCD1, MMC1, STU1, JAC1, ABD1, CEG1, PAB1, MTR2, SEC16, ROT1, INO1, MLC1, MYO2, GPI2, SPT14, NAT2, NMT1, TRM1, NCP1, NBP1, ACF2, SPP41, NUT2, LCP5, PRP19, NMD3, RFT1, NNF1, NDC1, CRM1, KAR2, NIP29, NAB2, NIC96, NUP145, NUP49, NUP57, NUP159, NSP1, NUP82, CDC39, NPL4, POP7, NTF2, MAK16, NPL3, NOP2, NOP4, NHP2, NOP10, GAR1, NBP35, WBP1, STT3, SWP1, OST2, OST1, ORC1, ORC6, ORC5, ORC4, ORC3, RRR1, SAT2, PWP2, PEX3, TOR2, PIK1, SEC14, STT4, MSS4, PCM1, GPM1, SEC53, ERG8, YPDI, PAP1, NAB3, RRN7, SEN1, CFT1, PRP11, PRP21, PRP39, PRP24, PRP9, SLU7, PRP28, PRP31, IFH1, PTA1, SUB2, FMI1, MAS2, ESS1, PFY1, POL30, POP1, PDI1, RAM2, CDC7, SMP3, CDC15, YTH1, QRI2, YAE1, SFI1, SEC1, BET1, SEC6, SEC13, SEC2, SEC8, CBF5, CDC19, YRB1, RHC18, DBF4, SDS22, MCM3, CEF1, ALG11, GAA1, MOB1, NIP7, TIP20, SEC5, SEC10, GPI10, RRP3, CDC45, DIB1, MIF2, HOP2, PBN1, NOP5, RPP1, POP5, POP8, POP6, ERO1, MPT1, DNA43, ESP1, SMC3, LST8, STS1, RPM2, RNR1, RNR2, RNR4, RPS20, RPL25, RPL3, RPL30, RPL32, RPL37A, RPL43A, RPL5, RPL10, RPS3, CET1, YRA1, SNM1, GLE1, DBP5, DRS1, DBP6, BRR2, RRN3, RRN6, RRN11, MED6, PRP16, RPR2, DIM1, RRP43, RRP42, RRP45, SEC20, BOS1, CDC12, GLC7, PKC1, IPL1, SGV1, NRK1, RAD53, LCB2, LCB1, MPS1, SES1, SPC3, SEC11, RIO1, ARP7, NEO1, YJU2, POB3, ARH1, IQG1, HRT1, HYM1, MAK21, FUN20, FUN9, NBN1, STB5, YIF1, SMX4, YKT6, SFT1, SMD1, PRP6, LSM2, NUF1, SPC97, SPC42, SPC98, CDC31, SPC19, SPC25, SPC34, SPC24, NUF2, PRP40, MCD4, ERG1, SMC4, CSE4, KRR1, SME1, TRA1, RLP7, SCH9, SMD3, SNP2, SSF2, SPC72, CDC27, CDC23, CDC16, APC1, APC11, APC4, ARC19, RPN6, RPN5, RSC6, RSC8, STH1, SFH1, TIM12, TIM22, TIM10, SQT1, SLS1, JSN1, STU2, SCD5, SSU72, ASM4, SED5, UFE1, SYF1, SYF2, CCT5, TBF1, TOA2, TOA1, SUA7, TAF90, TAF61, TAF25, TAF60, TAF17, TAF145, TAF19, TAF40, TAF67, TFA2, TFA1, FCP1, TFG1, TFG2, TFB1, CCL1, SSL1, TFB3, TFB2, PZF1, BRF1, TFC5, TFC4, TFC3, TFC7, TFC6, TFC1, SPT15, THI80, THS1, SPT6, SPT5, ROX3, REB1, MCM1, MED4, MOT1, MED8, EFB1, YEF3, SUI1, CDC95, TIF11, SUI3, GCD11, SUI2, GCD6, GCD7, GCD2, GCD1, RPG1, GCD10, PRT1, TIF34, CDC33, TIF5, SUP45, GCD14, TIM54, SEC17, TPT1, TRL1, CCA1, SEN54, SEN2, SEN15, SEN34, WRS1, SLN1, TYS1, SNU56, PRP42, CUS1, PRP4, PRP8, SNU114, USS1, UFD1, SMT3, RSP5, QRI1, ALG7, UGP1, VTI1, VAS1, SEC18, CTR86, and ZPR1.

The vaccinia virus of the invention can be used in a method of treatment of the human or animal body. Such treatment includes a method of treating the growth of neoplastic cells which comprises administering to a patient in need of treatment the vaccinia virus of the invention. The recombinant vaccinia virus of the invention may or may not contain exogenous nucleic acid sequence.

For use of the expression vectors in therapy, the expression vectors will usually be packaged into viral particles and the particles delivered to the site of the tumor. The particles may be delivered to the tumor by any suitable means at the disposal of the physician.

Recombinant infectious vaccinia viruses for use in man can be prepared as described in Br. Med. Bull. 25: 131-135 (1969). Preparations suitable for vaccination often contain $10^6$ to $10^8$ plaque forming units per 0.05 ml.

One suitable route of administration is by injection of the particles in a sterile solution. While it is possible for the particles to be administered alone it is preferable to present them as pharmaceutical formulations. The formulations comprise a particle, together with one or more acceptable carriers thereof and optionally other therapeutic ingredients. The carrier or carriers must be "acceptable" in the sense of being compatible with the other ingredients of the formulation and not deleterious to the recipients thereof.

Particles may also be administered by regional perfusion or direct intratumoral direction, or direct injection into a body cavity (intracaviterial administration), for example by intraperitoneum injection.

It is also known that muscle cells can take up naked DNA and thus sarcomas may be treated using an expression vector of the invention in which naked DNA is directly injected into the sarcoma.

Formulations suitable for parenteral or intramuscular administration include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents and preserving agents. The formulations may be presented in unit-dose or multi-dose containers, for example sealed ampoules and vials, and may be stored in a freeze-dried (lyophilized) condition requiring only the addition of the sterile liquid carrier, for example water, for injections, immediately prior to use.

It should be understood that in addition to the ingredients particularly mentioned above the formulations may include other agents conventional in the art having regard to the type of formulation in question. Of the possible formulations, sterile pyrogen-free aqueous and non-aqueous solutions are preferred.

The doses may be administered sequentially, eg. at daily, weekly or monthly intervals, or in response to a specific need of the patient. Preferred routes of administration are parenteral injection, typically intradermal injection or intramuscular injection or intratumoral injection.

Typically, the particle will be administered to the patient and then the uptake of the vector by the infected cells monitored, for example by recovery and analysis of a biopsy sample of targeted tissue.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Chemotherapy will normally involve parenteral administration. Administration by the intravenous route is frequently found to be the most practical. For glioblastoma the route is often intratumoral.

Tumors which may be treated using the expression vector of the present invention include any tumors capable of being treated by the expression vector of the invention and thus are not limited to any one particular class of tumors. Particularly suitable tumor types include breast, colorectal and ovarian tumors, as well as pancreatic, melanoma, glioblastoma, hepatoma, small cell lung, non-small cell lung, muscle and prostate tumors.

It will be understood that where treatment of tumors is concerned, treatment includes any measure taken by the physician to alleviate the effect of the tumor on a patient. Thus, although complete remission of the tumor is a desirable goal, effective treatment will also include any measures capable of achieving partial remission of the tumor as well as a slowing down in the rate of growth of a tumor including metastases. Such measures can be effective in prolonging and/or enhancing the quality of life and relieving the symptoms of the disease.

EXAMPLES

Particular aspects of the present invention may be more readily understood by reference to the following examples, which are intended to exemplify the invention, without limiting its scope to the particular exemplified embodiments.

Example 1

Construction of a TK/VGF Negative Phenotype Double Mutant Vaccinia Virus

A vaccinia virus containing mutations in the TK and VGF genes was constructed to produce a recombinant virus with negative TK and VGF phenotypes. A two tier process was used to generate the double mutant vaccinia virus. In the first tier the VGF genes were inactivated, followed by the second tier, in which TK gene was inactivated.

VGF− Vaccinia Virus

Mutations in the VGF genes were constructed according to the method of Buller, et al. (1988). Briefly, a 1.6-kilobase-pair BglII restriction endonuclease fragment containing the complete nucleotide sequence encoding VGF was isolated from pVG3 as described in Venkatesan, et al., *J. Virol.* 44:637-646 (1982). The Klenow polymerase repaired fragment was ligated into HincII-cleaved pUC13, and the mixture was used to transform competent *Escherichia coli* JM109. β-Gal− colonies (white versus β-Gal+ blue) were isolated by using the X-Gal-IPTG screening system. A plasmid (pSC16) was obtained that contained the entire VGF gene with the direction of viral gene transcription from the plasmid HindIII site toward the BamHI site.

The pSC16 plasmid was cleaved with AccI and then subjected to bidirectional BAL 31 digestion and Klenow enzyme repair. The DNA was modified by the addition of BglII linkers, circularized with T4 DNA polynucleotide ligase, and used to transform competent HB101 bacteria. Minipreparations of plasmids from isolated colonies were characterized by digestion with BglII and HindIII. A plasmid, pSC 18, was identified in which the AccI site had been destroyed by a deletion of approximately 250 base pairs and a BglII site had been inserted. This plasmid was treated sequentially with BglII and calf intestinal phosphatase and ligated to an appropriately modified XbaI-SmaI fragment from pSC10, described in Chakrabarti, et al., Mol. Cell. Biol. 5:3403-3409 (1985), which contained the vaccinia virus 11K promoter coupled to the *E. coli* lacZ gene (β-galactosidase cassette). Competent JM109 cells were transformed, and blue colonies (β-Gal+) were isolated. One colony yielded a plasmid (pSC20) which, on characterization with HindIII and ClaI restriction endonucleases, showed a pattern consistent with the β-galactosidase cassette having been inserted into the disrupted coding region of the VGF gene and in the same transcriptional orientation.

The pSC20 plasmid was then used to introduce the mutated VGF gene into the vaccinia virus genome by homologous recombination, resulting in the production of a VGF− phenotype vaccinia virus. To accomplish this a 25-$cm^2$ flask of CV-1 cells (monkey kidney cells) were grown to confluency in a 6-well plate. The CV-1 cells were infected with 0.05 plaque forming units (pfu) per cell of wild-type vaccinia virus. These cells were then transfected with 5-10 μg (in <50 μl) of plasmid pSC20 using the calcium phosphate-precipitation method. After a 30 minute incubation at room temperature, 9 ml of complete MEM-10 medium was added and the cells were then incubated for 3 to 4 hours at 37° C. Following this incubation period, the medium was removed and replaced with 5 ml complete MEM-10, and then the cells were incubated for 2 days at 37° C. Following the incubation the cells were dislodged with a scraper and transferred to a 15-ml conical centrifuge tube. The tube and its contents were centrifuged for 5 minutes at 1800×g (2500 rpm in a Sorvall H-6000A rotor), at 5° to 10° C. The medium was then aspirated and discarded. The cells were then resuspended in 0.5 ml complete MEM-2.5. The cell suspension was lysed by performing three freeze-thaw cycles, each time by freezing in a dry ice/ethanol bath, thawing in a 37° C. water bath, and vortexing. The resulting lysates were then stored at −70° C. until needed for selection of the VGF− virus.

To isolate VGF− phenotype virus, CV-1 cells were cultured to a confluent monolayer and then trypsinized and resuspended in culture medium. The cells were cultured and placed in a 6-well tissue culture plate at $5\times10^5$ cells/well in a final volume of 2 ml/well. The plate was incubated until the cells were confluent (<24 hours). Following establishment of confluency, 100 µl of transfected cell lysate and 100 µl of 0.25 mg/ml trypsin was mixed and vortexed vigorously. The mixture was incubated for 30 minutes at 37° C. with periodic vortexing at 5 to 10 minute intervals. Following incubation the mixture was vortexed for 30 seconds on ice. Four 10-fold serial dilutions (ranging from $10^{-1}$ to $10^{-4}$) were made for use in the assay. The medium was then aspirated from the cell monolayers and infected with 1.0 ml diluted lysate per well. This solution was incubated for 2 hours with rocking at 30 minute intervals.

Before the 2 hour infection was finished, 2% LMP agarose (Life Technologies; Rockville, Md.) in water (1.5 ml times the number of wells) was melted and placed in a 45° C. water bath to cool. Plaque medium was prepared by making 2× culture medium and warming it to 45° C. A first overlay of agar was then prepared by mixing an equal volume of 2% LMP agarose and plaque medium. The viral inoculum was then removed and an overlay of 3 ml per well was placed in each well and allowed to solidify at room temperature or 4° C. for 2 days.

A second agarose overlay was then prepared by mixing equal volumes of 2% LMP agarose (1 ml×number of wells, melted and cooled to 45° C. as described above) and 2× plaque colorimetric medium (1 ml times the number of wells, warmed to 45° C.) with 1/100 volume of 10 mg/ml neutral red. An additional 1/120 volume of 4% Xgal was added to the plaque colorimetric medium. Each well was then overlayed with 2 ml of this second agarose solution, allowed to solidify, and incubated overnight to permit color development. Plaques with blue coloring indicated the presence of an active β-galactosidase gene and thus an interrupted VGF gene.

Blue plaques were isolated by taking an agar plug of a blue plaque and placing it into a tube with 0.5 ml of culture medium. Each tube was vortexed and subjected to three rounds of freeze-thawing as described above. At the end of the third round the tube and its contents were sonicated in ice-water for 20-30 seconds. The resulting contents of the tube were used to perform successive rounds of plaque purification. These subsequent rounds of purification are necessary in view of the vaccinia virus genome's ability to transfer the genotype of one VGF gene to the other copy within the vaccinia virus genome. Because of this characteristic of vaccinia virus, it is important to select a mutant vaccinia virus clone where both VGF genes are mutated, rather than only one. Often by the fourth round of plaque purification all of the plaques were blue, suggesting that the β-galactosidase cassette was present in both inverted terminal repeats of the vaccinia virus genome. One plaque was designated VSC20. This plaque was used in the construction of the VGF−/TK− double mutant virus.

Once the VSC20 plaque was selected it was amplified to create a virus stock. To amplify the virus from the selected plaque, the plaque plug was selected, resuspended and sonicated as described above. A confluent monolayer of CV-1 cells was then infected with the solubilized plaque material and incubated for 2 days. The infected culture cells were then scraped, lysed, and centrifuged to remove the particulate matter. This material was then used in subsequent scale up procedures to produce a substantial virus stock for storage.

TK−/VGF− Double Mutant Vaccinia Virus

The vaccinia virus VSC20 described above was used in the generation of the VGF−/TK− phenotype vaccinia virus using standard techniques well known in the art. For example, such techniques are described in detail in Moss & Earl, Current Techniques in Molecular Biology, (Ed. Ausubel, et al.) Unit 16.15-16.19 (1998). Purified VSC20 virus (VGF− phenotype) was used to infect HuTK− 143B cells grown to confluency in a 6-well plate. The cells were infected with $6\times10^6$ plaque forming units (pfu) of VSC20 and incubated for 2 hours in the presence of 5-bromodeoxyuridine (BrdU), a nucleotide analog that incorporates into DNA in the presence of a functional TK gene, and results in cell death.

When viral cytopathic effects were observed in the cultured cells (rounding up of cell layer), the culture media was aspirated and the cells were resuspended in complete DMEM with 2.5% serum. Dilutions of cells ($10^{-1}$ to $10^{-3}$) were used to infect confluent HuTK− cells in presence of BrdU in a plaque assay as described above. Only TK negative phenotype viruses can grow in the presence of BrdU. Viral plaques that developed were thus TK negative. Plaques that appeared in this assay were then picked and used to infect further HuTK− cells for 3 cycles. Multiple plaques were then expanded on CV-1 cells.

DNA was extracted from these cells using methods well known in the art. The plaque DNA isolated was used in various molecular biology techniques to determine the presence or absence of VGF and TK mutations. For example the polymerase chain reaction (PCR) reaction was performed to examine the size of the TK and VGF genes. The reaction was performed using standard techniques well known in the art. Briefly, 1 µl of isolated DNA and 1 µl of each primer (TK sense primer: 5'-GATCTTCTATCTCGGTTTCCTCAC-3' (SEQ ID NO. 1); TK antisense TK antisense primer: 5'-GATCGATAATAGATACGGAACGGG-3' (SEQ ID NO. 2); VGF sense primer: 5'-CTGATGTTGTTGTTCGTCGC-3' (SEQ ID NO. 3), VGF antisense primer: 5'-GGTAGTT-TAGTTCGTCGAGTGAACC-3' (SEQ ID NO. 4))) were added to 47 ul of PCR Supermix (Gibco BRL, Gaithersberg, Md.). 25 cycles, each consisting of 15s denaturing (94 C), 30s annealing (55 C) and 2 minute extension (72 C) were performed. The results of the PCR showed the absence of the VGF genes and a normal sized TK gene. Subsequence sequence analysis (Automated sequencing, ABI PRISM DNA Sequencing Kit, Perkin Elmer Applied Biosystems; Foster City, Calif.) of the TK gene revealed a C to A base change resulting in an alanine to glutamic acid amino acid change. The resultant amino acid alteration produced a functionally inactive TK protein, and thus a TK− phenotype. The VGF gene remained disrupted. The isolated double-deleted vaccinia virus (VVDD) was expanded in HeLa cells to $10^9$ pfu per ml and used in subsequent experiments.

Example 2

An Alternative Method of Creating a Double Mutant Vaccinia Virus

In another embodiment, the double mutant vaccinia virus is generated by introducing both VGF and TK mutations through homologous recombination. The VSC20 virus discussed in Example 1 is used to infect HuTk− 143B cells as described above. These cells are contacted with a vaccinia virus shuttle vector containing a mutated TK gene.

The pSC65 vector is used as the source of the TK gene and is described in Chakrabarti, et al., (1997). The XbaI site of the pSC65 vector within the flanking region of the thymidine kinase gene is abolished following digestion using the Klenow enzyme and dNTP filling. A segment of the plasmid is amplified using the PCR reaction to introduce a BSSHII site between the TK flanking region, allowing for the insertion of the multiple cloning site (MCS) of pBluescript KS II (+) (Stratagene; La Jolla, Calif.). To prevent possible antisense transcripts driven by the native vaccinia thymidine kinase promoter, two primers are designed to encode an early termination signal (TTTTTNT) for all three possible open reading frames (5'-ATC GGA GCT CTT TTT ATC TGC GCG GTT AAC CGC CTT TTT ATC CAT (SEQ ID NO. 5) and 5'-ATC GTC TAG ACT CCA CAA TAA AAA CAG ATC ACC TGA TGG ATA AAA (SEQ ID NO. 6)). The primers are hybridized, and dNTPs and Klenow enzyme are added to the reaction mixture. After restriction with SacI/XbaI, the termination signal is gel isolated and ligated into the above plasmid. Gpt is cut out of pBSgpt Puhlmann, et al., Cancer Gene Therapy, (In press), using XhoI and EcoRV and inserted into the MCS of the resulting plasmid pCB022. A promoter cassette consisting of a vaccinia virus p7.5 early/late and a synthetic early/late promoter, as described in Chakrabarti, et al., BioTechniques 23:1094-1097 (1997), in sense and antisense direction is inserted immediately upstream so that the gpt− gene is under control of the p7.5 promoter. A gene of interest, for example the luciferase gene from pGEM-luc (Promega; Madison, Wis.), is inserted, into pCB022 to be driven by the vaccinia synthetic early/late promoter.

The shuttle vector is introduced into a vaccinia virus host cell in conjunction with the VSC20 virus with the VGF− phenotype as described above. Virus progeny are screened for TK− phenotype using BrdU selection described in Example 1. As a result of homologous recombination, a TK−, VGF− negative phenotype is obtained.

Example 3

An In Vitro Comparison of the Double Mutant Vaccinia, TK−, VGF−, and Wild-Type Viruses To compare the growth characteristics of the double mutant VGF−/TK− vaccinia virus with those of the single TK− and VGF− mutants and the wild-type virus, each were grown in confluent and non-confluent cells. Six well plates of confluent and non-confluent (dividing) NIH3T3 (growth factor dependent) were infected with 167 pfu per well of one of the following vaccinia viruses: F13 (wild-type)(Blasco & Moss, Gene 158:157-162 (1995)), VJS6 (thymidine kinase deleted) (Carroll, et al., Vaccine 15:387-394 (1997)), VSC20 (vaccinia growth factor deleted), or VVDD (double deleted). At 24, 36 and 48 hours the growth media was removed, and the cells were harvested as described above. The total viral titers was measured in a plaque assay described below.

The plaque assay was performed as described above with certain modifications. The cells were resuspended in 2 ml of DMEM-2.5 and subjected to one freeze-thaw cycle. Five hundred microliters (500 µl) of cell lysate was used to infect CV-1 cells, as discussed above. After 1 hour an overlay (1:1 1.5% agar to DMEM-10) was placed over a confluent layer of CV-1 cells. Three (3) days later cells were stained with crystal violet and plaques counted.

Shown in FIG. 1 are the plaque assay results (pfu measurements made in CV-1 cells) for each virus at the three time points for growth in NIH3T3 cells. In FIG. 1A (Non-Confluent Cells), the wild-type form of the virus showed the highest level of viral replication. The VGF− and TK− single mutants and the double mutant forms of the virus all replicated in the dividing cells. In FIG. 1B (Confluent Cells) the wild-type form of the virus produced the highest levels of viral progeny in these non-dividing cells, however, the VGF−, TK−, and double mutants failed to show statistically significant replication in these non-dividing cells. Accordingly, the mutations of the present invention restrict viral replication to dividing cells.

Example 4

An In Vivo Comparison of the Double Mutant Vaccinia, TK−, VGF−, and Wild-Type Viruses To investigate the effect of the double mutations and the corresponding VGF−/TK− phenotype of the mutant vaccinia virus on pathogenesis, female nude mice were injected with $10^5$ MC38 cells (murine colon adenocarcinoma cells) subcutaneously. It is thought that vaccinia virus replicates in MC38 tumor cells and will eventually cause the death of the immunocompromised mouse. On day 10, when tumors were approximately 100 mm$^3$ in volume, the mice received either $10^7$ or $10^8$ pfu of one of the four viruses discussed in Example 3. Specifically, F13 (wild-type), VJS6 (thymidine kinase deleted), VSC20 (vaccinia growth factor deleted), or VVDD (double deleted) were used in this experiment and injected intraperitoneally. The mice were observed for survival after viral infection.

Figure 2:
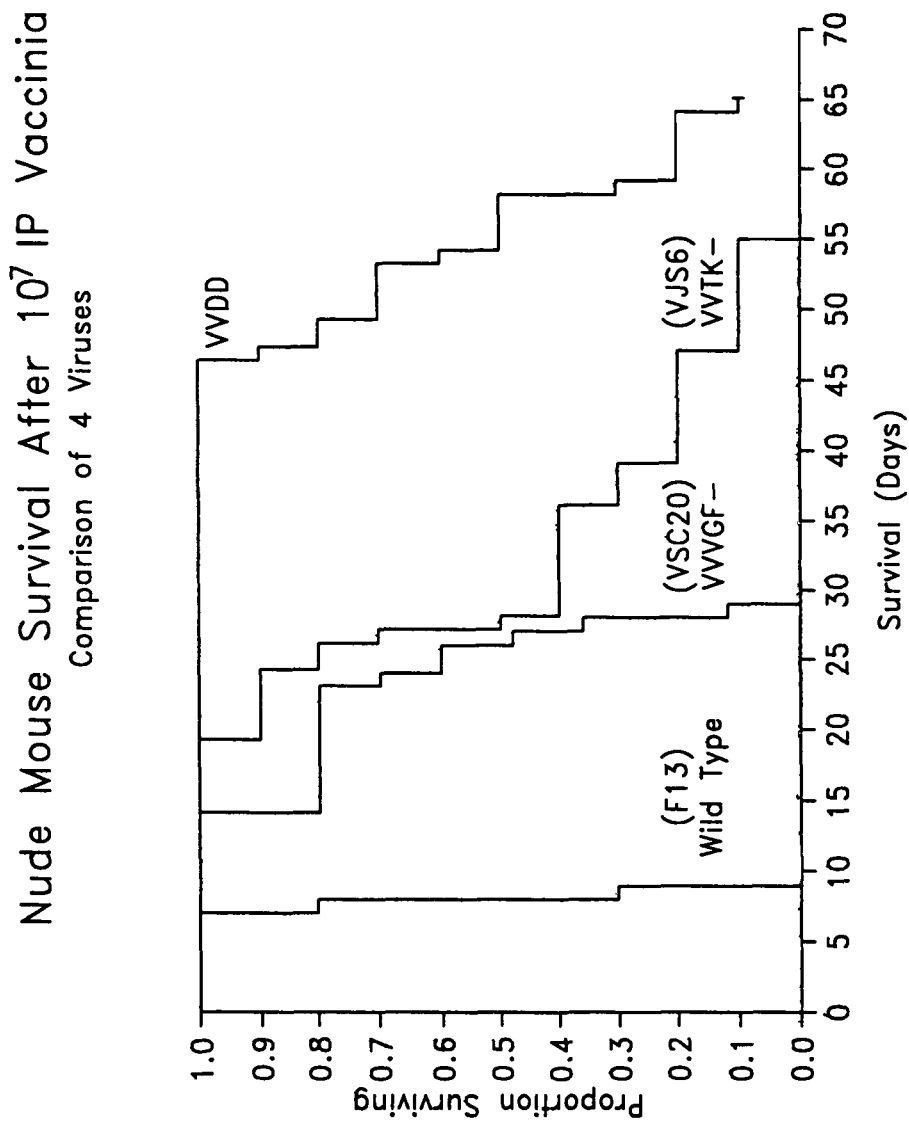
FIG. 2 depicts the proportion of surviving mice challenged with $10^7$ infectious particles (IP) of wild-type (F13), VGF− phenotype vaccinia virus VVVGF− (VSC20), TK− phenotype vaccinia virus VVTK− (VJS6), and the VGF−/TK− double mutant vaccinia virus VVKK.
Figure 3:
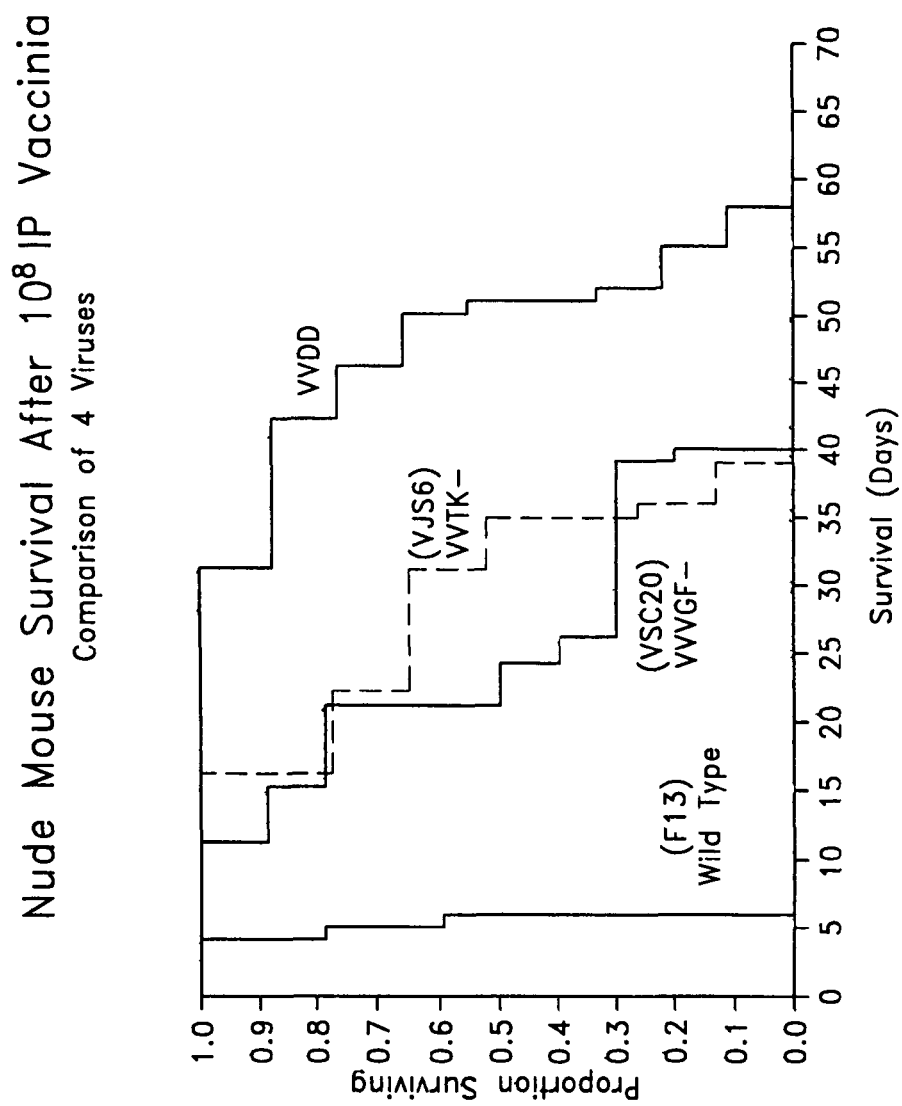
FIG. 3 depicts the proportion of surviving mice challenged with $10^8$ IP of wild-type (F13), VGF− phenotype vaccinia virus VVVGF− (VSC20), TK− phenotype vaccinia virus VVTK− (VJ86), and the VGF−/TK− double mutant vaccinia virus VVDD.

As shown in FIGS. 2 and 3, there are substantial differences in survival between mice challenged with F13, those challenged with the two single mutation forms of the virus, or the double mutant vaccinia virus (VVDD). In FIG. 2, mice that were challenged with the four virus types showed a marked difference relative to the number of mutations present in the viral genome. Comparing the point at which each of the four virus infected groups had 50% of their members still living, the wild-type virus had killed half of the mice treated with this form of the virus by approximately day 6. The VSC20 and VJ56 virus infected mice reached the 50% survival point on about days 26 and 27 (respectively). Mice infected with the double mutant virus showed significantly longer survival times and did not reach the 50% survival point until about day 54. These results indicate that mice harboring tumor cells survived viral infection for significantly longer periods of time when infected with the double negative phenotype form of the vaccinia virus.

Mice challenged with tumor cells as described above and exposed to VVDD substantiate the reduced toxicity of the vector. For example, half of the mice that were infected with the wild-type form of the virus were dead by day 6, and after that time point all of the remaining mice died. In contrast, mice exposed to cancer cells and to the double mutant vaccinia virus showed a substantial difference in survival relative to those mice infected with the wild-type form of the virus. As shown in FIG. 3, 50% of the mice infected with the double negative phenotype mutation and the cancer cells survived until day 58. The mice infected with the TK− and VGF− single mutation viruses reached the 50% survival point on days 35 and 21, respectively. These results further confirm the observation that mice harboring dividing cancer cells survive longer when infected with the double mutant vaccinia virus of the present invention.

Example 5

An In Vivo Comparison of the Wild-Type, Single Mutant, and Double Mutant Vaccinia Expressing the Green Fluorescent Protein This Example discusses an examination of host survival after administration of various forms of vaccinia. To make this comparison, less than $10^7$ pfu of F13 (wild type), VJS6 (TK-deleted), VSC20 (VGF-deleted), and VVDDEGFP (TK– and VGF-deleted expressing green fluorescent protein) were injected intraperitoneally (in 2 ml of HBSS/0.1% BSA, Calbiochem, La Jolla, Calif.) into six week old female, athymic (C57B1/6) mice obtained from the National Institutes of Health small animal facility (Frederick, Md.). The animals were examined daily with survival as an end point. Animals who became moribund due to viral pathogenicity were euthanized. The percent survival is graphed as a function of time. The data from this experiment is shown in FIG. 4.

Figure 4:
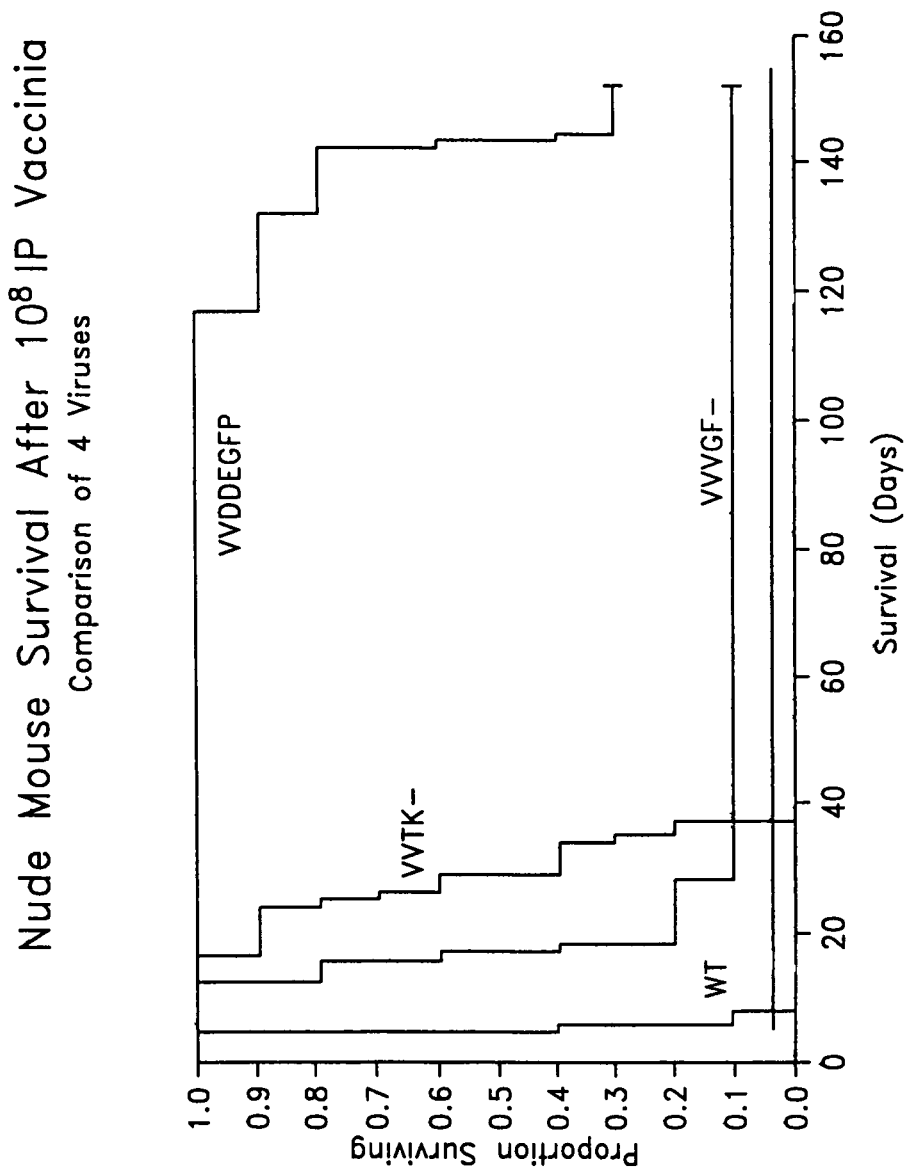
FIG. 4 depicts the proportion of surviving mice challenged with $10^8$ IP of wild-type (F13), VGF− phenotype vaccinia virus (VSC20) VVVGF−, TK− phenotype vaccinia virus VVTK− (VJS6), and the VGF−/TK− double mutant vaccinia virus VVDDEGFP, which contains the gene for the green fluorescent protein.

As shown in FIG. 4, 50% of the mice infected with the double negative phenotype mutation and the cancer cells survived until day 141. The mice infected with the TK– and VGF– single mutation viruses reached the 50% survival point on days 38 and 19, respectively. These results further confirm the observation that mice survive longer when infected with the double mutant vaccinia virus of the present invention, even when that mutant virus is expressing an exogenous nucleic acid sequence.

Example 6

Figure 5:
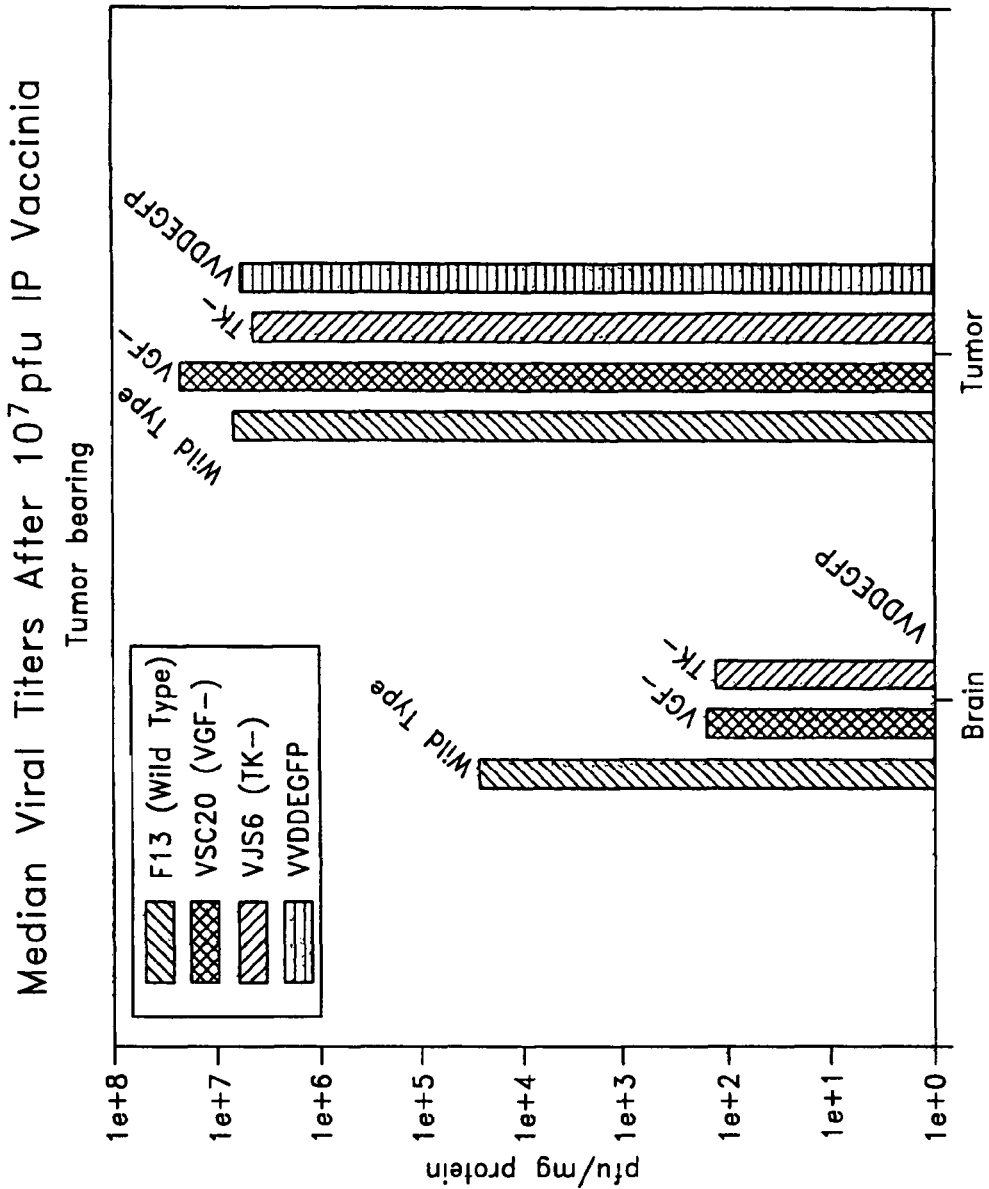
FIG. 5 depicts median viral titers sampled from brain and tumor tissue after administration of $10^7$ pfu IP to tumor bearing nude mice. Viral titers are shown as pfu/mg protein.

An In Vivo Comparison of the Neurovirulence of Double Mutant Vaccinia, TK⁻, VGF⁻, and Wild-Type Viruses in Brain Tissue A comparison of neurovirulence, or ability to replicate in neurological tissues, in mice was performed using the viruses discussed in Example 5. Median viral titers were measured after $10^7$ pfu of the viruses were administered IP to tumor bearing host animals. Virus titers were measured as a function of pfu/mg protein from brain and tumor tissue harvested from infected host animals. The results are shown in FIG. 5.

As shown, the double mutant vaccinia virus VVDDEGFP failed to replicate appreciably in brain tissue. In contrast, the wild-type and single mutant forms of vaccinia were able to replicate in the brain tissue of the host animals. All forms of the virus were able to replicate in the host's tumor cells. These results demonstrate that the double mutant viruses of the disclosed invention are safer than other forms of vaccinia virus, when administered to a tumor bearing host.

Example 7

Construction of a Double Mutant Vaccinia Virus Expression Vector for Expressing Cytosine Deaminase (CD)

A double mutant vaccinia virus is constructed according to the method described in Example 1 except that a gene encoding cytosine deaminase (CD) is incorporated into the shuttle vector containing the TK gene.

The CD gene containing shuttle vector is introduced into the vaccinia virus host cell for homologous recombination using a liposome mediated transfection protocol. Briefly, a 6-well tissue culture plate is seeded with $5\times10^5$ CV-1 cells/well in complete DMEM-10 medium. The cells are grown to near confluency. The VGF– VSC20 virus of Example 1 is prepared and used to infect the monolayer of CV-1 cells for a period of 30 minutes. Approximately 5 minutes before the end of the infection, a liposome suspension is prepared according to the method of Whitt et al., Current Techniques in Molecular Biology, (Ed. Ausubel, et al.) Unit 9.4 (1998). In a 12×75-mm polystyrene tube is placed 1 ml of DMEM medium (Biofluids; Rockville, Md.) for each well to be tested. The liposome suspension is vortexed and 15 µl of the suspension is added to the medium. The mix is vortexed again. To this solution is added 5 µg of shuttle vector DNA, followed by gentle mixing. Following preparation of the liposome solution, the virus inoculum is aspirated from the CV-1 cells, and the DNA/liposome complex is added directly to the cells. The cells are incubated 4 hours.

Utilizing the method of homologous recombination, the CD gene under the control of the vaccinia virus synthetic early/late promoter (See TABLE 1) is introduced into the vaccinia virus genome of VSC20. Since the VSC20 virus already contains a mutation in the VGF gene, it has a negative VGF phenotype. After the introduction of the CD gene into the TK gene locus by homologous recombination from the shuttle vector, the resulting double mutant vaccinia virus possesses a negative phenotype for VGF, a negative phenotype for TK, and it will cause cells infected with this virus to express the CD gene.

Virus particles containing the CD gene are identified using positive selection pressure and repeated rounds of plaque purification described above.

Example 8

In Vivo Antitumor Response of Double Mutant Vaccinia Virus Following Systemic Injection This Example discusses data gathered from a tumor bearing host injected systemically with the double mutant virus. Approximately $10^5$ MC-38 (murine colon cancer) cells in 100 µl of DMEM were injected subcutaneously into the right flanks of 6-week old female athymic (C57B16) mice. When the tumors reached 75 to 125 $mm^3$ in volume, $10^9$ pfu of VVDDEGFP or HBSS (Hanks Balanced Salt Solution, Biofluids, Chicago, Ill.) control was injected intraperitoneally in 2 ml of HBSS/0.1% BSA (Calbiochem, La Jolla, Calif.). Tumor width and length was measured twice weekly by a blinded investigator. Tumor volume was calculated as $[(width)^2 \times length]0.52$. Tumor volume was graphed as a function of time. The data from this experiment is shown in FIG. 6.

Figure 6:
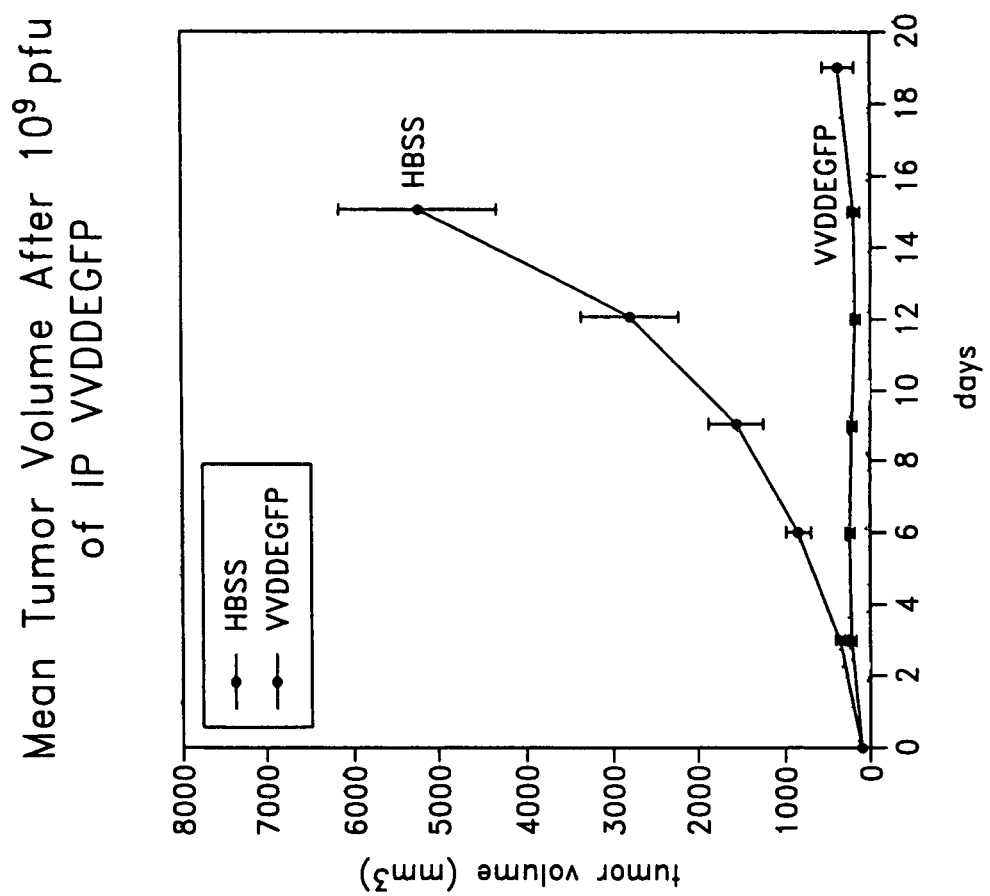
FIG. 6 depicts changes in mean tumor volume after administration of $10^9$ pfu IP of the double mutant VVDDEGFP and virus free buffer. Change in tumor volume is shown in cubic millimeters ($mm^3$).

The data shown in FIG. 6 demonstrates animals administered a double mutant vaccinia virus of the disclosed invention experience little or no tumor volume increase, as opposed to animals that received medium alone. These results show that administration of a double mutant vaccinia virus of the disclosed invention to a tumor bearing-host animal can significantly impact tumor growth in that host.

Example 9

In Vivo Use of Double Mutant Vaccinia Virus Carrying HER2 Gene in Combination with Monoclonal Antibody Therapy In this Example, a tumor-bearing host is infected with a double mutant vaccinia virus that carrying the gene for the HER2 protein. The virus infected tumors express the HER2 protein. Once expression of the HER2 protein has occurred, the host is provided an efficacious dose of Herceptin (Trastuzumab) (Genentech, South San Francisco, Calif.). Herceptin is an IgG 1 kappa monoclonal antibody that contains human frame-work regions with the complementarity-determining regions of a murine antibody (4D5) that binds to the extracellular domain of the human epidermal growth factor receptor2 protein, HER2. This receptor can be expressed by the virus and thus improve the effect of Herceptin.

Cells infected with the virus will be killed either through the replication of the virus or through the action of the monoclonal antibody. Further, radio-labeled or chemo-labeled antibodies are also used in this treatment regime. The labeled, antibodies will kill HER2 expressing cells and by-stander non-infected cells, as well. This treatment results in the elimination of tumor cells.

Example 10

Use of Double Mutant Vaccinia Virus Carrying Somatostatin Gene to Facilitate Tumor Imaging A patient with a known carcinoid tumor is infected with a double deleted virus carrying the somatostatin receptor. The virus infects tumor cells and expresses the receptor. The patient then receives an intravenous injection of 5.5 millicuries of Indium 111 labeled Octreotide to image somatostatin receptor-expressing cells.

Whole body images demonstrate relatively normal uptake in liver, spleen, kidney and bladder. There is however a diffuse mid-abdominal small bowel uptake which is beyond the usual amount of activity seen on both the 4 hour and 24 hour images. This amount of activity is not normal and is most likely small bowel involvement with carcinoid. SPECT activity of the liver demonstrates multiple focal areas of increased uptake seen with multiple metastatic carcinoid deposits in the liver. The results of this experiment indicate the utility of this procedure with which to image tumors in a subject.

Example 11

Use of Double Mutant Vaccinia Virus Carrying Transferrin Receptor Gene to Facilitate Tumor Imaging Another example of tumor imaging exploits work recently published (Nat. Med. March; 6(3):351-5(2000)) using the transferrin receptor to enhance uptake of an iron-based contrast material used for MRI imaging. A double mutant vaccinia virus carrying the transferrin receptor (ETR) gene is engineered to express the ETR gene as a reporter that shuttles targeted superparamagnetic nanoparticles into virus infected tumor cells. The internalizing receptor used is a human transferrin receptor that lacks the iron-regulatory region and mRNA destabilization motifs in the 3' untranslated region and therefore constitutively overexpresses high levels of the receptor protein in the tumor cell. These features result in approximately a 500% increase in holo-transferrin bound by stably transfected cells in culture. The receptor-targeted MR reporter consists of 3-nm monocrystalline iron oxide nanoparticles (MION), sterically protected by a layer of low-molecular-weight dextran to which human holo-transferrin (Tf) is covalently conjugated (Tf-MION). Several synergistic effects theoretically contribute to visualizing transgene expression in vivo.

Example 12

Inducing Antibodies Against an Antigen Expressed by a Vaccinia Virus Double Mutant Expression Vector T cells and B cells both comprise cell surface proteins which can be utilized as "markers" for differentiation and identification. One such human B cell marker is the human B lymphocyte-restricted differentiation antigen Bp35, referred to as "CD20." CD20 is expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells, ie, those B cells whose unabated proliferation can lead to B cell lymphoma. Thus, the CD20 surface antigen has the potential of serving as a candidate for "targeting" of B cell lymphomas.

Antibodies raised in an individual suffering from a B cell lymphoma are efficacious as a therapeutic modality. Accordingly, the double mutant vaccinia virus expression vector of the present invention can be used to express a B cell lymphoma specific antigen in a subject suffering from B cell-lymphoma.

To treat an individual presenting a B cell lymphoma, a double mutant vaccinia virus expression vector is constructed according to the methods described in Examples 1 and 2. Incorporated into the double mutant expression vector is an antigenic portion of the CD20 surface antigen. An infectious dose of the double mutant vaccinia virus expression vector encoding the CD20 antigen is provided to a subject, and thus the cells of that subject. The mutant vaccinia virus construct enters into an appropriate host cell and begins to express the CD20 antigen. The immune system of the treated subject then responds to the expression of the antigen and mounts an antibody response to the CD 20 antigen.

Example 13

Inducing a Cellular Response Against an Antigen Expressed by a Vaccinia Virus Double Mutant Expression Vector The human immune system can be divided generally into a humoral category and a cellular category. Antibodies and the complement system comprise the humoral system while cytotoxic T cells, NK cells, macrophages, and other cell types comprise the cellular category. The vaccinia virus expression vectors of the present invention can be used to raise a cellular immune responses from a treated individual.

To induce a cellular immune response in an individual, a double mutant vaccinia virus expression vector is constructed according to the methods described in Examples 1 and 2. It is known that the human immunodeficiency virus (HIV) gag protein can induce cellular immune response when used to immunize a mammalian subject. Accordingly, an antigenic portion of the HIV gag protein is incorporated into the double mutant expression vector. An infectious dose of the double mutant vaccinia virus expression vector encoding the HIV gag protein is provided to a subject, and thus the cells of that subject. The mutant vaccinia virus construct enters into an appropriate host cell and begins to express the HIV gag protein. The immune system of the treated subject then responds to the expression of the antigen and generates a cellular response to the HIV gag protein.

Example 14

Inducing Cell Death by Infecting a Tumor Cell with a Vaccinia Virus Double Mutant Expression Vector Containing a Suicide Gene Murine colon adenocarcinoma cells (MC38 cells) are grown to semi confluency and then infected with the double mutant vaccinia virus expression vector described in Example 7 that expresses the cytosine deaminase (CD) gene. A control culture of MC38 cells is also established in which MC38 cells are grown and infected with a double mutant vaccinia virus that does not contain the CD gene. Following infection of both cell cultures a dose of 5-fluorocytosine (5-FC) is added to both cultures. The dose of 5-FC is of sufficient concentration to cause cell death in an MC38 cell expressing the CD gene yet non-lethal to cell without a CD gene.

As a result of the treatment of the two virus infected cell cultures with 5-FC, nearly 100% of the MC38/CD+ cells are killed as a result of the 5-FC exposure. In contrast, the MC38/CD− cells are not affected by the 5-FC exposure. The results from this example show that the double mutant vaccinia virus expression vectors of the present invention are effective at introducing genes to tumor cells that subsequently lead to the death of the virus infected tumor cells.

While particular embodiments of the present invention have been described in detail, it will be apparent to those of skill in the relevant, art that these embodiments are exemplary, rather than limiting. The true scope of the invention is that defined within the attached claims and equivalents thereof. All references cited herein are hereby expressly incorporated by reference.

What is claimed is:

1. A method of introducing an exogenous nucleotide sequence into a mammalian tumor cell, comprising:
   providing a composition comprising a vaccinia virus expression vector with a negative thymidine kinase phenotype and a negative vaccinia virus growth factor phenotype, wherein the vector selectively replicates in the tumor cells but is substantially incapable of replicating in non-dividing cells and wherein the vector has enhanced safety;
   contacting said mammalian tumor cell with said composition; and
   expressing said exogenous nucleotide sequence in the tumor cell, thereby producing an amount of an expression product.

2. The method of claim 1, wherein said exogenous nucleotide sequence encodes a polypeptide.

3. The method of claim 1, wherein the mammalian tumor cell is in a host, and wherein producing said amount of said expression product results in production of an antibody response by said host against said expression product.

4. The method of claim 1, wherein producing said amount of said expression product results in tumor cell death.

5. A method of inducing cell death of a dividing cancer cell, comprising contacting the dividing cancer cell with a composition comprising a vaccinia virus expression vector with a negative thymidine kinase phenotype and a negative vaccinia virus growth factor phenotype, thereby inducing cell death of the dividing cancer cell.

6. The method of claim 1, wherein the vaccinia virus expression vector is a VVDDEGFP expression vector.

7. The method of claim 1, wherein the mammalian tumor cell is a breast, colorectal, ovarian, pancreatic, melanoma, glioblastoma, hepatoma, small cell lung, non-small cell lung, muscle or prostate cell.

8. The method of claim 5, wherein the vaccinia virus expression vector is a VVDDEGFP expression vector.

9. The method of claim 5, wherein the dividing cancer cell is a mammalian tumor cell.

10. The method of claim 5, wherein the dividing cancer cell is a breast, colorectal, ovarian, pancreatic, melanoma, glioblastoma, hepatoma, small cell lung, non-small cell lung, muscle or prostate cell.

11. The method of claim 9, wherein contacting said dividing mammalian tumor cell with said composition is performed in vivo and said exogenous nucleotide sequence is expressed in vivo, thereby producing an amount of an expression product in vivo.

12. The method of claim 11, wherein the tumor cell comprises a dividing cancer cell, and wherein the method induces cell death of the dividing cancer cell in vivo.

13. The method of claim 1, wherein said exogenous nucleotide sequence comprises a suicide gene.

14. The method of claim 13, wherein said suicide gene comprises cytosine deaminase.

15. The method of claim 13, wherein said suicide gene comprises carboxypeptidase G2.

16. The method of claim 1, wherein said exogenous nucleotide sequence comprises an imaging gene.

17. The method of claim 16, wherein said imaging gene comprises a somatostatin receptor.

18. The method of claim 16, wherein said imaging gene comprises a transferrin receptor.

19. The method of claim 1, wherein said exogenous nucleotide sequence comprises a tumor suppressor gene.

20. The method of claim 1, wherein said exogenous nucleotide sequence comprises a pathogenic antigen gene.

* * * * *

UNITED STATES PATENT AND TRADEMARK OFFICE
CERTIFICATE OF CORRECTION

| | | |
|---|---|---|
| PATENT NO. | : 8,506,947 B2 | Page 1 of 1 |
| APPLICATION NO. | : 11/707453 | |
| DATED | : August 13, 2013 | |
| INVENTOR(S) | : McCart et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 828 days.

Signed and Sealed this
Twenty-first Day of April, 2015

Michelle K. Lee
*Director of the United States Patent and Trademark Office*